(12) United States Patent
Bone et al.

(10) Patent No.: US 11,701,362 B2
(45) Date of Patent: *Jul. 18, 2023

(54) COMPOSITIONS AND METHODS OF USE OF CIS-4-[2-{[(3S,4R)-3-FLUOROOXAN-4-YL]AMINO}-8-(2,4,6-TRICHLOROANILINO)-9H-PURIN-9-YL]-1-METHYLCYCLOHEXANE-1-CARBOXAMIDE

(71) Applicant: Celgene Corporation, Summit, NJ (US)

(72) Inventors: Scott Bone, Bend, OR (US); Tracy Lee Gaebele, Green Brook, NJ (US); Yu Pu, East Hanover, NJ (US); Lianfeng Huang, Basking Ridge, NJ (US)

(73) Assignee: Celgene Corporation, Summit, NJ (US)

( * ) Notice: Subject to any disclaimer, the term of this patent is extended or adjusted under 35 U.S.C. 154(b) by 224 days.

This patent is subject to a terminal disclaimer.

(21) Appl. No.: 17/129,945

(22) Filed: Dec. 22, 2020

(65) Prior Publication Data

US 2021/0128564 A1  May 6, 2021

Related U.S. Application Data

(63) Continuation of application No. 16/845,195, filed on Apr. 10, 2020, now Pat. No. 10,898,488, which is a continuation of application No. 16/710,533, filed on Dec. 11, 2019, now Pat. No. 10,653,697, which is a continuation of application No. 16/150,350, filed on Oct. 3, 2018, now Pat. No. 10,543,214.

(60) Provisional application No. 62/568,107, filed on Oct. 4, 2017.

(51) Int. Cl.
| | | |
|---|---|---|
| A61K 31/52 | (2006.01) | |
| A61K 9/20 | (2006.01) | |
| A61K 9/48 | (2006.01) | |
| A61K 31/522 | (2006.01) | |
| A61K 47/20 | (2006.01) | |
| A61K 47/22 | (2006.01) | |
| A61P 35/00 | (2006.01) | |
| A61K 47/26 | (2006.01) | |

(52) U.S. Cl.
CPC ............ *A61K 31/52* (2013.01); *A61K 9/2009* (2013.01); *A61K 9/2018* (2013.01); *A61K 9/2054* (2013.01); *A61K 9/485* (2013.01); *A61K 9/4858* (2013.01); *A61K 9/4866* (2013.01); *A61K 31/522* (2013.01); *A61K 47/20* (2013.01); *A61K 47/22* (2013.01); *A61P 35/00* (2018.01)

(58) Field of Classification Search
CPC ...... A61K 31/52; A61K 31/522; A61K 47/20; A61K 47/22; A61K 9/2009; A61K 9/2018; A61K 9/2054; A61K 9/485; A61K 9/4858; A61K 9/4866; A61P 35/00
See application file for complete search history.

(56) References Cited

U.S. PATENT DOCUMENTS

| | | | |
|---|---|---|---|
| 4,810,643 | A | 3/1989 | Souza |
| 4,999,291 | A | 3/1991 | Souza |
| 5,229,496 | A | 7/1993 | Deeley et al. |
| 5,391,485 | A | 2/1995 | Deeley et al. |
| 5,393,870 | A | 2/1995 | Deeley et al. |
| 5,580,755 | A | 12/1996 | Souza |
| 5,582,823 | A | 12/1996 | Souza |
| 5,858,968 | A | 1/1999 | Weiner et al. |
| 7,521,446 | B2 | 4/2009 | Albers et al. |
| 7,723,340 | B2 | 5/2010 | Albers et al. |
| 7,759,342 | B2 | 7/2010 | Bennett et al. |
| 8,101,588 | B2 | 1/2012 | Albers et al. |
| 8,158,635 | B2 | 4/2012 | Beauchamps et al. |
| 8,324,225 | B2 | 12/2012 | Brain et al. |
| 8,440,661 | B2 | 5/2013 | Bennett et al. |
| 8,491,930 | B2 | 7/2013 | Fernandez De Gatta Garcia et al. |
| 8,603,527 | B2 | 12/2013 | Bhat et al. |
| 8,680,076 | B2 | 3/2014 | Bennett et al. |
| 9,187,479 | B2 | 11/2015 | Clareen et al. |
| 9,198,866 | B2 | 12/2015 | Bhat et al. |
| 9,512,124 | B2 | 12/2016 | Alexander et al. |
| 9,737,541 | B2 | 8/2017 | Alexander et al. |
| 10,047,090 | B2 | 8/2018 | Chen et al. |
| 2003/0191086 | A1 | 10/2003 | Hanus et al. |
| 2007/0142405 | A1 | 6/2007 | Dong et al. |
| 2008/0021048 | A1 | 1/2008 | Bennett et al. |
| 2009/0312320 | A1 | 12/2009 | Albers et al. |
| 2010/0016586 | A1 | 1/2010 | Bajji et al. |
| 2012/0115890 | A1 | 5/2012 | Beauchamps et al. |
| 2012/0129807 | A1 | 5/2012 | Bennett et al. |
| 2013/0034495 | A1 | 2/2013 | Beauchamps et al. |

(Continued)

FOREIGN PATENT DOCUMENTS

| | | |
|---|---|---|
| WO | WO 1999/015155 A1 | 4/1999 |
| WO | WO 2006/076595 A1 | 7/2006 |

(Continued)

OTHER PUBLICATIONS

Alcorn et al., "c-Jun N-Terminal Kinase 1 is Required for the Development of Pulmonary Fibrosis," *Am. J. Respir. Cell Mol. Biol.*, 40:422-432 (2009).

(Continued)

Primary Examiner — Jeffrey T. Palenik
(74) Attorney, Agent, or Firm — Jones Day

(57) ABSTRACT

Provided are formulations and dosage forms of cis-4-[2-{[(3S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, or a pharmaceutically acceptable salt, tautomer, solvate, hydrate, co-crystal, clathrate, or polymorph thereof.

25 Claims, 48 Drawing Sheets

(56) References Cited

U.S. PATENT DOCUMENTS

| | | |
|---|---|---|
| 2013/0225564 A1 | 8/2013 | Clareen et al. |
| 2014/0093566 A1 | 4/2014 | Bhat et al. |
| 2014/0206697 A1 | 7/2014 | Clareen et al. |
| 2016/0039822 A1 | 2/2016 | Clareen et al. |
| 2016/0096841 A1 | 4/2016 | Alexander et al. |
| 2017/0042902 A1 | 2/2017 | Alexander et al. |

FOREIGN PATENT DOCUMENTS

| | | |
|---|---|---|
| WO | WO 2006/113631 | 10/2006 |
| WO | WO 2007/062338 A2 | 5/2007 |
| WO | WO 2007/127382 A1 | 11/2007 |
| WO | WO 2008/057252 A2 | 5/2008 |
| WO | WO 2011/071491 A1 | 6/2011 |
| WO | WO 2014/172616 A2 | 10/2014 |
| WO | WO 2015/086505 A1 | 6/2015 |
| WO | WO 2016/057370 A1 | 4/2016 |

OTHER PUBLICATIONS

Aljaberi et al., "Functional performance of silicified microcrystalline cellulose versus microcrystalline cellulose: a case study," Drug Development and Industrial Pharmacy 35(9): 1066-1071 (2009).

Bollag et al., "Vemurafenib: the first drug approved for BRAF-mutant cancer," Nat. Rev. Drug Discov., 11(11):873-866 (2012).

Cheson et al., "Revised response criteria for malignant lymphoma," J. Clin. Oncol., 25(9):579-586 (2007).

Chen et al., "SKLB-287, a novel oral multikinase inhibitor of EGFR and VEGFR2, exhibits potent antitumor activity in LoVo colorectal tumor model," Neoplasma, 61(5):514-522 (2014).

Corcoran et al., "EGFR-mediated re-activation of MAPK signaling contributes to insensitivity of BRAF mutant colorectal cancers to RAF inhibition with vemurafenib," Cancer Discov., 2(3):227-235 (2012).

Davis, "Signal transduction by the JNK group of MAP kinases," Cell, 203:239-252 (2000).

Durie et al, "International uniform response criteria for multiple myeloma," Leukemia, 20:1467-1473 (2006).

Edge et al., "Polysaccharide engineering: Silicified microcrystalline cellulose as a novel high-functionality pharmaceutical material", in: Polysaccharide Applications: Cosmetics and Pharmaceuticals, American Chemical Society Symposium Series 737, Chapter 7, pp. 98-112 (1999).

Eisenhauer et al., "New response evaluation criteria in solid tumours: revised RECIST guideline (version 1.1)," Eur. J. Cancer, 45(2):228-247 (2009).

Emens et al., "Chemotherapy: friend of foe to cancer vaccines," Curr. Opin. Mol. Ther., 3(1):77-84 (2001).

Fuchs et al., "Oncogenic β-catenin signaling networks in colorectal cancer," Cell Cycle, 4(11): 1522-1539 (2005).

Hallek et al., "Guidelines for the diagnosis and treatment of chronic lymphocytic leukemia: a report from the InternationalWorkshop on Chronic Lymphocytic Leukemia updating the National Cancer Institute—Working Group 1996 guidelines," Blood, 111(12):5446-5456 (2008).

Kluwe et al., "Modulation of hepatic fibrosis by c-Jun-N-terminal kinase inhibition," Gastroenterology, 138:347-359 (2010).

Lee et al., "Bleomycin induces alveolar epithelial cell death through JNK-dependent activation of the mitochondrial death pathway," Am. J. Physiol. Lung Cell Mol. Physiol., 289:L521-1528 (2005).

Lin et al., "Connective tissue growth factor induces collagen I expression in human lung fibroblasts through the Rac1/MLK3/JNK/AP-1 pathway," Biochim. Biophys. Acta, 1833:2823-2833 (2013).

Medicinenet, "Definition of Cancer," http://www.MedicineNet.com, 2015 (1 page).

Penichet et al., "Antibody-cytokine fusion proteins for the therapy of cancer," J. Immunol. Methods, 284:91-101 (2001).

Roitt et al., Immunology, Third Edition, Mosby, St. Louis, MO, 17.1-17.12 (1993).

Therasse et al., "New guidelines to evaluate the response to treatment in solid tumors," J. Natl. Cancer Inst., 92(3):205-216 (2000).

Tobyn et al., "Physiochemical comparison between microcrystalline cellulose and silicified microcrystalline cellulose," International Journal of Pharmaceutics 169(2):183-194 (1998).

Wen et al., "Updated response assessment criteria for high-grade gliomas: response assessment in neuro-oncology working group," J. Clin. Oncol., 28(11):1963-1972 (2010).

Wilen et al., "Strategies in optical resolutions," Tetrahedron, 33:2725-2736 (1977).

Wilen, Tables of Resolving Agents and Optical Resolutions, (E.L. Eliel, Ed.), University of Notre Dame Press, Notre Dame, IN, p. 268 (1972).

Yoshida et al., "MAP kinase activation and apoptosis in lung tissues from patients with idiopathic pulmonary fibrosis," J. Pathol., 198:388-396 (2002).

NPL search string; terms of record: detecting BRAF NRAS KRAS CTNNB1 mutations and administering anticancer treatments "wild-type" "carboxamide"; downloaded Apr. 28, 2020.

Xu et al. (2018), Oncology Letters, 15: 4471-4476; Jan. 25, 2018.

Seol et al. (2019), Translational Oncology, vol. 12, Issue 2, Feb. 2019, pp. 301-307.

Li et al., 2005, "The use of hypromellose in oral drug delivery," Journal of Pharmacy and Pharmacology, 57(5):533-546.

Streubel et al., 2000, "pH-independent release of a weakly basic drug from water-insoluble and -soluble matrix tablets," Journal of Controlled Release, 67(1):101-110.

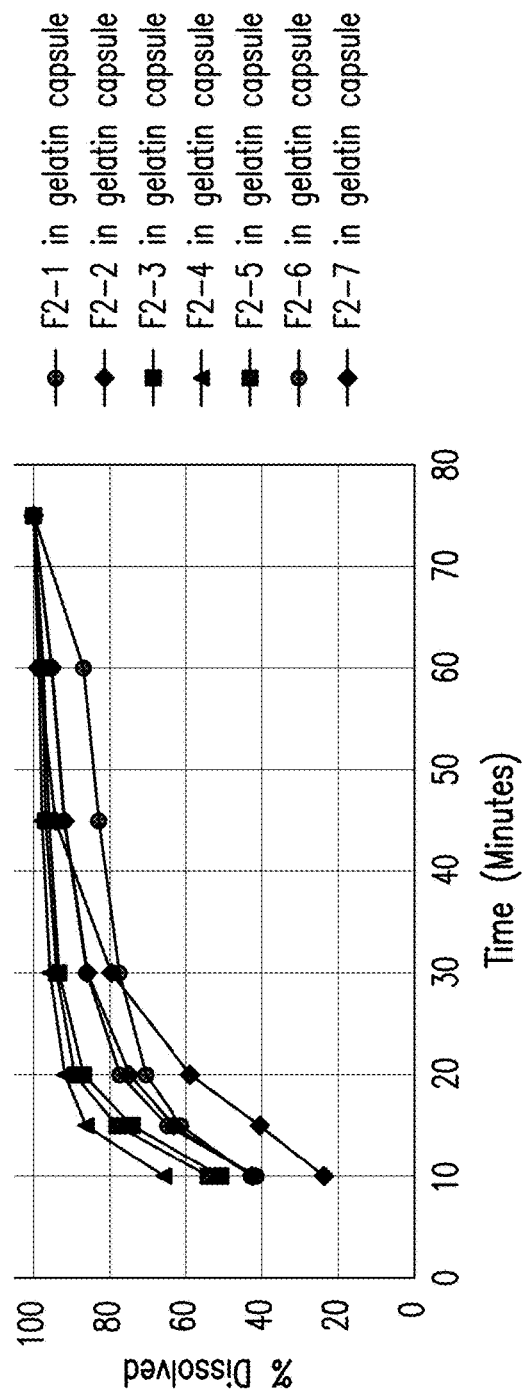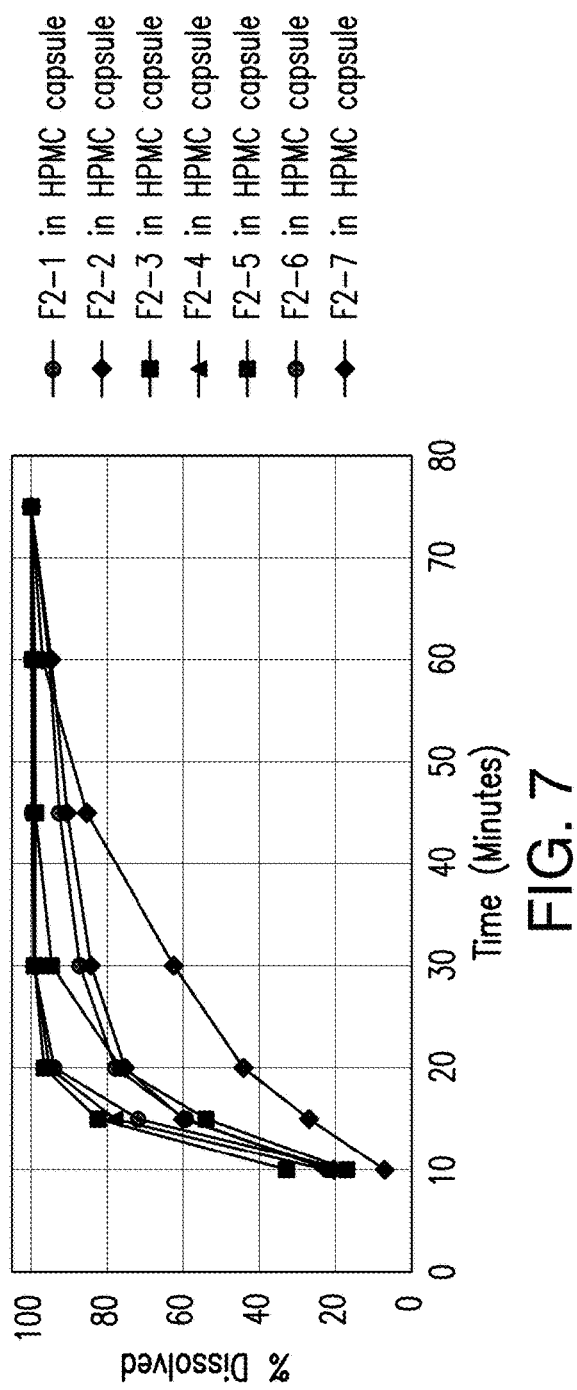

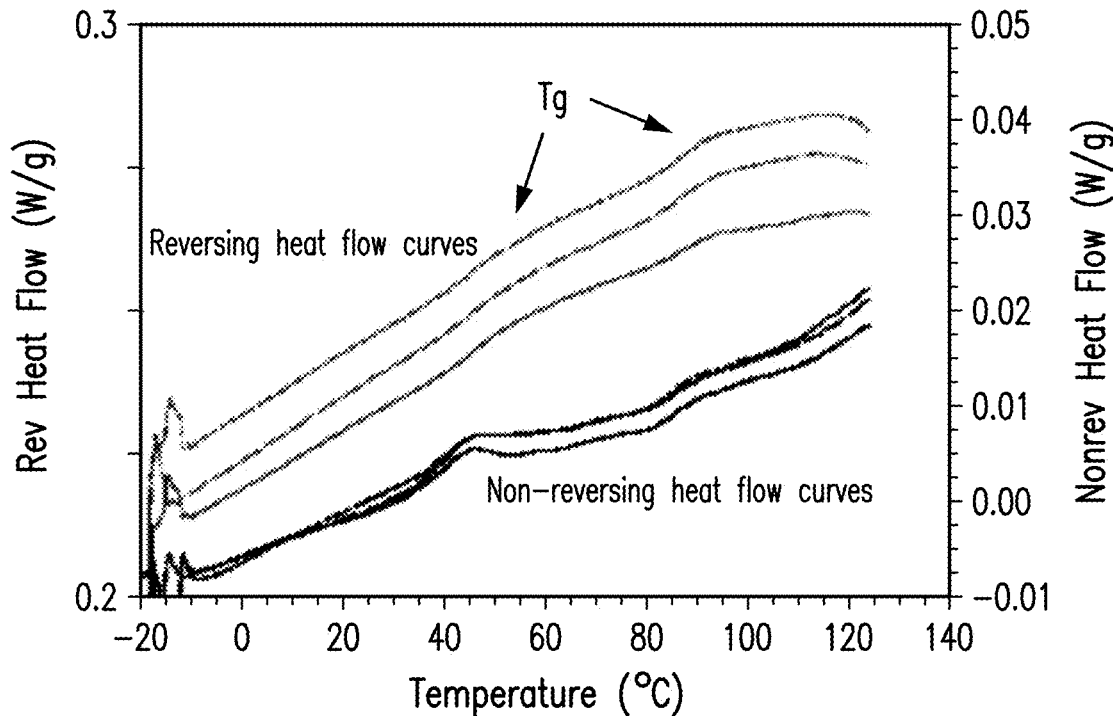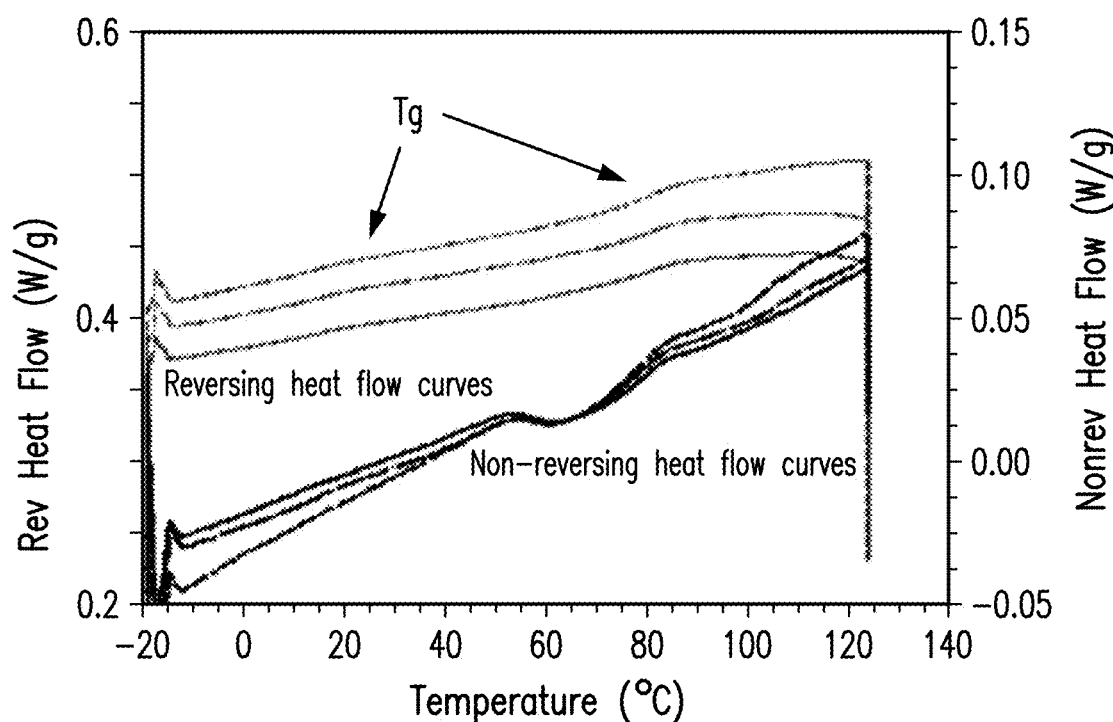
FIG. 41

US 11,701,362 B2

COMPOSITIONS AND METHODS OF USE OF CIS-4-[2-{[(3S,4R)-3-FLUOROOXAN-4-YL]AMINO}-8-(2,4,6-TRICHLOROANILINO)-9H-PURIN-9-YL]-1-METHYLCYCLOHEXANE-1-CARBOXAMIDE

This application is a continuation of U.S. patent application Ser. No. 16/845,195, filed Apr. 10, 2020, currently allowed, which is a continuation of U.S. patent application Ser. No. 16/710,533, filed Dec. 11, 2019, now U.S. Pat. No. 10,653,697, issued May 19, 2020, which is a continuation of U.S. patent application Ser. No. 16/150,350, filed Oct. 3, 2018, now U.S. Pat. No. 10,543,214, issued Jan. 28, 2020, which claims the benefit of U.S. Provisional Application No. 62/568,107, filed Oct. 4, 2017, the entire content of which is incorporated herein by reference.

1. FIELD

Provided are formulations and dosage forms of cis-4-[2-{[(3S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, or a pharmaceutically acceptable salt, tautomer, solvate, hydrate, co-crystal, clathrate, or polymorph thereof, as well as such formulations for use in treating, preventing or managing cancer.

2. BACKGROUND

Cis-4-[2-{[(3S,4R)-3-fluorooxan-4-yl]amino}-8-(2,4,6-trichloroanilino)-9H-purin-9-yl]-1-methylcyclohexane-1-carboxamide or a pharmaceutically acceptable salt, tautomer, solvate, hydrate, co-crystal, clathrate, or polymorph thereof has been shown to have anti-cancer activities. Exemplary methods of use are provided in U.S. Pat. No. 9,512,124 and U.S. Patent Publication No. 2017/0281633. Exemplary polymorphs of cis-4-[2-{[(3S,4R)-3-fluorooxan-4-yl]amino}-8-(2,4,6-trichloroanilino)-9H-purin-9-yl]-1-methylcyclohexane-1-carboxamide are provided in U.S. Publication No. 2017/0281633.

There is a need for further methods of use and formulations of cis-4-[2-{[(3S,4R)-3-fluorooxan-4-yl]amino}-8-(2,4,6-trichloroanilino)-9H-purin-9-yl]-1-methylcyclohexane-1-carboxamide or a pharmaceutically acceptable salt, tautomer, solvate, hydrate, co-crystal, clathrate, or polymorph thereof for the treatment of cancer.

3. BRIEF SUMMARY

In certain embodiments, provided herein is a capsule comprising Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide), or a pharmaceutically acceptable salt, tautomer, solvate, hydrate, co-crystal, clathrate, or polymorph thereof in an amount that is 30-40% of the capsule by weight, an excipient in an amount that is 50-60% of the capsule by weight, and tocophersolan in an amount that is 5-15% of the capsule by weight.

In certain embodiments, provided herein is a capsule comprising 60-70% Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide), or a pharmaceutically acceptable salt, tautomer, solvate, hydrate, co-crystal, clathrate, or polymorph thereof by weight, 20-30% of an excipient by weight, and 5-15% of tocophersolan by weight.

In certain embodiments, provided herein is a capsule comprising 45-55% Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide), or a pharmaceutically acceptable salt, tautomer, solvate, hydrate, co-crystal, clathrate, or polymorph thereof by weight, 35-45% of an excipient by weight, and 5-15% of tocophersolan by weight.

In certain embodiments, provided herein is a capsule comprising 45-55% Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide), or a pharmaceutically acceptable salt, tautomer, solvate, hydrate, co-crystal, clathrate, or polymorph thereof by weight, and 45-55% of an excipient by weight.

In certain embodiments, provided herein is a capsule comprising comprises 0.5-3% of a citrate salt of Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide) by weight, 10-30% microcrystalline cellulose (e.g., Avicel PH102) by weight, 55-75% mannitol (e.g., Parteck M200) by weight, 0.5-3% sodium lauryl sulfate by weight, 2-8% fumaric acid by weight, 1-7% crospovidone by weight, 0.2-1% fumed silica (e.g., AEROSIL 200) by weight, and 0.5-3% magnesium stearate by weight.

In certain embodiments, provided herein is a capsule comprising 2-12% of a citrate salt of Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide) by weight, 10-30% microcrystalline cellulose (e.g., Avicel PH102) by weight, 50-70% mannitol (e.g., Parteck M200) by weight, 0.5-3% sodium lauryl sulfate by weight, 2-8% fumaric acid by weight, 1-7% crospovidone by weight, 0.2-1% fumed silica (e.g., AEROSIL 200) by weight, and 0.5-3% magnesium stearate by weight.

In certain embodiments, provided herein is a capsule comprising 5-20% of a citrate salt of Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide) by weight, 10-30% microcrystalline cellulose (e.g., Avicel PH102) by weight, 50-70% mannitol (e.g., Parteck M200) by weight, 0.5-3% sodium lauryl sulfate by weight, 2-8% fumaric acid by weight, 1-7% crospovidone by weight, 0.2-1% fumed silica (e.g., AEROSIL 200) by weight, and 0.5-3% magnesium stearate by weight.

In certain embodiments, provided herein is a tablet comprising 15-25% of Compound 1 (cis-4-[2-{[(3S,4R)-3-fluorooxan-4-yl]amino}-8-(2,4,6-trichloroanilino)-9H-purin-9-yl]-1-methylcyclohexane-1-carboxamide) or an isotopologue, pharmaceutically acceptable salt, tautomer, solvate, hydrate, co crystal, clathrate, or polymorph thereof by weight, 32-43% of microcrystalline cellulose (e.g., Avicel PH102) by weight, 32-43% of mannitol (e.g., EMPROVE Parteck) by weight, 2-6% of croscarmellose sodium (e.g., Ac-Di-Sol) by weight, 0.3-0.7% of fumed silica (e.g., AEROSIL 200) by weight, and 0.5-1.5% magnesium stearate by weight.

In one embodiment, AEROSIL 200 is a fumed silica with a surface area of about 175 to about 225 $m^2/g$ (e.g., about 200 $m^2/g$). In one embodiment, Ac-Di-Sol is croscarmellose sodium. In one embodiment, EMPROVE Parteck is mannitol.

4. BRIEF DESCRIPTION OF THE DRAWINGS

FIG. 6 shows dissolution profiles of Study 2 formulations in gelatin capsules under dissolution condition 1 in Table 4.

FIG. 7 shows dissolution profiles of Study 2 formulations in HPMC capsules under dissolution condition 1 in Table 4.

FIG. 41 shows the reversible and nonversible heat flow of Capsule A and Capsule H at 75% relative humidity.

5. DETAILED DESCRIPTION

5.1 Definitions

Figure 1:
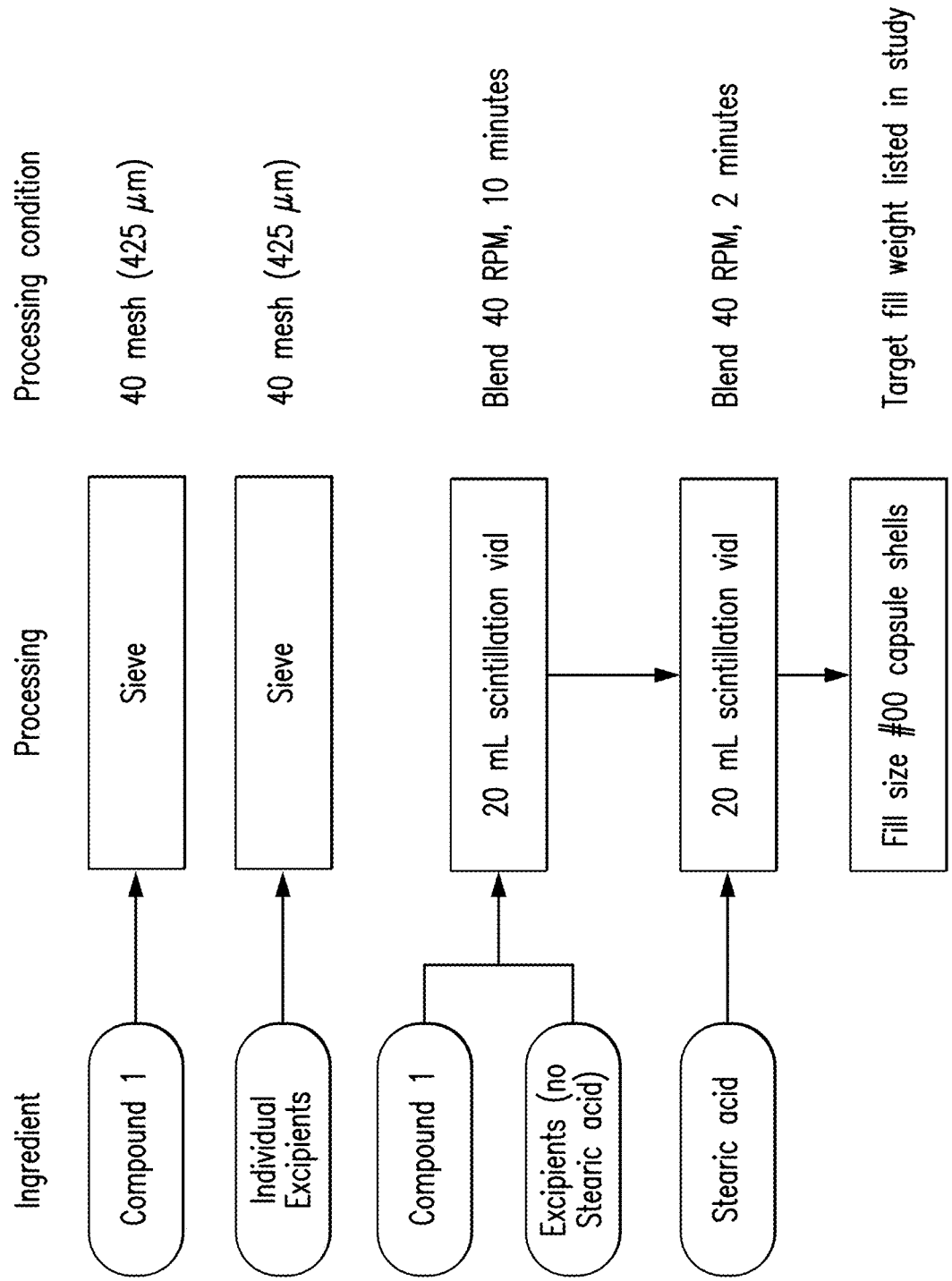
FIG. 1 shows a blending process for preparation of formulations of Compound 1.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term Compound 1 refers to "cis-4-[2-{[(3S,4R)-3-fluorooxan-4-yl]amino}-8-(2,4,6-trichloroanilino)-9H-purin-9-yl]-1-methylcyclohexane-1-carboxamide", alternatively named "(1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide," having the structure:

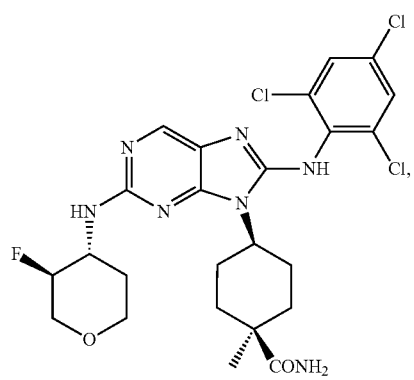 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

and pharmaceutically acceptable salts, tautomers, solvates, hydrates, co-crystals, clathrates, or polymorphs thereof. In certain embodiments, Compound 1 refers to cis-4-[2-{[(3S,4R)-3-fluorooxan-4-yl]amino}-8-(2,4,6-trichloroanilino)-9H-purin-9-yl]-1-methylcyclohexane-1-carboxamide and pharmaceutically acceptable salts, tautomers, solvates, hydrates, co-crystals, clathrates, or polymorphs thereof. In certain embodiments, Compound 1 refers to a polymorph of (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, such as, inter alia, Free Base Forms A-I, Citrate Forms Y and Z, and HCl Salt Forms 1-7, as described in U.S. Publication No. 2017/0283418.

As used herein, unless otherwise specified, the term "pharmaceutically acceptable salt(s)," includes, but is not limited to, salts of acidic or basic moieties of Compound 1. Basic moieties are capable of forming a wide variety of salts with various inorganic and organic acids. The acids that can be used to prepare pharmaceutically acceptable acid addition salts of such basic compounds are those that form non-toxic acid addition salts, e.g., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (e.g., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof that further includes a stoichiometric or non-stoichiometric amount of solvent bound by non-covalent intermolecular forces. Where the solvent is water, the solvate is a hydrate.

A "pharmaceutically acceptable excipient," refers to a substance that aids the administration of an active agent to a subject by for example modifying the stability of an active agent or modifying the absorption by a subject upon administration. A pharmaceutically acceptable excipient typically has no significant adverse toxicological effect on the patient. Examples of pharmaceutically acceptable excipients include, for example, water, NaCl (including salt solutions), normal saline solutions, 2 normal saline, sucrose, glucose, bulking agents, buffers, binders, fillers, disintegrants, lubricants, coatings, sweeteners, flavors, alcohols, oils, gelatins, carbohydrates such as amylose or starch, fatty acid esters, hydroxymethycellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., $6^{th}$ Ed., The Pharmaceutical Press, RPS Publishing (2009). The terms "bulking agent", and "buffer" are used in accordance with the plain and ordinary meaning within the art.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, "administer" or "administration" refers to the act of physically delivering a substance as it exists outside the body into a subject. Administration includes all forms known in the art for delivering therapeutic agents, including but not limited to topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal).

An "effective amount" is an amount sufficient to achieve the effect for which it is administered (e.g., treat a disease or reduce one or more symptoms of a disease or condition). Thus, administration of an "amount" of a compound described herein to a subject refers to administration of "an amount effective," to achieve the desired therapeutic result. A "therapeutically effective amount" of a compound described herein for purposes herein is thus determined by such considerations as are known in the art. The term "therapeutically effective amount" of a composition described herein refers to the amount of the composition that, when administered, is sufficient to treat one or more of the symptoms of a disease described herein (e.g., cancer). Administration of a compound described herein can be determined according to factors such as, for example, the disease state, age, sex, and weight of the individual. A therapeutically effective amount also refers to any toxic or detrimental effects of Compound 1 are outweighed by the therapeutically beneficial effects. Exemplary diseases to be treated are provided in U.S. Pat. No. 9,512,124 and U.S. Patent Publication No. 2017/0281633.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease. Exemplary diseases to be treated are provided in U.S. Pat. No. 9,512,124 and U.S. Patent Publication No. 2017/0281633.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment. Exemplary diseases to be prevented are provided in U.S. Pat. No. 9,512,124 and U.S. Patent Publication No. 2017/0281633.

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission. Exemplary diseases to be managed are provided in U.S. Pat. No. 9,512,124 and U.S. Patent Publication No. 2017/0281633.

The terms "subject," "patient," "subject in need thereof," and "patient in need thereof" are herein used interchangeably and refer to a living organism suffering from one or more of the diseases described herein (e.g., cancer) that can be treated by administration of a composition described herein. Non-limiting examples of organisms include humans, other mammals, bovines, rats, mice, dogs, monkeys, goat, sheep, cows, deer, and other non-mammalian animals. In embodiments, a subject is human. A human subject can be between the ages of about 1 year old to about 100 years old. In embodiments, subjects herein can be characterized by the disease being treated (e.g., a "cancer subject", or a "solid tumor subject"). Exemplary diseases to be treated are provided in U.S. Pat. No. 9,512,124 and U.S. Patent Publication No. 2017/0281633.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

Finally, in general, the technical teaching of one embodiment can be combined with that disclosed in other embodiments provided herein.

5.2 Compound 1

The compound suitable for use in the methods and formulations provided herein is Compound 1: cis-4-[2-{[(3S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide having the structure:

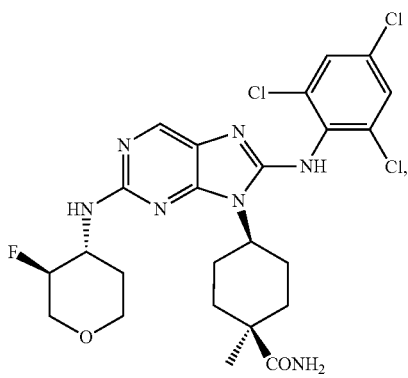 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

or its isotopologues, pharmaceutically acceptable salts, tautomers, solvates, hydrates, co-crystals, clathrates, or polymorphs thereof.

Compound 1 can be prepared according to the methods described in the Examples provided herein or as described in U.S. Pat. No. 9,512,124, the disclosure of which is incorporated herein by reference in its entirety. The compound can be also synthesized according to other methods apparent to those of skill in the art based upon the teaching herein.

In certain embodiments, Compound 1 is a solid. In certain embodiments, Compound 1 is a hydrate. In certain embodiments, Compound 1 is solvated. In certain embodiments, Compound 1 is anhydrous.

In certain embodiments, Compound 1 is amorphous. In certain embodiments, Compound 1 is crystalline. In certain embodiments, Compound 1 is in a crystalline form described in U.S. Publication No. 2017/0283418, which is incorporated herein by reference in its entirety. The solid forms of Compound 1 can be prepared according to the methods described in the disclosure of U.S. Publication No. 2017/0283418. The solid forms can be also prepared according to other methods apparent to those of skill in the art.

In one aspect, provided herein are stable formulations of Compound 1. In one embodiment, the formulations of Compound 1 comprise a solid form of cis-4-[2-{[(3S,4R)-3-fluorooxan-4-yl]amino}-8-(2,4,6-trichloroanilino)-9H-purin-9-yl]-1-methylcyclohexane-1-carboxamide. In one embodiment, the formulations of Compound 1 comprise an amorphous form of cis-4-[2-{[(3S,4R)-3-fluorooxan-4-yl]amino}-8-(2,4,6-trichloroanilino)-9H-purin-9-yl]-1-methylcyclohexane-1-carboxamide. In one embodiment, the formulations of Compound 1 comprise a crystalline form of cis-4-[2-{[(3S,4R)-3-fluorooxan-4-yl]amino}-8-(2,4,6-trichloroanilino)-9H-purin-9-yl]-1-methylcyclohexane-1-carboxamide.

Formulations provided herein may be used in the preparation of individual, single unit dosage forms. Formulations and dosage forms provided herein comprise Compound 1. Formulations and dosage forms can further comprise one or more excipients.

The formulations provided herein for oral administration can be provided as compressed capsules, tablets, tablet triturates, chewable lozenges, rapidly dissolving tablets, multiple compressed tablets, or enteric-coating tablets, sugar-coated, or film-coated tablets, but are not limited thereto.

5.2.1 Citrate Salt Form Y

Also provided herein are solid forms of Compound 1 that include citrate salts.

In certain embodiments, provided herein is citrate salt Form Y.

In one embodiment, the citrate salt Form Y is a solid form of Compound 1. In another embodiment, the citrate salt Form Y is crystalline. In another embodiment, the citrate salt Form Y is an anhydrate.

In certain embodiments, a solid form provided herein, e.g., Form Y is a citrate salt of Compound 1, and is substantially crystalline, as indicated by, e.g., X-ray powder diffraction measurements. In one embodiment, a solid form provided herein, e.g., Form Y, has one or more characteristic X-ray powder diffraction peaks at approximately 4.8, 6.6, 9.6, 13.6, 14.4, 15.4, 16.0, 16.9, 18.0, 18.9, 19.2, 19.9, 20.1, 20.9, 21.8, 22.4, 22.7, 23.2, 23.4, 24.0, 24.1, 24.3, 25.1, 26.7, 27.0, 27.9, 28.5, 29.0, 29.6, 30.2, 30.4, 30.8, 31.1, 31.6, 32.3, 33.1, 33.5, 34.0, 34.6, or 35.1° 2θ (0.2° 2θ) or (0.1° 2θ). In a specific embodiment, a solid form provided herein, e.g., Form Y, has one, two, three, four, five, six, seven, eight, nine, ten, or eleven characteristic X-ray powder diffraction peaks at approximately 4.8, 6.6, 9.6, 15.4, 16.0, 16.9, 18.9, 19.2, 19.9, 20.9, or 28.5° 2θ (0.2° 2θ). In another embodiment, a solid form provided herein has one, two, three, or four characteristic X-ray powder diffraction peaks at approximately 4.8, 9.6, 18.9, or 19.2° 2θ (0.2° 2θ). In one embodiment, the solid form is citrate salt Form Y. In another embodiment, the citrate salt Form Y has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, or forty characteristic X-ray powder diffraction peaks.

In certain embodiments, the crystalline form exhibits a TGA thermogram comprising a total mass loss of approximately 0.1% of the total mass of the sample between approximately 50° C. and approximately 150° C. when heated from approximately 50° C. to approximately 220° C.

In one embodiment, provided herein is a crystalline citrate salt of Compound 1 having a DSC thermogram comprising an endothermic event with an onset temperature of about 213° C. and a peak maximum temperature at about 217° C. when heated from approximately 25° C. to approximately 260° C.

In still another embodiment, the citrate salt Form Y is substantially pure. In certain embodiments, the substantially pure citrate salt Form Y is substantially free of other solid forms, e.g., amorphous solid. In certain embodiments, the purity of the substantially pure citrate salt Form Y is no less than about 95%, no less than about 96%, no less than about 97%, no less than about 98%, no less than about 98.5%, no less than about 99%, no less than about 99.5%, or no less than about 99.8%.

5.2.2 Citrate Salt Form Z

In certain embodiments, provided herein is a citrate salt Form Z.

In one embodiment, the citrate salt Form Z is a solid form of Compound 1. In another embodiment, the citrate salt Form Z is crystalline. In another embodiment, the citrate salt Form Z is an anhydrate. In another embodiment, the citrate salt Form Z is a hydrate. In one embodiment, the citrate salt Form Z is a non-stoichiometric hydrate. In still another embodiment, the citrate salt Form Z is a channel hydrate. In still another embodiment, the citrate salt Form Z is a non-stoichiometric channel hydrate. In still another embodiment, the citrate salt Form Z is a solvate.

In certain embodiments, a solid form provided herein, e.g., Form Z, is substantially crystalline, as indicated by, e.g., X-ray powder diffraction measurements. In one embodiment, a solid form provided herein, e.g., Form Z, has one or more characteristic X-ray powder diffraction peaks at approximately 4.6, 6.6, 9.4, 13.1, 14.1, 15.3, 15.6, 17.4, 18.8, 19.0, 19.9, 20.4, 21.1, 21.9, 22.2, 22.7, 23.5, 23.9, 25.2, 26.3, 26.8, 27.8, 28.3, 28.7, 29.8, 31.2, 31.9, 32.6, 33.7, 35.1, 35.9, 37.4, or 38.0° 2θ (0.2° 2θ) or (0.1° 2θ). In a specific embodiment, a solid form provided herein has one, two, three, or four characteristic X-ray powder diffraction peaks at approximately 9.4, 18.8, 19.0, or 28.7° 2θ (0.2° 2θ). In one embodiment, the solid form is citrate salt Form Z. In another embodiment, the citrate salt Form Z has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, or thirty-three characteristic X-ray powder diffraction peaks.

In certain embodiments, the crystalline form exhibits a TGA thermogram comprising a total mass loss of approximately 0.1% of the total mass of the sample between approximately 50° C. and approximately 150° C. when heated from approximately 25° C. to approximately 300° C. In certain embodiments, the crystalline form is an anhydrate of Compound 1.

In one embodiment, provided herein is a crystalline citrate salt Form of Compound 1 having a DSC thermogram comprising an endothermic event with an onset temperature at about 217° C. and a peak maximum temperature at about 221° C. when heated from approximately 25° C. to approximately 260° C.

In certain embodiments, the hydrate exhibits a TGA thermogram comprising a total mass loss of approximately 2% of the total mass of the sample between approximately 25° C. and approximately 200° C. when heated from approximately 25° C. to approximately 300° C. In certain embodiments, the crystalline form is a hydrate of the Citrate form of Compound 1.

In certain embodiments, the non-stoichiometric hydrate form exhibits a TGA thermogram comprising a total mass loss of approximately 1.7% of the total mass of the sample between approximately 50° C. and approximately 200° C. when heated from approximately 50° C. to approximately 300° C. In certain embodiments, the crystalline form is a non-stoichiometric hydrate of the Citrate form of Compound 1.

In certain embodiments, the solvate exhibits a TGA thermogram comprising a total mass loss of approximately 1.3% of the total mass of the sample between approximately 25° C. and approximately 200° C. when heated from approximately 25° C. to approximately 300° C. In certain embodiments, the crystalline form is a solvate of the Citrate form of Compound 1.

In still another embodiment, the citrate salt Form Z is substantially pure. In certain embodiments, the substantially pure citrate salt Form Z is substantially free of other solid forms, e.g., amorphous solid. In certain embodiments, the purity of the substantially pure citrate salt Form Z is no less than about 95%, no less than about 96%, no less than about 97%, no less than about 98%, no less than about 98.5%, no less than about 99%, no less than about 99.5%, or no less than about 99.8%.

Form Y and Form Z of the citrate salt of Compound 1 can be prepared according to the methods described in the Examples provided herein or as described in U.S. Publication No. 2017/0283418 A1, the disclosure of which is incorporated herein by reference in its entirety. The solid forms can be also synthesized according to other methods apparent to those of skill in the art based upon the teaching herein.

5.2.3 Capsules

Provided herein are capsules comprising Compound 1. In certain embodiments, the capsule comprises a citrate salt of Compound 1. In another embodiment, the capsule comprises a citrate salt of Compound 1 and sodium lauryl sulfate.

In one embodiment, a capsule comprises Compound 1. In one embodiment, the capsule comprises an excipient. In one embodiment, the capsule comprises tocophersolan ("TPGS"). In certain embodiments, the capsule comprises 20-30%, 30%-40%, 40%-50%, or 50%-60% Compound 1 by weight. In certain embodiments, the capsule comprises 35-45%, 45%-55%, or 55%-65% excipient by weight. In certain embodiments, the capsule comprises 5-15% TPSG by weight. In certain embodiments, the capsule comprises 20-30% Compound 1 by weight, 60-70% excipient by weight, and 5-15% TPGS by weight. In certain embodiments, the capsule comprises 45-55% Compound 1 by weight, 35-45% excipient by weight, and 5-15% TPGS by weight. In certain embodiments, the capsule comprises 45-55% of Compound 1 by weight and 45-55% of excipient by weight. In certain embodiments, the excipient is hydroxypropyl methylcellulose ("HPMC"). In certain embodiments, the excipient is polyvinlylacetate phthalate polymer ("PVA-P"). In certain embodiments, the excipient is vinylpyrrolidone-vinyl acetate copolymer ("PVP VA64").

In certain embodiments, provided herein is a capsule formulation comprising 35-45% Compound 1 by weight, 50-60% HPMC by weight, and 5-15% TPGS by weight. In certain embodiments, the capsule comprises 37% Compound 1 by weight, 53% HPMC by weight, and 10% TPGS by weight.

In certain embodiments, provided herein is a capsule formulation comprising 20-30% Compound 1 by weight, 60-70% HPMC by weight, and 5-15% TPGS by weight. In certain embodiments, the capsule comprises 25% Compound 1 by weight, 65% HPMC by weight, and 10% TPGS by weight.

In certain embodiments, provided herein is a capsule formulation comprising 20-30% Compound 1 by weight, 60-70% PVA-P by weight, and 5-15% TPGS by weight. In certain embodiments, the capsule comprises 25% Compound 1 by weight, 65% PVA-P by weight, and 10% TPGS by weight.

In certain embodiments, provided herein is a capsule formulation comprising 20-30% Compound 1 by weight, 60-70% PVP V64 by weight, and 5-15% TPGS by weight.

In certain embodiments, the capsule comprises 25% Compound 1 by weight, 65% PVP VA64 by weight, and 10% TPGS by weight.

In certain embodiments, provided herein is a capsule formulation comprising 45-55% Compound 1 by weight, 35-45% HPMC by weight, and 5-15% TPGS by weight. In certain embodiments, the capsule comprises 50% Compound 1 by weight, 40% HPMC by weight, and 10% TPGS by weight.

In certain embodiments, provided herein is a capsule formulation comprising 45-55% Compound 1 by weight, 35-45% PVA-P by weight, and 5-15% TPGS by weight. In certain embodiments, the capsule comprises 50% Compound 1 by weight, 40% PVA-P by weight, and 10% TPGS by weight.

In certain embodiments, provided herein is a capsule formulation comprising 45-55% Compound 1 by weight, 35-45% PVP VA64 by weight, and 5-15% TPGS by weight. In certain embodiments, the capsule comprises 50% Compound 1 by weight, 40% PVP VA64 by weight, and 10% TPGS by weight.

In certain embodiments, provided herein is a capsule formulation comprising 45-55% Compound 1 by weight and 45-55% HPMC by weight. In certain embodiments, the capsule comprises 50% Compound 1 by weight and 50% HPMC by weight.

In certain embodiments, provided herein is a capsule formulation comprising 45-55% Compound 1 by weight and 45-55% PVA-P by weight. In certain embodiments, the capsule comprises 50% Compound 1 by weight and 50% PVA-P by weight.

In certain embodiments, provided herein is a capsule formulation comprising an amount of Compound 1 in gelatin capsules. In certain embodiments, the amount of Compound 1 is 100-150 mg. In certain embodiments, the amount of Compound 1 is 125 mg.

In certain embodiments, provided herein is a capsule formulation comprising an amount of Compound 1 in HPMC capsules. In certain embodiments, the amount of Compound 1 is 100-150 mg. In certain embodiments, the amount of Compound 1 is 125 mg.

In certain embodiments, provided herein is a capsule formulation comprising Compound 1 and microcrystalline cellulose (Avicel) in a gelatin capsule. In certain embodiments, the capsule further comprises sodium laureth sulfate. In certain embodiments, Compound 1 and Avicel are present in the capsule in a 2:1 ratio. In certain embodiments, the total weight of Compound 1 and Avicel is between 100-120 mg. In certain embodiments, the total weight of Compound 1 and Avicel is 110 mg.

In certain embodiments, the capsule comprises a citrate salt of Compound 1, microcrystalline cellulose (e.g., Avicel PH102), mannitol (e.g., Parteck M200), citric acid; sodium lauryl sulfate, crosslinked polyvinylpyrrolidone (e.g., Kollidon CL), colloidal silicon dioxide, and stearic acid. In certain embodiments, the capsule comprises 5-25% of a citrate salt of Compound 1 by weight, 15-60% microcrystalline cellulose (e.g., Avicel PH102) by weight, 15-60% mannitol (e.g., Parteck M200) by weight, 5-20% citric acid by weight; 2.5-10% sodium lauryl sulfate by weight, 2-8% crosslinked polyvinylpyrrolidone (e.g., Kollidon CL) by weight, 0.3-1.5% colloidal silicon dioxide by weight, and 0.5-2% stearic acid by weight. In certain embodiments, the capsule comprises about 13.36% of a citrate salt of Compound 1 by weight, about 33.02% microcrystalline cellulose (e.g., Avicel PH102) by weight, about 33.02% mannitol (e.g., Parteck M200) by weight, about 10% citric acid by weight; about 5% sodium lauryl sulfate by weight, about 4% crosslinked polyvinylpyrrolidone (e.g., Kollidon CL) by weight, about 0.6% colloidal silicon dioxide by weight, and about 1% stearic acid by weight. In certain embodiments, the capsule comprises 5-25% of a citrate salt of Compound 1 by weight and 2.5-10% sodium lauryl sulfate by weight. In certain embodiments, the capsule comprises about 13.36% of a citrate salt of Compound 1 by weight and about 5% sodium lauryl sulfate by weight.

In certain embodiments, the capsule comprises a citrate salt of Compound 1 and sodium lauryl sulfate. In certain embodiments, the capsule comprises 0.5-3% of a citrate salt of Compound 1 by weight and 0.5-3% sodium lauryl sulfate by weight. In certain embodiments, the capsule comprises about 1.79% of a citrate salt of Compound 1 by weight and about 1.0% sodium lauryl sulfate by weight. In certain embodiments, the capsule comprises 2-12% of a citrate salt of Compound 1 by weight and 0.5-3% sodium lauryl sulfate by weight. In certain embodiments, the capsule comprises about 6.70% of a citrate salt of Compound 1 by weight and about 1.0% sodium lauryl sulfate by weight. In certain embodiments, the capsule comprises 5-20% of a citrate salt of Compound 1 by weight and 0.5-3% sodium lauryl sulfate by weight. In certain embodiments, the capsule comprises about 10.72% of a citrate salt of Compound 1 by weight and about 1.0% sodium lauryl sulfate by weight.

In certain embodiments, the capsule comprises a citrate salt of Compound 1, microcrystalline cellulose (e.g., Avicel PH102), Mannitol (e.g., Parteck M200), sodium lauryl sulfate, fumaric acid, crospovidone, fumed silica (e.g., Aerosil 200), and magnesium stearate. In certain embodiments, the capsule comprises 0.5-3% of a citrate salt of Compound 1 by weight, 10-30% microcrystalline cellulose (e.g., Avicel PH102) by weight, 55-75% mannitol (e.g., Parteck M200) by weight, 0.5-3% sodium lauryl sulfate by weight, 2-8% fumaric acid by weight, 1-7% crospovidone by weight, 0.2-1% aerosol 200 by weight, and 0.5-3% magnesium stearate by weight. In certain embodiments, the capsule comprises about 1.79% of a citrate salt of Compound 1 by weight, about 21.65% microcrystalline cellulose (e.g., Avicel PH102) by weight, about 64.96% mannitol (e.g., Parteck M200) by weight, about 1.0% sodium lauryl sulfate by weight, about 5.0% fumaric acid by weight, about 4.0% crospovidone by weight, about 0.6% fumed silica (e.g., Aerosil 200) by weight, and about 1.0% magnesium stearate by weight. In certain embodiments, the capsule comprises 0.5-3% of a citrate salt of Compound 1 by weight and 0.5-3% sodium lauryl sulfate by weight. In certain embodiments, the capsule comprises about 1.79% of a citrate salt of Compound 1 by weight and about 1.0% sodium lauryl sulfate by weight.

In certain embodiments, the capsule comprises 2-12% of a citrate salt of Compound 1 by weight, 10-30% microcrystalline cellulose (e.g., Avicel PH102) by weight, 50-70% mannitol (e.g., Parteck M200) by weight, 0.5-3% sodium lauryl sulfate by weight, 2-8% fumaric acid by weight, 1-7% crospovidone by weight, 0.2-1% fumed silica (e.g., Aerosil 200) by weight, and 0.5-3% magnesium stearate by weight. In certain embodiments, the capsule comprises about 6.70% of a citrate salt of Compound 1 by weight, about 20.42% microcrystalline cellulose (e.g., Avicel PH102) by weight, about 61.28% mannitol (e.g., Parteck M200) by weight, about 1.0% sodium lauryl sulfate by weight, about 5.0% fumaric acid by weight, about 4.0% crospovidone by weight, about 0.6% fumed silica (e.g., Aerosil 200) by weight, and about 1.0% magnesium stearate by weight. In certain embodiments, the capsule comprises 2-12% of a citrate salt of Compound 1 by weight and 0.5-3% sodium lauryl sulfate by weight. In certain embodiments, the capsule comprises about 6.70% of a citrate salt of Compound 1 by weight and about 1.0% sodium lauryl sulfate by weight.

In certain embodiments, the capsule comprises 5-20% of a citrate salt of Compound 1 by weight, 10-30% microcrystalline cellulose (e.g., Avicel PH102) by weight, 50-70% mannitol (e.g., Parteck M200) by weight, 0.5-3% sodium lauryl sulfate by weight, 2-8% fumaric acid by weight, 1-7% crospovidone by weight, 0.2-1% fumed silica (e.g., Aerosil 200) by weight, and 0.5-3% magnesium stearate by weight. In certain embodiments, the capsule comprises about 10.72% of a citrate salt of Compound 1 by weight, about 19.41% microcrystalline cellulose (e.g., Avicel PH102) by weight, about 58.27% mannitol (e.g., Parteck M200) by weight, about 1.0% sodium lauryl sulfate by weight, about 5.0% fumaric acid by weight, about 4.0% crospovidone by weight, about 0.6% fumed silica (e.g., Aerosil 200) by weight, and about 1.0% magnesium stearate by weight. In certain embodiments, the capsule comprises 5-20% of a citrate salt of Compound 1 by weight and 0.5-3% sodium lauryl sulfate by weight. In certain embodiments, the capsule comprises about 10.72% of a citrate salt of Compound 1 by weight and about 1.0% sodium lauryl sulfate by weight.

5.2.4 Tablets

Provided herein are tablets comprising Compound 1. In certain embodiments, Compound 1 is an HCl salt. In certain embodiments, Compound 1 is a citrate salt.

In certain embodiments, provided herein is a tablet comprising Compound 1 and a filler, disintegrant, lubricant, acidifier, surfactant, polymer, and/or glidant. In certain embodiments, the filler is microcrystalline cellulose (e.g., Avicel PH102), mannitol, lactose, or starch. In certain embodiments, the disintegrant is croscarmellose sodium (e.g., Ac-Di-sol), sodium starch glycolate, or Kollidon CL. In certain embodiments, the lubricant is magnesium stearate, stearic acid, or sodium stearyl fumarate. In certain embodiments, the acidifier is tartaric acid, fumaric acid, or citric acid. In certain embodiments, the surfactant is sodium lauryth sulfate, VE-TPGS, or hydrogenated Castor Oil. In certain embodiments, the polymer is HEC, HPC, PEG4000, PVP K30, Pluronic F127, PVP VA64, or SB-beta-CD. In certain embodiments, the glidant is aerosol 200. In certain embodiments, the ratio of Compound 1 to filler is about 1:5. In certain embodiment, the ratio of Compound 1 to disintegrant is about 2:1. In certain embodiments, the ratio of Compound 1 to lubricant is about 20:1. In certain embodiments, the ratio of Compound 1 to acidifier is about 1:1. In certain embodiments, the ratio of Compound 1 to surfactant is about 20:1. In certain embodiments, the ratio of Compound 1 to polymer is about 1:2. In certain embodiments, the ratio of Compound 1 to glidant is about 20:1.

In certain embodiments, provided herein is a tablet comprising 15-25% of Compound 1 by weight, 32-43% of microcrystalline cellulose (e.g., Avicel PH102) by weight, 32-43% of mannitol (e.g., Emprove Parteck) by weight, 2-6% of croscarmellose sodium (e.g., Ac-Di-Sol) by weight, 0.3-0.7% of fumed silica (e.g., Aerosil 200) by weight, and 0.5-1.5% magnesium stearate by weight. In certain embodiments, the tablet comprises 20% of Compound 1 by weight, 37.25% of microcrystalline cellulose (e.g., Avicel PH102) by weight, 37.25% of mannitol (e.g., Emprove Parteck) by weight, 4% of croscarmellose sodium (e.g., Ac-Di-Sol) by weight, 0.5% of fumed silica (e.g., Aerosil 200) by weight, and 1% magnesium stearate by weight. In certain embodiments, the total weight of the tablet is between 225-275 mg. In certain embodiments, the total weight of the tablet is 250 mg. In certain embodiments, Compound 1 is an HCl salt. In certain embodiments, Compound 1 is a citrate salt.

In certain embodiments, provided herein is a tablet comprising 15-25% of Compound 1 by weight, 32-43% of microcrystalline cellulose (e.g., Avicel PH102) by weight, 32-43% of mannitol (e.g., Emprove Parteck) by weight, 2-6% of croscarmellose sodium (e.g., Ac-Di-Sol) by weight, 0.3-0.7% of fumed silica (e.g., Aerosil 200) by weight, and 0.5-1.5% magnesium stearate by weight. In certain embodiments, the tablet comprises 20% of Compound 1, 37.25% of microcrystalline cellulose (e.g., Avicel PH102) by weight, 37.25% of mannitol (e.g., Emprove Parteck) by weight, 4% of croscarmellose sodium (e.g., Ac-Di-Sol) by weight, 0.5% of fumed silica (e.g., Aerosil 200) by weight, and 1% magnesium stearate by weight. In certain embodiments, the total weight of the tablet is between 225-275 mg. In certain embodiments, the total weight of the tablet is 250 mg.

In certain embodiments, provided herein is a tablet comprising 15-25% of an HCl salt of Compound 1 by weight, 32-43% of microcrystalline cellulose (e.g., Avicel PH102) by weight, 32-43% of mannitol (e.g., Emprove Parteck) by weight, 2-6% of croscarmellose sodium (e.g., Ac-Di-Sol) by weight, 0.3-0.7% of fumed silica (e.g., Aerosil 200) by weight, and 0.5-1.5% magnesium stearate by weight. In certain embodiments, the tablet comprises 20% of a HCl salt of Compound 1 by weight, 37.25% of microcrystalline cellulose (e.g., Avicel PH102) by weight, 37.25% of mannitol (e.g., Emprove Parteck) by weight, 4% of croscarmellose sodium (e.g., Ac-Di-Sol) by weight, 0.5% of fumed silica (e.g., Aerosil 200) by weight, and 1% magnesium stearate by weight. In certain embodiments, the total weight of the tablet is between 225-275 mg. In certain embodiments, the total weight of the tablet is 250 mg.

In certain embodiments, provided herein is a tablet comprising 15-25% of a citrate salt of Compound 1 by weight, 32-43% of microcrystalline cellulose (e.g., Avicel PH102) by weight, 32-43% of mannitol (e.g., Emprove Parteck) by weight, 2-6% of croscarmellose sodium (e.g., Ac-Di-Sol) by weight, 0.3-0.7% of fumed silica (e.g., Aerosil 200) by weight, and 0.5-1.5% magnesium stearate by weight. In certain embodiments, the tablet comprises 20% of a citrate salt of Compound 1 by weight, 37.25% of microcrystalline cellulose (e.g., Avicel PH102) by weight, 37.25% of mannitol (e.g., Emprove Parteck) by weight, 4% of croscarmellose sodium (e.g., Ac-Di-Sol) by weight, 0.5% of fumed silica (e.g., Aerosil 200) by weight, and 1% magnesium stearate by weight. In certain embodiments, the total weight of the tablet is between 225-275 mg. In certain embodiments, the total weight of the tablet is 250 mg.

5.2.5 Spray Dried Dispersion Formulation

In certain embodiments, provided herein is a spray dried dispersion formulation of Compound 1.

Figure 60:
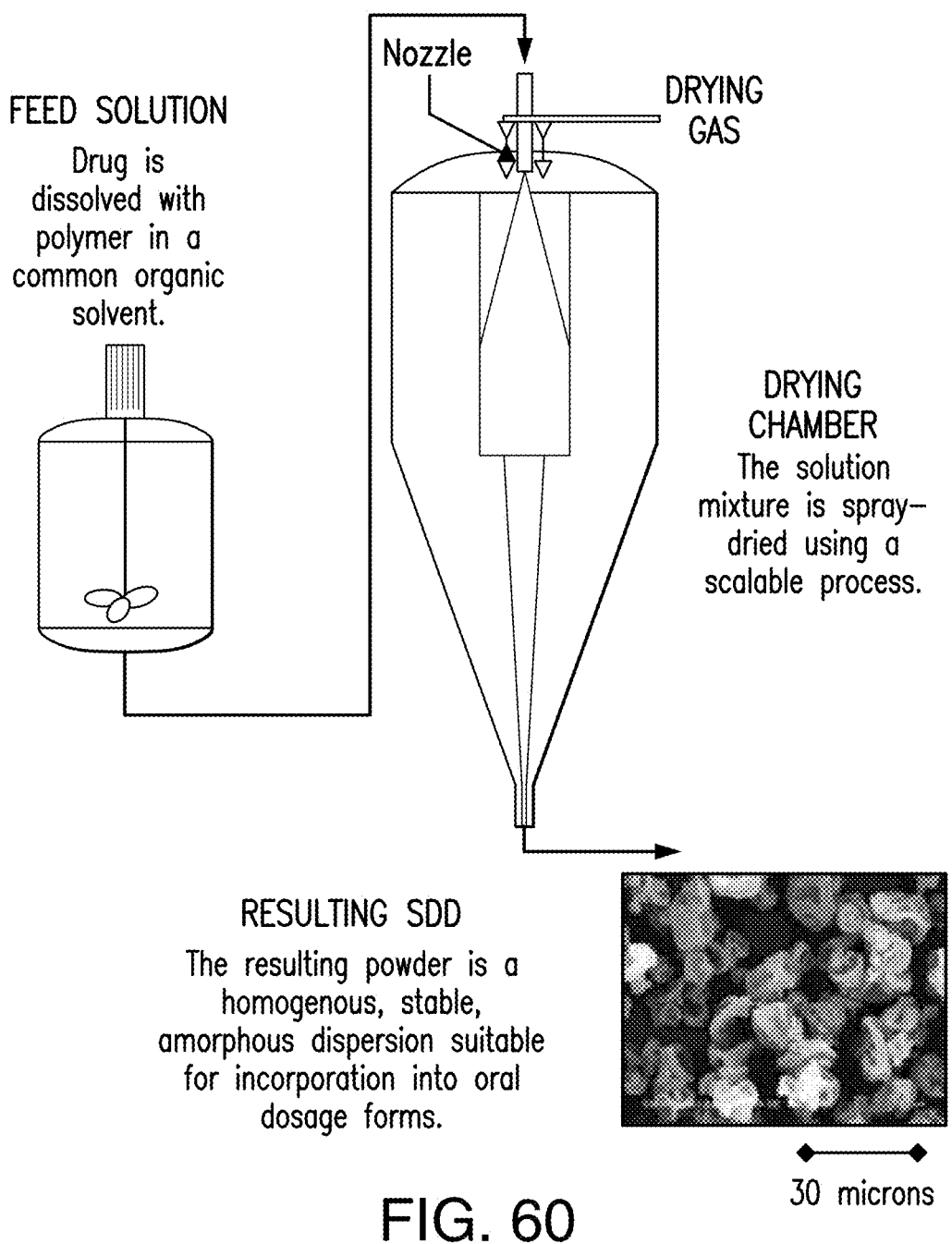
FIG. 60 shows a spray-drying process providing the spray dried dispersion formulation of Compound 1.

In certain embodiments, the spray dried dispersion formulation provided herein can be obtained by a spray-drying process of Compound 1 substantially as shown in FIG. 60. In certain embodiments, the spray-drying process comprises 1) mixing Compound 1 and an excipient with a solvent (e.g., acetone, methanol, water or a mixture thereof); 2) heating the mixture to a certain temperature (e.g., about 80° C.); 3) spray-drying the mixture; and 4) collecting resulting solids. In certain embodiments, the excipient is a polymer. In another embodiment, the excipient is a polymer selected from a group consisting of HPMCAS-M, PVP VA64, PVA-P and HPMC E3. In one embodiment, the solvent is acetone. In another embodiment, the solvent is a mixture of methanol and water (e.g., v/v 9:1) or a mixture of acetone and water (e.g., v/v 9:1).

In certain embodiments, the spray dried dispersion formulation comprises Compound 1 free base, HPMC, TPGS, microcrystalline cellulose (e.g., Avicel PH102), mannitol, crosslinked polyvinylpyrrolidone (e.g., Kollidon CL), colloidal silicon dioxide, and stearic acid. In certain embodiments, the spray dried dispersion formulation comprises about 10-40% of Compound 1 free base by weight, about 15-60% HPMC by weight, about 2-10% TPGS by weight, about 10-40% microcrystalline cellulose (e.g., Avicel PH102) by weight, about 10-40% mannitol by weight, about 2-8% crosslinked polyvinylpyrrolidone (e.g., Kollidon CL) by weight, about 0.3-1.5% colloidal silicon dioxide by weight, and about 0.5-2% stearic acid by weight. In certain embodiments, the spray dried dispersion formulation comprises about 20% of Compound 1 free base by weight, about 28.6% HPMC by weight, about 5.4% TPGS by weight, about 20.2% microcrystalline cellulose (e.g., Avicel PH102) by weight, about 20.2% mannitol by weight, about 4% crosslinked polyvinylpyrrolidone (e.g., Kollidon CL) by weight, about 0.6% colloidal silicon dioxide by weight, and about 1% stearic acid by weight.

5.3 Kits

Pharmaceutical packs or kits which comprise pharmaceutical compositions or dosage forms provided herein are also provided. Exemplary kits include notice in the form prescribed by a governmental agency regulating the manufacture, use or sale of pharmaceuticals products, which notice reflects approval by the agency of manufacture, use or sale for human administration.

5.4 Methods of Use

The formulations of Compound 1 described herein have utility as pharmaceuticals to treat, prevent or improve conditions in animals or humans. Accordingly, provided herein are formulations of Compound 1 described herein that can be used in all the methods as provided herein. Particularly, the formulations of Compound 1 as provided herein are for uses in methods for the treatment or prevention of a cancer. For example, the formulations of Compound 1 as provided herein are for uses in methods for the treatment of a cancer. The methods provided herein comprise the administration of an effective amount of one or more formulations of Compound 1 described herein to a subject in need thereof. It is to be understood that the methods described herein also include treatment with a pharmaceutical composition, such as those provided below.

In another aspect, provided herein are methods for treating or preventing a cancer, comprising administering to a subject in need thereof an effective amount of a formulation of Compound 1, as described herein. In some embodiments, the cancer is a solid tumor or a hematological tumor. In some embodiments, the cancer is not melanoma.

In some embodiments, the solid tumor is melanoma, colorectal cancer, stomach cancer, head and neck cancer, thyroid cancer, bladder cancer, CNS cancer, lung cancer, pancreatic cancer, and soft tissue cancer. In one embodiment, the solid tumor is endocrine cancer, bladder cancer, breast cancer, cervix cancer, colon cancer, duodenum cancer, glioma, head and d neck cancer, kidney cancer, liver cancer, lung cancer (e.g. non-small cell lung cancer NSCLC), esophageal cancer, thyroid cancer, or pancreatic cancer.

In other embodiments, the cancer is bladder cancer, breast cancer (for example Her positive, Her negative, or EGFR positive breast cancer), CNS cancer (including neuroblastoma, and glioma), colon cancer, gastrointestinal cancer (for example, stomach cancer, and colon cancer), endocrine cancer (for example, thyroid cancer, or adrenal gland cancer), female genitoureal cancer (for example, cervix cancer, ovary clear cell cancer, vulva cancer, uterus cancer, or ovary cancer), head and neck cancer, hematopoietic cancer (for example, leukemia or myeloma), kidney cancer, liver cancer, lung cancer (for example, NSCLC, or SCLC), melanoma, pancreas cancer, prostate cancer, or soft tissue cancer (for example, sarcoma, or osteosarcoma).

Also provided herein are methods for treating or preventing hepatocellular carcinoma (HCC), comprising administering to a subject in need thereof an effective amount of a formulation of Compound 1, as described herein.

Also provided herein are methods for treating or preventing colorectal cancer (CRC), melanoma, gastric cancer, HCC, lung cancer, pancreatic cancer, leukemia, or multiple myeloma, comprising administering to a subject in need thereof an effective amount of a formulation of Compound 1 as described herein or a pharmaceutical composition thereof, as described herein. In one embodiment, the CRC, gastric cancer, or HCC is a cancer characterized by a β-catenin mutation. Also provided herein are methods for treating or preventing colorectal cancer (CRC), gastric cancer, HCC, lung cancer, pancreatic cancer, leukemia, and multiple myeloma, comprising administering to a subject in need thereof an effective amount of a formulation of Compound 1 as described herein, as described herein.

In another embodiment provided herein are methods of treating leukemia comprising administering a formulation of Compound 1 as described herein or a pharmaceutical composition thereof. The leukemia can be chronic myelogenous leukemia (CML). In another embodiment, the leukemia is acute myelogenous leukemia (AML). In one embodiment, the leukemia is FLT-3 mutated AML.

In another embodiment provided herein are methods of treating lymphoma comprising administering a formulation of Compound 1 as described herein or a pharmaceutical composition thereof. The lymphoma can be Burkitt's lymphoma. In one embodiment, the leukemia is Hodgkin's lymphoma. In another embodiment, the leukemia is a B-cell lymphoma. In another embodiment, the leukemia is a T-cell lymphoma. In still another embodiment, the lymphoma is primary effusion lymphoma (PEL).

The formulations of Compound 1 show anti-proliferative activity in a variety of cancer cell lines. Anti-proliferative activity in these cancer cell lines indicates that the formulations of Compound 1 are useful in the treatment of cancers, including hematopoietic and solid tumors. In one embodiment, the hematopoietic and solid tumors are selected from bladder cancer, breast cancer, CNS cancer (for example, neuroblastoma, medulloblastoma and glioma), colon cancer, duodenum cancer, endocrine cancer (for example, thyroid cancer and adrenal gland cancer), female genitourinary cancer (for example, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, neuroblastoma, medulloblastoma and glioma), colon cancer, duodenum cancer, endocrine cancer (for example, thyroid cancer and adrenal gland cancer), female genitourinary cancer (for example, uterus cancer, cervix cancer, and vulva cancer), head and neck cancer, hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer.

In another embodiment, the formulations of Compound 1 described herein induce apoptosis in a variety of cancer cell lines. Induction of apoptosis indicates that the formulations of Compound 1 described herein are useful in the treatment of cancers, including hematopoietic and solid tumors. In one embodiment, the hematopoietic and solid tumors are selected from bladder cancer, breast cancer, CNS cancer (for example, neuroblastoma, and glioma), colon cancer, duodenum cancer, endocrine cancer (for example, thyroid cancer and adrenal gland cancer), female genitourinary cancer (for example, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, neuroblastoma, and glioma), colon cancer, duodenum cancer, endocrine cancer (for example, thyroid cancer and adrenal gland cancer), female genitourinary cancer (for example, vulva cancer), head and neck cancer (for example, esophageal cancer), hematopoietic and lymphoid cancer (for example, lymphoma, and leukemia), kidney cancer, liver cancer, lung cancer (for example, NSCLC and SCLC), pancreas cancer, prostate cancer, skin cancer (for example, melanoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, medulloblastoma, neuroblastoma, and glioma), colon cancer, duodenum cancer, endocrine cancer (for example, thyroid cancer and adrenal gland cancer), female genitourinary cancer (for example, placenta cancer, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer.

Also provided herein are methods for treating or preventing a cancer characterized by a BRAF mutation and/or a beta-catenin mutation (alternatively referred to as CTNNB1 mutation), comprising administering to a subject in need thereof an effective amount of a formulation of Compound 1, as described herein. In some such embodiments, the cancer is characterized by a BRAF mutation. In another embodiment, the cancer is characterized by a beta-catenin mutation. In yet another embodiment, the cancer is characterized by an activated beta-catenin pathway. In some such embodiments, the cancer is CRC or melanoma characterized by a BRAF mutation. In other embodiments, the cancer is CRC characterized by a beta-catenin mutation, additionally comprising an EGFR mutation or increased EGFR activity (for example, CRC characterized by an activated beta-catenin pathway and an EGFR mutation, or CRC characterized by an activated beta-catenin pathway and increased EGFR activity). In still other embodiments, the cancer is gastric cancer characterized by a beta-catenin mutation, additionally comprising a KRAS mutation (i.e. gastric cancer characterized by an activated beta-catenin pathway and a KRAS mutation). In another embodiment the cancer is HCC, characterized by an activated beta-catenin pathway. In some such embodiments, the BRAF mutation is BRAF V660E. In some such embodiments, the BRAF mutation is BRAF V600E. In some such embodiments, the BRAF mutation is one or more of BRAF V600E, BRAF T119S, or BRAF G596R. In some such embodiments, the beta-catenin mutation is one or more of beta-catenin S33Y, G34E, S45del, or S33C. In some such embodiments, the EGFR mutation is one or more of EGFR E282K, G719S, P753S, or V1011M. In some such embodiments, the KRAS mutation is A146T, G12C, G12D, G12V, G3D, or Q61L.

Also provided herein are methods for treating or preventing a cancer expressing PD-L1, comprising administering to a subject in need thereof an effective amount of a formulation of Compound 1, as described herein. In some such embodiments, the PD-L1 expressing cancer is melanoma, lung cancer, renal cell carcinoma (RCC), or HCC.

Also provided herein are methods for treating or preventing a cancer characterized by a BRAF mutation, comprising administering to a subject in need thereof an effective amount of a formulation of Compound 1, as described herein. In some such embodiments, the cancer characterized by a BRAF mutation is CRC, thyroid cancer, melanoma or lung cancer. In some such embodiments, the cancer characterized by a BRAF mutation is CRC, thyroid cancer, or lung cancer. In some such embodiments, the BRAF mutation is BRAF V660E. In some such embodiments, the BRAF mutation is BRAF V600E. In other embodiments, the BRAF mutation is one or more of BRAF V600E, BRAF T119S, or BRAF G596R.

Also provided herein are methods for treating or preventing a cancer characterized by an NRAS mutation, comprising administering to a subject in need thereof an effective amount of a formulation of Compound 1, as described herein. In some such embodiments, the cancer characterized by an NRAS mutation is melanoma.

Also provided herein are methods for treating or preventing a cancer characterized by a KRAS mutation, comprising administering to a subject in need thereof an effective amount of a formulation of Compound 1, as described herein. In some such embodiments, the cancer characterized by a KRAS mutation is CRC, pancreas cancer or lung cancer.

Also provided herein are methods for treating or preventing a cancer characterized by a beta-catenin mutation, comprising administering to a subject in need thereof an effective amount of a formulation of Compound 1, as described herein. Also provided herein are methods for treating or preventing a cancer characterized by an activated beta-catenin pathway, comprising administering to a subject in need thereof an effective amount of a formulation of Compound 1, as described herein. In some such embodiments, the cancer characterized by a beta-catenin mutation is CRC, stomach cancer, HCC or sarcoma. In some such embodiments, the cancer characterized by an activated beta-catenin pathway is CRC, stomach cancer, HCC or sarcoma.

Also provided herein are methods for treating or preventing hepatocellular carcinoma (HCC), comprising administering to a subject in need thereof an effective amount of a formulation of Compound 1, as described herein. In some such embodiments, the HCC is characterized by a beta-catenin mutation and/or increased YAP expression. In some such embodiments, the HCC is characterized by an activated beta-catenin pathway and/or increased YAP amplification expression. In some embodiments, the increased YAP expression is due to amplification or a mutation.

Also provided herein are methods for treating or preventing colorectal cancer (CRC), comprising administering to a subject in need thereof an effective amount of a formulation of Compound 1, as described herein. In some such embodiments, the CRC is characterized by a BRAF mutation and/or beta-catenin mutation. In some such embodiments, the CRC is characterized by a BRAF mutation and/or an activated beta-catenin pathway.

Also provided herein are methods for treating or preventing gastric cancer, comprising administering to a subject in need thereof an effective amount of a formulation of Compound 1, as described herein. In some such embodiments, the gastric cancer is characterized by a beta-catenin mutation. In some such embodiments, the gastric cancer is characterized by an activated beta-catenin pathway.

Also provided herein are methods for treating or preventing melanoma, comprising administering to a subject in need thereof an effective amount of a formulation of Compound 1, as described herein. In some such embodiments, the melanoma is characterized by a BRAF mutation and/or NRAS mutation.

Further provided herein are methods for predicting response to treatment with a formulation of Compound 1 described herein in a patient having a cancer characterized by a gene mutation, the method comprising: a) obtaining a biological test sample from the patient's cancer; b) obtaining the gene sequence of one or more genes selected from BRAF, NRAS, KRAS, and/or CTNNB1 in said biological test sample; c) comparing said gene sequence(s) to the gene sequence(s) of a biological wild-type sample; wherein the presence of a mutation indicates an increased likelihood of response to a formulation of Compound 1 described herein treatment of said patient's cancer. In some such embodiments, the method additionally comprises administering an effective amount of a formulation of Compound 1, as described herein.

Further provided herein are methods for predicting therapeutic efficacy of a formulation of Compound 1 described herein for treatment of a patient having a cancer characterized by a gene mutation, the method comprising: a) obtaining a biological test sample from the patient's cancer; b) obtaining the gene sequence(s) of one or more genes selected from BRAF, NAS, KRAS, and/or CTNNB1 in said biological test sample; c) comparing said gene sequence(s) to the gene sequence(s) of a biological wild-type sample; wherein the presence of a mutation indicates an increased likelihood of therapeutic efficacy of said treatment with a formulation of Compound 1 described herein for said patient. In some such embodiments, the method additionally comprises administering an effective amount of a formulation of Compound 1, as described herein.

In some embodiments, provided herein are methods for treating and preventing cancer metastasis, comprising administering to a subject in need thereof an effective amount of a formulation of Compound 1, as described herein. In some embodiments, the cancer is a metastatic cancer, in particular, a metastatic solid tumor or metastatic hematologic cancer, wherein the solid tumor and hematologic cancer is as described herein. In other embodiments, provided herein are methods of treating and preventing cancer metastasis, comprising administering to a subject in need thereof an effective amount of a formulation of Compound 1, as described herein. In yet another aspect, provided herein is methods of eradicating cancer stem cells in a subject, comprising administering to a subject in need thereof an effective amount of a formulation of Compound 1, as described herein. In other embodiments, provided herein are methods of inducing differentiation in cancer stem cells in a subject, comprising administering to a subject in need thereof an effective amount of a formulation of Compound 1, as described herein. In other embodiments, provided herein are methods of inducing cancer stem cell death in a subject, comprising administering to a subject in need thereof an effective amount of a formulation of Compound 1, as described herein. In some such embodiments, the cancer is a solid tumor or a hematological cancer, as described herein.

In one embodiment, provided herein are methods for achieving a Response Evaluation Criteria in Solid Tumors (RECIST 1.1) of complete response, partial response or stable disease in a patient comprising administering an effective amount of a formulation of Compound 1 described herein to a patient having a cancer, in particular a solid tumor as described herein. In another embodiment, provided herein are methods to increase Progression Free Survival rates, as determined by Kaplan-Meier estimates.

In one embodiment, provided herein are methods for preventing or delaying a Response Evaluation Criteria in Solid Tumors (RECIST 1.1) of progressive disease in a patient, comprising administering an effective amount of a formulation of Compound 1 described herein to a patient having a solid tumor as described herein. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain.

In certain embodiments, provided herein are methods for decreasing the size of target lesions in a patient compared to pre-treatment, comprising administering an effective amount of a formulation of Compound 1 described herein to a patient having a cancer, in particular a solid tumor as described herein.

In certain embodiments, provided herein are methods for decreasing the size of a non-target lesion in a patient compared to pre-treatment, comprising administering an effective amount of a formulation of Compound 1 described herein to a patient having a cancer, in particular a solid tumor as described herein.

In certain embodiments, provided herein are methods for achieving a reduction in the number of target lesions in a patient compared to pre-treatment, comprising administering an effective amount of a formulation of Compound 1 described herein to a patient having a cancer, in particular a solid tumor as described herein.

In certain embodiments, provided herein are methods for achieving a reduction in the number of non-target lesions in a patient compared to pre-treatment, comprising administering an effective amount a formulation of Compound 1 described herein to a patient having a cancer, in particular a solid tumor as described herein.

In certain embodiments, provided herein are methods for achieving a disappearance of all target lesions in a patient, comprising administering an effective amount of a formulation of Compound 1 described herein to a patient having a cancer, in particular a solid tumor as described herein.

In certain embodiments, provided herein are methods for achieving a disappearance of all non-target lesions in a patient, comprising administering an effective amount of a formulation of Compound 1 described herein to a patient having a cancer, in particular a solid tumor as described herein.

In certain embodiments, provided herein are methods for treating a cancer, in particular a solid tumor as described herein, the methods comprising administering an effective amount of a formulation of Compound 1 described herein to a patient having a cancer, in particular a solid tumor, wherein the treatment results in a complete response, partial response or stable disease, as determined by Response Evaluation Criteria in Solid Tumors (RECIST 1.1).

In certain embodiments, provided herein are methods for treating a cancer, in particular a solid tumor as described herein, the methods comprising administering an effective amount of a formulation of Compound 1 described herein to a patient having a cancer, in particular a solid tumor as described herein, wherein the treatment results in a reduction in target lesion size, a reduction in non-target lesion size and/or the absence of new target and/or non-target lesions, compared to pre-treatment.

In certain embodiments, provided herein are methods for treating a cancer, in particular a solid tumor as described herein, the methods comprising administering an effective amount a formulation of Compound 1 described herein to a patient having a cancer, in particular a solid tumor as described herein, wherein the treatment results in prevention or retarding of clinical progression, such as cancer-related cachexia or increased pain.

In another embodiment, provided herein are methods for inducing a therapeutic response characterized with the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586) of a patient, comprising administering an effective amount a formulation of Compound 1 described herein to a patient having a cancer, in particular hematological cancers such as lymphoma, as described herein. In another embodiment, provided herein are methods for achieving complete remission, partial remission or stable disease, as determined by the International Workshop Criteria (IWC) for NHL in a patient, comprising administering an effective amount of a formulation of Compound 1 described herein to a patient having a cancer, in particular hematological cancers such as lymphoma, as described herein. In another embodiment, provided herein are methods for achieving an increase in overall survival, progression-free survival, event-free survival, time to progression, disease-free survival or lymphoma-free survival as determined by the International Workshop Criteria (IWC) for NHL in a patient, comprising administering an effective amount of a formulation of Compound 1 described herein to a patient having a cancer, in particular hematological cancers such as lymphoma, as described herein.

In another embodiment, provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a patient, comprising administering an effective amount of a formulation of Compound 1 to a patient having a cancer, in particular multiple myeloma. In another embodiment, provided herein are methods for achieving a stringent complete response, complete response, very good partial response, or partial response, as determined by the International Uniform Response Criteria for Multiple Myeloma (IURC) in a patient, comprising administering an effective amount of a formulation of Compound 1 described herein to a patient having a cancer, in particular multiple myeloma. In another embodiment, provided herein are methods for achieving an increase in overall survival, progression-free survival, event-free survival, time to progression, or disease-free survival in a patient, comprising administering an effective amount of a formulation of Compound 1 described herein to a patient having a cancer, in particular multiple myeloma.

In another embodiment, provided herein are methods for inducing a therapeutic response assessed with the Response Assessment for Neuro-Oncology (RANO) Working Group for GBM (see Wen P., Macdonald, D R., Reardon, D A., et al. Updated response assessment criteria for high-grade gliomas: Response assessment in neuro-oncology working group. J. Clin. Oncol. 2010; 28: 1963-1972) of a patient, comprising administering an effective amount of a formulation of Compound 1 described herein to a patient having a cancer, in particular glioblastoma multiforme (GBM). In one embodiment, RANO will be used to establish the proportion of subjects progression-free at 6 months from Day 1 of treatment relative to efficacy evaluable subjects in the GBM type.

In another embodiment, provided herein are methods for improving the Eastern Cooperative Oncology Group Performance Status (ECOG) of a patient, comprising administering an effective amount a formulation of Compound 1 described herein to a patient having a cancer, in particular a solid tumor or hematological cancer as described herein.

In another embodiment, provided herein are methods for inducing a therapeutic response assessed by Positron Emission Tomography (PET) outcome of a patient, comprising administering an effective amount of a formulation of Compound 1 described herein to a patient having a cancer, in particular a solid tumor or hematological cancer as described herein. In certain embodiments, provided herein are methods for treating a cancer, in particular a solid tumor or hematological cancer as described herein, the methods comprising administering an effective amount of a formulation of Compound 1 described herein to a patient having a cancer, in particular a solid tumor or hematological cancer as described herein, wherein the treatment results in a reduction in tumor metabolic activity, for example, as measured by PET imaging.

Further provided herein are methods for treating patients who have been previously treated for a cancer, in particular a solid tumor or a hematological cancer as described herein, as well as those who have not previously been treated. Such methods include administration of a formulation of Compound 1 described herein. Because patients with a cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

A formulation of Compound 1 as provided herein can be use in any of the above described methods.

6. Examples

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| | |
|---|---|
| BHT | Butylated hydroxytoluene |
| CA | Citric acid |
| CU | Content uniformity |
| FaSSGF | Fasted state simulated gastric fluid |
| FaSSIF | Fasted state simulated intestinal fluid |
| FeSSGF | Fed state simulated gastric fluid |
| FeSSIF | Fed state simulated intestinal fluid |
| FIH | First in human |
| HP-β-CD | hydroxypropyl-beta-cyclodextrin |
| HPC | Hydroxypropyl cellulose |
| HPMC | Hydroxypropyl methylcellulose |
| MCC | Microcrystalline cellulose |
| PEG | Polyethylene glycol |
| PVA-P | Polyvinylacetate phthalate polymer |
| PVP VA64 | Vinylpyrrolidone-vinyl acetate copolymer |
| SA | Stearic acid |
| SD | Spray-drying |
| SLS | Sodium lauryl sulfate |
| SMB | Sodium metabisulfite |
| SDD | Spray-drying dispersion |
| SSF | Sodium stearyl fumarate |
| TPGS | Tocophersolan |

6.1 Preparation of Spray Dried Dispersion Formulations

Spray dried dispersion formulations of Compound were obtained from a spray-drying process of Compound 1 as depicted in FIG. 60. The spray-drying process comprised: (1) mixing Compound 1 with a solvent at 25° C. to yield a suspension; (2) heating the suspension to about 80° C. (78-88° C.); (3) spray-drying under the conditions in Table 1 or Table 2 to yield a spray dried dispersion formulation; and (4) collecting the resulting solids.

TABLE 1

Spray-drying conditions part A

| Entry No. | Formulation Active Loading-Dry Basis [wt %] | Formulation Description | Polymer Type | Polymer Loading in Solution [wt %] | Solvent | Spray Solution Solids Content [wt %] | Batch Size [g] | Wet Yield [%] |
|---|---|---|---|---|---|---|---|---|
| 1 | 10 | 10% A:HPMCAS-M | HPMCAS-M | 3.6 | Acetone | 4 | 2 | 100 |
| 2 | 25 | 25% A:HPMCAS-M | HPMCAS-M | 3.6 | Acetone | 4 | 0.8 | 87 |
| 3 | 25 | 25% A:PVP VA64 | PVP VA64 | 3.6 | Acetone | 4 | 0.8 | 82 |
| 4 | 25 | 25% A:PVA-P | PVA-P | 3.6 | 9/1 MeOH/Water | 4 | 0.8 | 90 |
| 5 | 25 | 10% A:HPMC E3 | HPMC E3 | 3.6 | 9/1 MeOH/Water | 4 | 0.8 | 64 |
| 6 | 25 | 25/65/10 A:PVP VA64:TPGS | PVP VA64 | 3 | Acetone | 4 | 1 | 91 |
| 7 | 25 | 25/65/10 A:PVA-P:TPGS | PVA-P | 3 | Acetone | 4 | 1 | 94 |
| 8 | 25 | 25/65/10 A:HPMC E3:TPGS | HPMC E3 | 2 | 9/1 Methanol/water | 4 | 1 | 25 |
| 9 | 50 | 50% A:PVA-P | PVA-P | 2 | 9/1 Acetone/Water | 4 | 0.5 | 100 |
| 10 | 50 | 50% A:HPMC E3 | HPMC E3 | 2 | 9/1 Methanol/water | 4 | 0.5 | 37 |
| 11 | 50 | 50/40/10 A:HPMC E3:TPGS | HPMC E3 | 2 | 9/1 Methanol/water | 4 | 0.5 | 52 |
| 12 | 50 | 50/40/10 A:PVA-P:TPGS | PVA-P | 2 | 9/1 Acetone/Water | 4 | 0.5 | 52 |

TABLE 1-continued

Spray-drying conditions part A

| Entry No. | Formulation Active Loading-Dry Basis [wt %] | Formulation Description | Polymer Type | Polymer Loading in Solution [wt %] | Solvent | Spray Solution Solids Content [wt %] | Batch Size [g] | Wet Yield [%] |
|---|---|---|---|---|---|---|---|---|
| 13 | 50 | 50/40/10 A:PVP VA64: TPGS | PVP VA64 | 2 | Acetone | 4 | 0.5 | 94 |

TABLE 2

Spray-drying condition part B

| Entry No. | SD Inlet Temp [° C.] | SD Outlet Temp [° C.] | SD Condenser Temp [° C.] | Drying Gas Flow Rate [g/min] | Soln Temp [° C.] | Solution Flow Rate [g/min] | Atomization Pressure [PSI] | Nozzle Type |
|---|---|---|---|---|---|---|---|---|
| 1 | 100 | 42 | Single Pass | 450 | rt | 29 | 110 | Schlick 2.0 |
| 2 | 94 | 42 | Single Pass | 450 | rt | 29 | 110 | Schlick 2.0 |
| 3 | 90 | 42 | Single Pass | 450 | rt | 29 | 110 | Schlick 2.0 |
| 4 | 84 | 42 | Single Pass | 450 | rt | 29 | 110 | Schlick 2.0 |
| 5 | 80 | 42 | Single Pass | 450 | rt | 29 | 110 | Schlick 2.0 |
| 6 | 105 | 42 | Single Pass | 450 | rt | 27 | 110 | Schlick 2.0 |
| 7 | 110 | 42 | Single Pass | 450 | rt | 27 | 110 | Schlick 2.0 |
| 8 | 110 | 42 | Single Pass | 450 | rt | 27 | 110 | Schlick 2.0 |
| 9 | 108 | 42 | Single Pass | 450 | rt | 27 | 110 | Schlick 2.0 |
| 10 | 93 | 42 | Single Pass | 450 | rt | 27 | 110 | Schlick 2.0 |
| 11 | 89 | 42 | Single Pass | 450 | rt | 27 | 110 | Schlick 2.0 |
| 12 | 84 | 42 | Single Pass | 450 | rt | 27 | 110 | Schlick 2.0 |
| 13 | 82 | 42 | Single Pass | 450 | rt | 27 | 110 | Schlick 2.0 |

6.2 Summary of Compound 1 Animal Pharmacokinetics (PK) Formulation Development Study Compound 1 is a basic moiety, and has a pH-dependent solubility profile. Under a normal gastric pH range, the solubility and bioavailability is expected to vary, leading to intra- and inter-patient PK variability. In-vitro and in-vivo evaluations of various Blend in Capsule (BIC) formulations were undertaken to minimize the pH dependence on the drug substance release.

A systematic formulation development was undertaken and resulted in the selection of three formulations (conventional formulation (F4-1 in Table 11) (A), enhanced formulation (F15, Table 27) (B), and spray dried dispersion (Entry 1, Table 1-Table 2) (SDD) (C)) for evaluation in a dog PK study. Formulation A (conventional excipients) demonstrated the highest variability in exposure, and a reduction of exposure at increased gastric pH. Formulation C (SDD) showed the highest exposures, but had a modest reduction of exposure at increased gastric pH.

Formulation B was recommended as the basis for First In Human (FIH) formulation development. Combining an acidifier (e.g. citric acid) and surfactant (e.g. sodium lauryl sulfate) provided a synergistic effect, by controlling local pH and enhancing drug solubility concurrently. Both formulations B and C demonstrated the potential to mitigate gastric pH impact. Formulation C utilized an amorphous SDD drug product intermediate.

6.3 Study 1 Prototype Formulations

Seven Compound 1 blends were prepared via the process listed in FIG. 1 for drug release (dissolution) evaluation. The compositions of each blend are shown in Table 3. The functional excipients were grouped into three classes: acidifiers (tartaric acid, fumaric acid, and citric acid), precipitation inhibitors (PEG4000 and hydroxypropyl cellulose), and solubilizer (hydroxypropyl-beta-cyclodextrin).

TABLE 3

Compositions of Prototype Formulations (Study 1)

| (% w/w) | F1-1 | F1-2 | F1-3 | F1-4 | F1-5 | F1-6 | F1-7 |
|---|---|---|---|---|---|---|---|
| Compound 1 citrate salt | | | | 26.7 | | | |
| MCC PH102 | 33.8 | | | 23.8 | | | |
| Mannitol | 33.8 | | | 23.8 | | | |
| Tartaric acid | | 20 | | | | | |
| Fumaric acid | | | 20 | | | | |
| Citric acid | | | | 20 | | | |
| PEG4000 | | | | | 20 | | |
| HPC | | | | | | 20 | |
| HP-β-CD | | | | | | | 20 |
| Kollidon CL | | | | 4.0 | | | |
| Colloidal SiO$_2$ | | | | 0.6 | | | |
| Stearic acid | | | | 1.0 | | | |
| Total | | | | 100 | | | |
| Total weight (mg) | | | | 250 | | | |

HPC = hydroxypropyl cellulose;
HP-β-CD = hydroxypropyl-beta-cyclodextrin;
MCC = microcrystalline cellulose;
PEG = polyethylene glycol.

Figure 2:
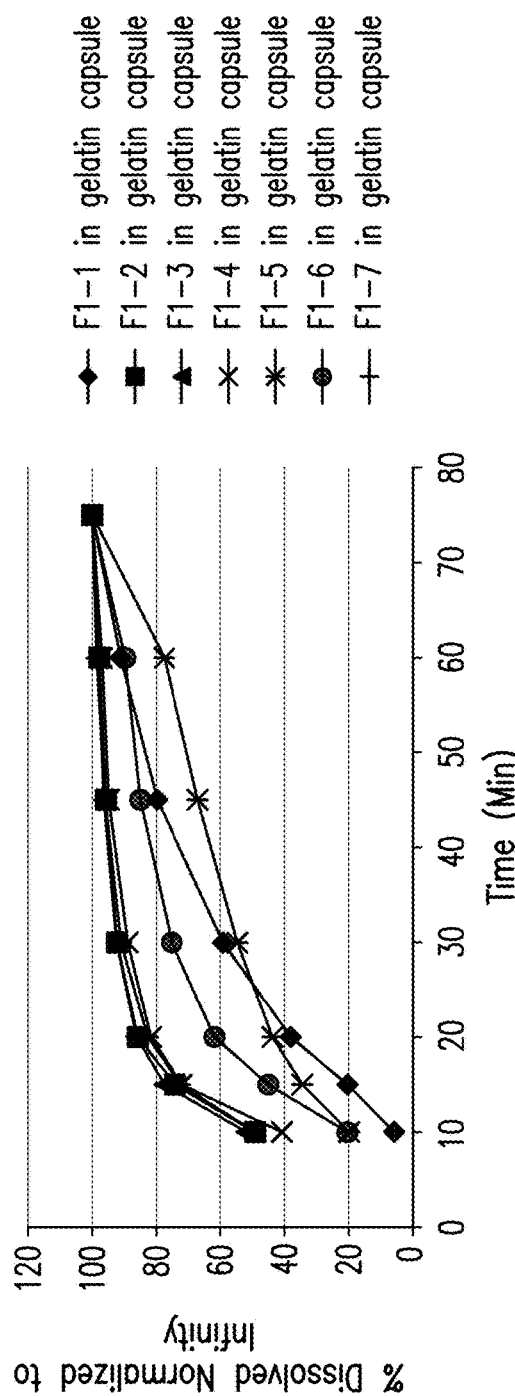
FIG. 2 shows dissolution profiles of Study 1 formulations in gelatin capsules under dissolution condition 1 in Table 4.
Figure 3:
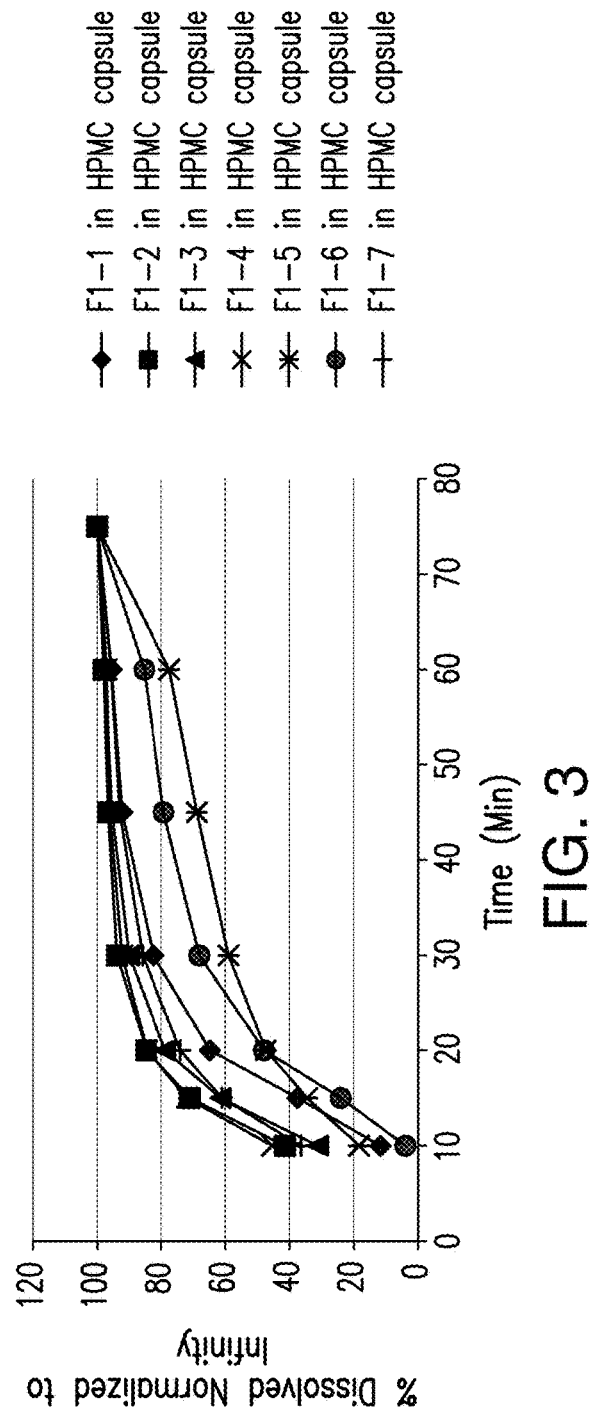
FIG. 3 shows dissolution profiles of Study 1 formulations in HPMC capsules under dissolution condition 1 in Table 4.
Figure 4:
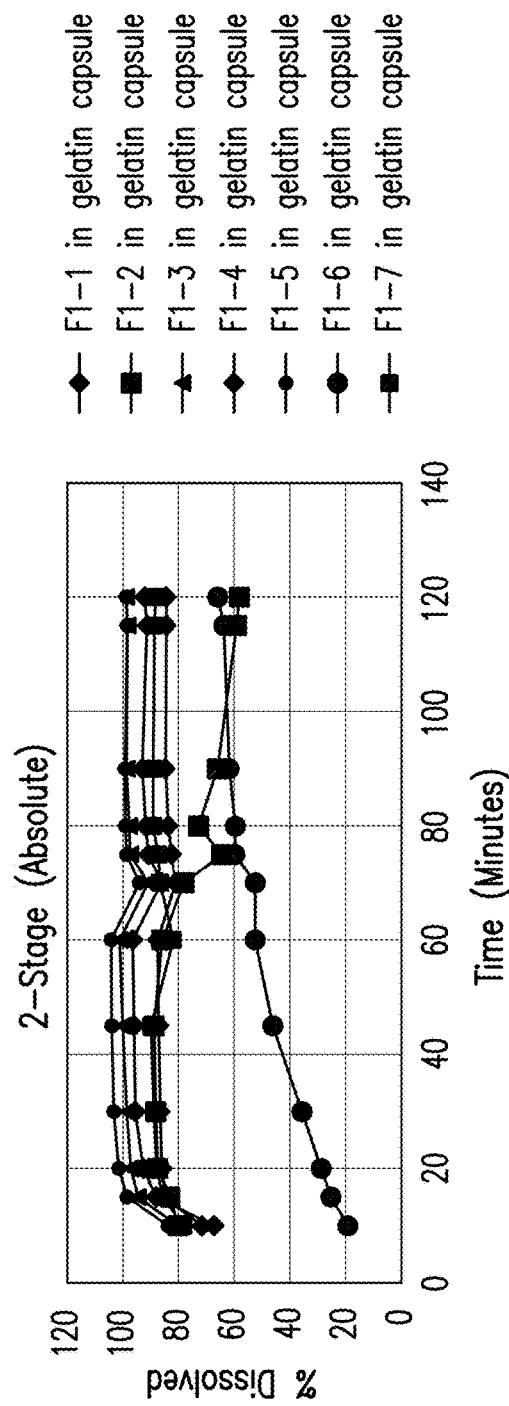
FIG. 4 shows dissolution profiles of Study 1 formulations in gelatin capsules under dissolution condition 2 in Table 5.
Figure 5:
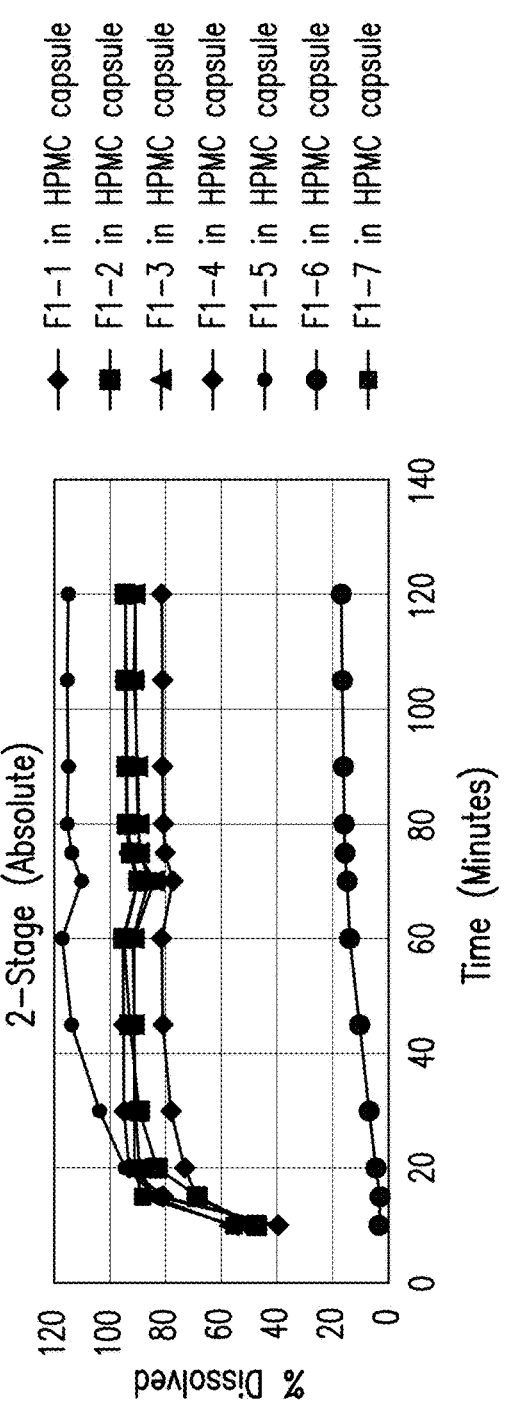
FIG. 5 shows dissolution profiles of Study 1 formulations in HPMC capsules under dissolution condition 2 in Table 5.

Dissolution condition 1 (Table 4) was used to evaluate the release of Study 1 formulations (Section 6.3) in gelatin (FIG. 2) and HPMC (FIG. 3) capsule shells. Two stage dissolution condition 2 (Table 5) was also used to evaluate the release of Study 1 formulations in gelatin (FIG. 4) and HPMC (FIG. 5) capsule shells.

Dissolution Conditions 1

TABLE 4

Dissolution Method for Formulation Studies 1, 2 (FaSSIF)

| Dissolution Parameter | Setting |
|---|---|
| Apparatus | USP Apparatus II (paddle) |
| Dissolution media | FaSSIF (pH 6.8) |
| Media volume | 900 mL |
| Media temperature | 37° C. ± 0.5° C. |
| RPM | 75 rpm for first 60 minutes and infinity (250 rpm for next 15 minutes) |
| Sampling time | 10, 15, 20, 30, 45, 60, and 75 minutes |
| Sample volume | 1.5 mL (no media replacement) |
| Flush volume | 3.0 mL |
| Offset Volume | 2.0 mL |
| Filter | 10 μm UHMW PE Full Flow Filters |
| Analysis | HPLC (UV 230 nm) |

RPM = revolutions per minute;
USP = United States Pharmacopeia.
FaSSIF = Fasted State Simulated Intestinal Fluid Dissolution Conditions 2

TABLE 5

Dissolution Method for Formulation Study 1 (Two Stage)

| Dissolution Parameter | Setting |
|---|---|
| Apparatus | USP Apparatus II (paddle) |
| Media temperature | 37° C. ± 0.5° C. |
| RPM | 75 rpm |
| Pull volume | 1.5 mL (no media replacement) |
| Flush volume | 3.0 mL |
| Offset Volume | 2.0 mL |
| Filter | 10 μm UHMW PE Full Flow Filters |
| Analysis | HPLC (UV 230 nm) |
| Dissolution media 1 | 0.1N HCl (pH~1.2, for gastric pH) |
| Media volume | 750 mL |
| Sampling time | 10, 15, 20, 30, 45, and 60 |
| Dissolution media 2 | 0.2M sodium phosphate tribasic added to vessel. Adjust vessel pH to 6.80 ± 0.05 |
| Media volume | 250 mL |
| Sampling time | 10, 15, 20, 30, 45, and 60 (after addition) |

RPM = revolutions per minute;
USP = United States Pharmacopeia.
FaSSIF = Fasted State Simulated Intestinal Fluid Conclusions from Study 1 include the elimination of excipients (tartaric acid, hydroxypropyl cellulose, and HP-β-CD) from consideration due to an undemonstrated ability to mitigate gastric pH impact as determined by the percentage of drug release.

Compound 1 precipitated during the buffer stage (pH 6.8) of the 2-stage dissolution in F1-2 gelatin capsules (tartaric acid).

F1-5 (PEG4000) percentage released was low in FaSSIF conditions.

F1-6 (HPC) percentage released was low in both FaSSIF and 2-stage dissolutions.

6.4 Study 2 Prototype Formulations

Six Compound 1 blends were prepared according to the process set forth in FIG. 1 for drug release (dissolution) evaluation. The compositions of each blend are shown in Table 6. The formulations were evaluated based on the combinations of various functional excipients, i.e., surfactant (SLS), acidifier+precipitation inhibitor (fumaric acid or citric acid+PEG4000), acidifier+surfactant (citric acid+SLS), precipitation inhibitor+surfactant (PEG4000+SLS), acidifier+precipitation inhibitor+surfactant (citric acid+PEG4000+SLS). See Table 7.

TABLE 6

Compositions of Prototype Formulations (Study 2)

| (% w/w) | F2-1 | F2-2 | F2-3 | F2-4 | F2-5 | F2-6 |
|---|---|---|---|---|---|---|
| Compound 1 citrate salt | | | 26.72 | | | |
| MCC PH102 | 13.84 | 13.84 | 28.84 | 18.84 | 18.84 | 8.84 |
| Mannitol | 13.84 | 13.84 | 28.84 | 18.84 | 18.84 | 8.84 |
| Fumaric acid | 20 | | | | | |
| Citric acid | 20 | | | 20 | | 20 |
| PEG4000 | 20 | 20 | | | 20 | 20 |
| SLS | | | 10 | 10 | 10 | 10 |
| Kollidon CL | | | 4.0 | | | |
| Colloidal SiO$_2$ | | | 0.6 | | | |
| Stearic acid | | | 1.0 | | | |
| Total | | | 100 | | | |
| Total weight (mg) | | | 250 | | | |

MCC = microcrystalline cellulose;
PEG = polyethylene glycol;
SLS = sodium lauryl sulfate.

In addition to the above six enhanced formulations, one formulation containing Compound 1 spray dried dispersion (SDD) blend was also prepared for drug release (dissolution) evaluation. The composition of the SDD formulation blend is shown in Table 7.

The SDD intermediate was prepared by the following procedures: Compound 1 was dissolved in acetone in Vessel 1. HPMC and TPGS were dissolved in water (heated to about 80° C.) in Vessel 2. Then the API in acetone solution was added to HPMC/TPGS aqueous solution at a ratio of 4:6 and mixed into a clear and homogeneous solution. The solution was then fed into Buchi B-290 under specified flow rate and inlet temperature. The SDD intermediate powder was obtained in the collection vessel.

Ten grams of formulation blend was prepared according to the process set forth in FIG. 1 where Compound 1 was the SDD.

TABLE 7

Compositions of Prototype Formulation F2-7 in Study 2 (SDD)

| Component | % w/w | Weight per capsule (mg) |
|---|---|---|
| Compound 1 free base | 20 | 135.1 mg SDD intermediate (37/53/10 Compound 1 free base/HPMC/TPGS) (54.0% w/w of the formulation) |
| HPMC | 28.6 | |
| TPGS | 5.4 | |
| MCC PH102 | 20.2 | 50.45 |
| Mannitol | 20.2 | 50.45 |
| Kollidon CL | 4.0 | 10 |

TABLE 7-continued

Compositions of Prototype Formulation F2-7 in Study 2 (SDD)

| Component | % w/w | Weight per capsule (mg) |
|---|---|---|
| Colloidal SiO$_2$ | 0.6 | 1.5 |
| Stearic acid | 1.0 | 2.5 |
| Total | 100 | 250 |

HPMC = hydroxypropyl methyl cellulose;
MCC = microcrystalline cellulose;
TPGS = Vitamin E (d-α-tocopheryl) polyethylene glycol 1000 succinate.

Dissolution condition 1 (Table 4) was used to evaluate the release of Study 2 formulations in gelatin (FIG. 6) and HPMC (FIG. 7) capsule shells. Dissolution condition 3 (Table 8) was also used to evaluate the release of Study 2 formulations in gelatin (FIG. 8) and HPMC (FIG. 9) capsule shells.

Among the formulations provided in Table 6, SLS alone (F2-3) and combined with acid (F2-4) or polymer (F2-5) provide a superior percentage released as compared to other formulations, suggesting that SLS is important for quick and immediate release of Compound 1. Combination of acid and polymer (F2-1, F2-2) does not offer synergistic effects. Likewise, combination of SLS, acid, and polymer (F2-6) does not result in the complete release of Compound 1 in gelatin capsules until the infinity time point, and has slightly slower release in HPMC capsules. Therefore, PEG4000 does not improve the drug substance release and was therefore eliminated from further evaluation. SDD (F2-7) has a slower release profile, but completely releases prior to infinity.

Solubility of Compound 1 was determined in various percentages of sodium lauryl sulfate (SLS). 0.03% SLS was selected as the media for dissolution condition 3. Samples were filtered using a 0.2 μm nylon syringe filter, and analyzed by UPLC-UV utilizing the method parameters listed in Table 9.

TABLE 8

Solubility of Compound 1 citrate in pH 6.5 phosphate buffer with SLS

| % SLS | Solubility (mg salt/mL) |
|---|---|
| 0.01 | 0.000 |
| 0.02 | 0.001 |
| 0.03 | 0.054 |
| 0.05 | 0.336 |
| 0.1 | 0.807 |

SLS = Sodium lauryl sulfate

TABLE 9

UPLC Method Conditions for Formulation Stability

| UPLC Parameter | Setting | | |
|---|---|---|---|
| Column | Waters Acquity UPLC CSH C18 | | |
| Dimensions | 3.0 × 150 mm | | |
| Particle size | 1.7 μm | | |
| Column temperature | 45° C. | | |
| Autosampler temperature | 5° C. | | |
| Mobile phases | A: 0.01% TFA in Water B: Acetonitrile | | |
| Injection volume | 4 μL | | |
| Flow rate | 0.5 mL/minute | | |
| Run time | 26 minutes | | |
| Detection wavelength | 244 nm | | |
| | Time (min.) | A % | B % |
| Gradient | 0.0 | 90 | 10 |
| | 1.0 | 90 | 10 |
| | 14.0 | 50 | 50 |
| | 20.0 | 10 | 90 |
| | 21.0 | 10 | 90 |
| | 21.1 | 90 | 10 |
| | 26.0 | 90 | 10 |

6.5 Study Prototype Formulations

Study 3 included capsules prepared in Studies 1 and 2. F3-1 was F1-1 from Study 1 filled into Size #00 white opaque gelatin capsules. F3-2 was F1-4 from Study 1 filled into Size #00 white opaque gelatin capsules. F3-3 was F1-3 from Study 2 filled into Size #00 white opaque gelatin capsules. F3-4 was the pure SDD intermediate powder filled into Size #00 white opaque gelatin capsules. Due to the low bulk density of the SDD intermediate, the maximum amount of 108.08 mg was filled into the capsule shell, equivalent to 40 mg dose of Compound 1 free base. F3-5 was F2-7 from Study 2 compressed into a tablet. 200 mg of F3-5 blend was compressed into a single tablet by a Carver Press using 2000 lb compaction force and a standard flat-faced tooling. F3-6 had similar formulation components as F3-5, but with an increased level of disintegrant (Kollidon CL) at 10% instead of 4%. F3-6 was prepared in the same way as F2-7 was prepared in Study 2. In order to compare its dissolution profile with F3-4 and F3-5, F3-6 had 200 mg of blend filled into Size #0 gelatin capsules to render the same dose strength of 40 mg as in F3-4 and F3-5. The compositions of each blend are shown in Table 10.

TABLE 10

Compositions of prototype formulations (Study 3)

| (% w/w) | F3-1 | F3-2 | F3-3 | F3-4 | F3-5 | F3-6 |
|---|---|---|---|---|---|---|
| Compound 1 citrate salt | | 26.7 | | | | |
| Compound 1 SDD[1] | | | | 100 | 54.0 | 54.0 |
| MCC PH102 | 33.8 | 23.8 | 28.84 | | 20.2 | 17.2 |
| Mannitol | 33.8 | 23.8 | 28.84 | | 20.2 | 17.2 |
| Citric acid | | 20 | | | | |
| SLS | | | 10 | | | |

TABLE 10-continued

Compositions of prototype formulations (Study 3)

| (% w/w) | F3-1 | F3-2 | F3-3 | F3-4 | F3-5 | F3-6 |
|---|---|---|---|---|---|---|
| Kollidon CL |  | 4.0 |  |  | 4.0 | 10.0 |
| Colloidal SiO$_2$ |  | 0.6 |  |  | 0.6 | 0.6 |
| Stearic acid |  | 1.0 |  |  | 1.0 | 1.0 |
| Total |  |  | 100 |  |  |  |
| Total weight (mg) |  | 250 |  | 108.08 | 200 | 200 |
| Milligram Compound 1 |  | 50 |  |  | 40 |  |

Figure 8:
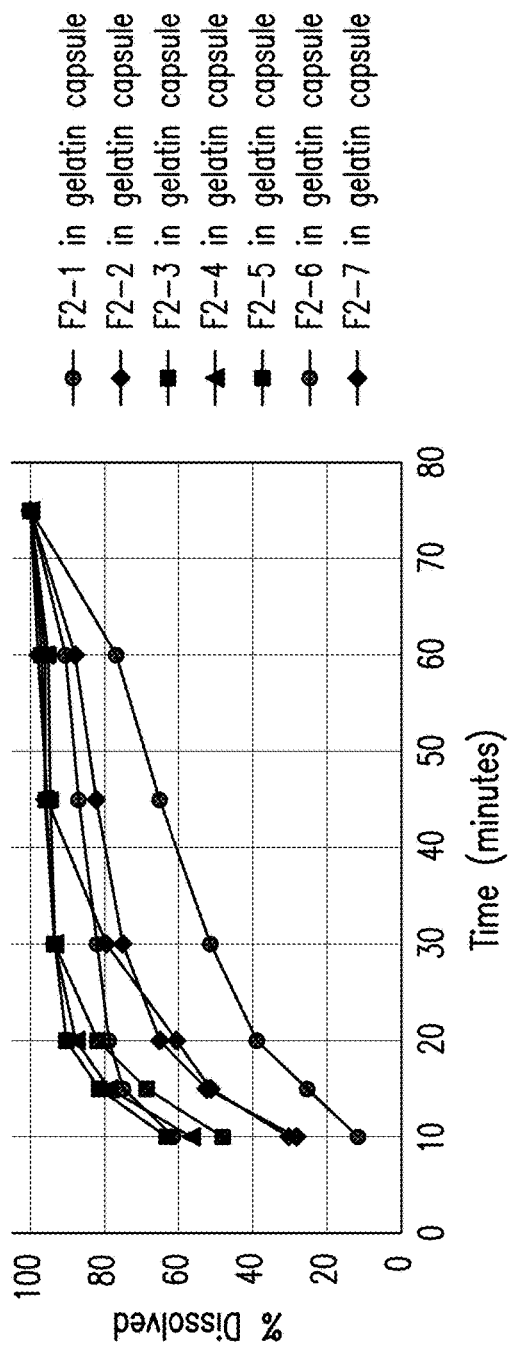
FIG. 8 shows dissolution profiles of Study 2 formulations in gelatin capsules under dissolution condition 2 in Table 5.
Figure 9:
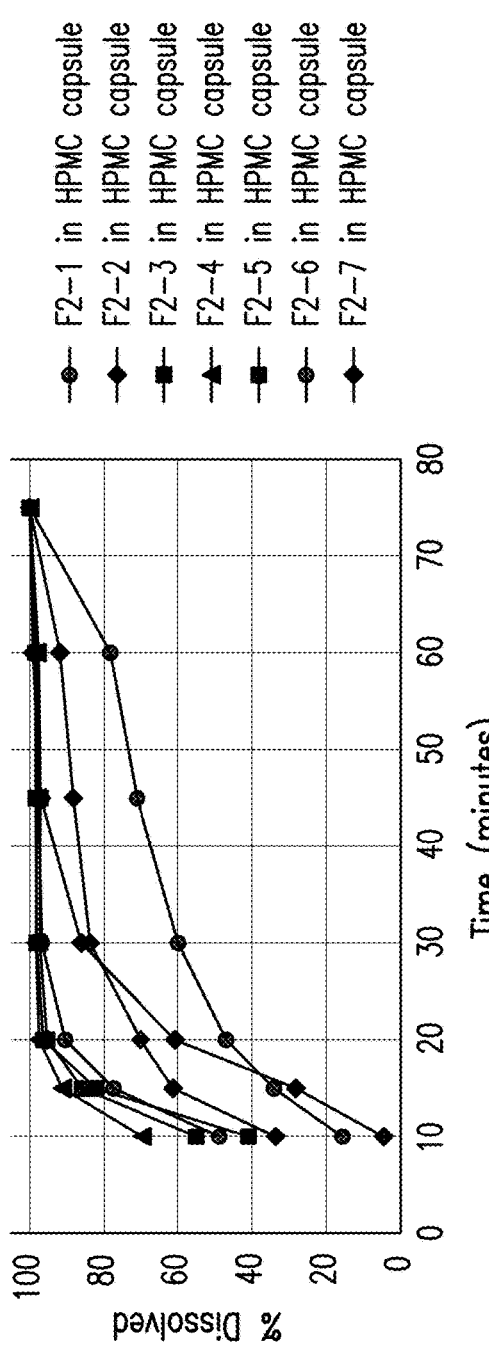
FIG. 9 shows dissolution profiles of Study 2 formulations in HPMC capsules under dissolution condition 2 in Table 5.
Figure 10:
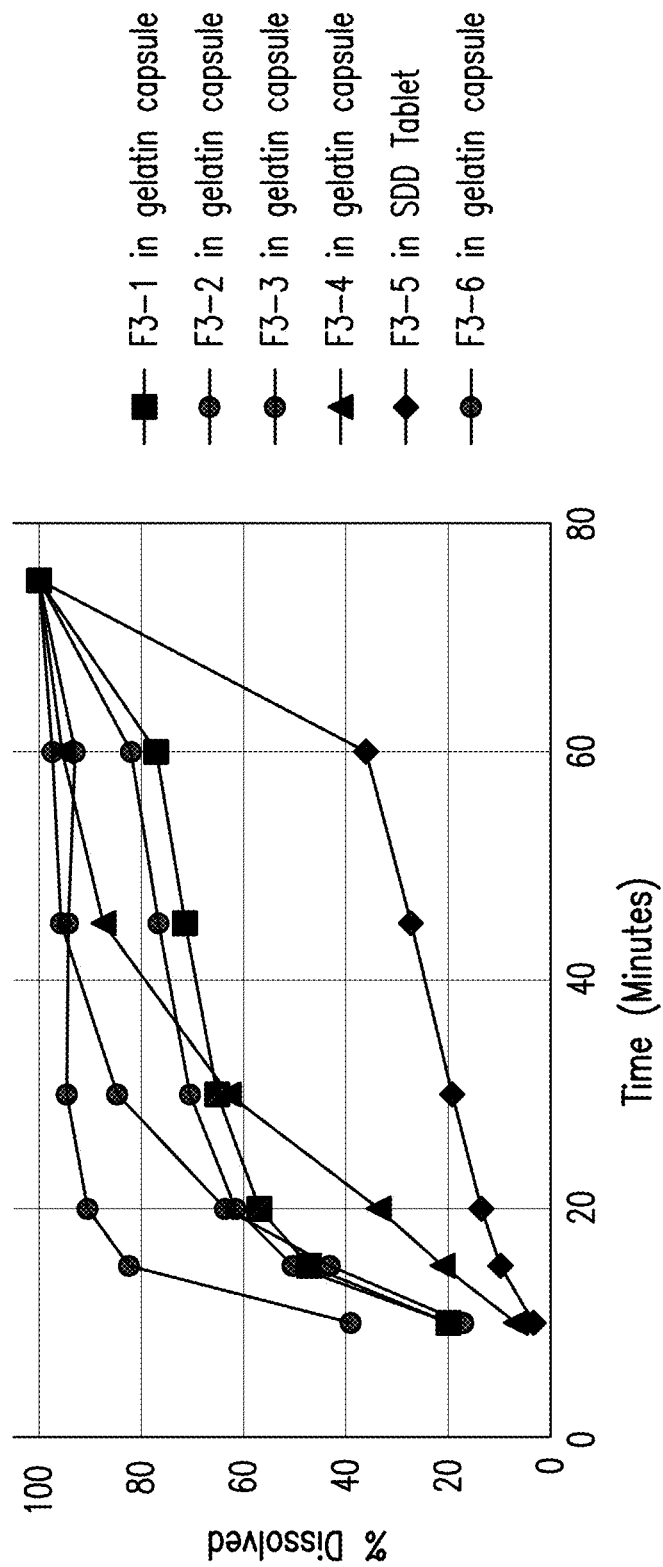
FIG. 10 shows dissolution profiles of Study 3 formulations in gelatin capsules under dissolution condition 2 in Table 5.

MCC = microcrystalline cellulose;
SLS = sodium lauryl sulfate.
F3-1 = F1-1 (Study 1);
F3-2 = F1-4 (Study 1);
F3-3 = F2-3 (Study 2);
F3-5 (compressed into tablet) = F2-7 (Study 2 prepared as capsule)
[1]SDD = 37/53/10% w/w/w Compound 1 free base/HPMC/TPGS As no major difference in dissolution performance was observed between gelatin capsules and HPMC capsules of the same formulation in Study 1 and Study 2, gelatin capsule was selected in the subsequent dissolution evaluations. Dissolution condition 3 (Table 8) was used to evaluate the release of Study 3 formulations (FIG. 10). Study 3 includes gelatin capsules prepared in Studies 1 and 2, and analyzed using dissolution method 3, also used to evaluate Study 2 samples (FIG. 8).

F3-1 was prepared in Study 1, as F1-1. F3-2 was prepared in Study 1, as F1-4. F3-3 was prepared in Study 2, as F2-3. F3-4 contained only SDD intermediate filled into capsules. F3-5 was prepared in Study 2, as F2-7 SDD, and was compressed into a tablet. F3-6 was a new SDD formulation (with increased disintegrant level) for Study 3.

F3-3 demonstrated the fastest drug release among all the six formulations, confirming the conclusions from Study 2, i.e., SLS made key contributions to the enhanced drug release profile. F3-2 (Citric Acid) demonstrated similar dissolution profile as that of F3-1 (Conventional), implying that acid alone is not as effective as SLS to enhance the drug dissolution. The dissolution of the new SDD formulation F3-6 was improved as compared to the original SDD formulation, most likely due to the increased level of disintegrant in the formulation. However, it was still slower than F3-3, the enhanced formulation with SLS. F3-5 (SDD tablet) did not disintegrate, and the addition of a super disintegrant (e.g., Ac-Di-Sol, croscarmellose sodium) would likely be advantageous to drug release if a tablet formulation is investigated in the future.

6.6 Study 4 Prototype Formulations

Study 4 evaluated acidifier, surfactant, and combinations of acidifier and surfactant. Seven Compound 1 blends were prepared according to the process set forth in FIG. 1 for drug release (dissolution) evaluation. The compositions of each blend are shown in Table 11. In this study, drug loadings were reduced from 26.7% (50 mg dose) to 13.36% (20 mg dose), and fill weight set to 200 mg in order to match the dose strength required in the animal PK study.

TABLE 11

Compositions of prototype formulations (Study 4)

| (% w/w) | F4-1 | F4-2 | F4-3 | F4-4 | F4-5 | F4-6 | F4-7 |
|---|---|---|---|---|---|---|---|
| Compound 1 citrate salt |  |  |  | 13.36 |  |  |  |
| Compound 1 SDD[1] |  |  |  |  |  |  | 27.88 |
| MCC PH102 | 40.52 | 35.52 | 35.52 | 38.02 | 33.02 | 33.02 | 33.26 |
| Mannitol | 40.52 | 35.52 | 35.52 | 38.02 | 33.02 | 33.02 | 33.26 |
| Citric acid |  | 10 |  |  | 10 |  |  |
| Fumaric acid |  |  | 10 |  |  | 10 |  |
| SLS |  |  |  | 5 | 5 | 5 |  |
| Kollidon CL |  |  |  | 4 |  |  |  |
| Colloidal SiO$_2$ |  |  |  | 0.6 |  |  |  |
| Stearic acid |  |  |  | 1 |  |  |  |
| Total |  |  |  | 100 |  |  |  |
| Total weight (mg) |  |  |  | 200 |  |  |  |

Figure 11:
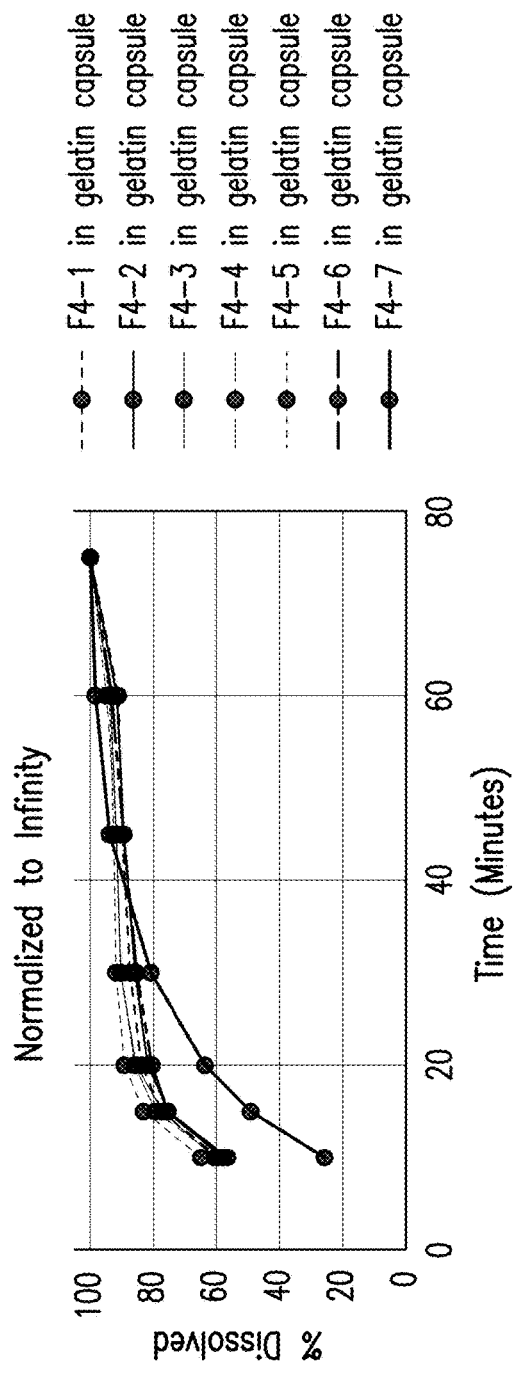
FIG. 11 shows dissolution profiles of Study 4 formulations in gelatin capsules under dissolution condition 3 in Table 8.

MCC = microcrystalline cellulose;
SLS = sodium lauryl sulfate.
[1]SDD = 37/53/10% w/w/w Compound 1 free base/HPMC/TPGS Dissolution condition 3 (Table 8) was used to evaluate the release of Study 4 formulations in gelatin (FIG. 11) capsule shells.

Citric acid+SLS (F4-5) formulation was superior to the other formulations in dissolution release, although the difference is not significant under the dissolution conditions used. The dose strength in Study 4 was reduced from 50 mg per capsule used in Studies 1-3 to 20 mg per capsule in order to mimic the dose strength used in the subsequent animal PK study.

Disintegration of SDD capsules (F4-7) is slow due to the high amount of a polar HPMC in the spray dried intermediate.

F4-1 (conventional), F4-5 (enhanced: citric acid+SLS), and F4-7 (enabled: SDD) are selected for a 1 month stability assessment (Section 6.7) and evaluation in a dog PK Study (Section 6.8).

6.7 Preliminary Stability Results for Selected Capsule Formulations

Three selected formulations from Study 4 (Section 6.6) were evaluated for stability in open dish conditions. Assay and impurities were evaluated for storage up to 1 month at 25° C./60% RH and 40° C./75% RH. Liquid Chromatography was used to evaluate the samples.

The F4-1 impurity (RRT 0.96) result was not replicated in the 1 month 40° C./75% RH sample, and was likely not sample related. The F4-7 impurity (RRT 0.89) result did replicate in the 2 week and 1 month 40° C./75% RH samples, and was likely sample related.

Acceptable stability was demonstrated for the three formulations when stored for 1 month at 25° C./60% RH and 40° C./75% RH.

6.8 Dog PK Overview

Three formulations were tested in an animal PK Study to assess exposure and identify a lead first in human formulation.

In the study, 15 fasted male dogs (5/group) were administered two doses of pentagastrin (0.006 mg/kg) to increase gastric acid secretion via the intramuscular route separated by a period of 60 minutes. A single 20 mg Compound 1 capsule (equivalent to 2 mg/kg) was administered 30 minutes following the second pentagastrin dose.

Following a washout period of 1 week, all animals were fasted and administered an oral dose of 40 mg famotidine to inhibit stomach acid production approximately 30 minutes prior to administration of a single 20 mg Compound 1 capsule.

TABLE 12

HPLC Assay and Impurity Results for Selected Formulations

| Formulation | Assay | 0.36 | 0.41 | 0.84 | 0.89 | 0.95 | 0.96 | 0.98 | 1.04 | 1.10 | Total Impurities |
|---|---|---|---|---|---|---|---|---|---|---|---|
| F4-1 | | | | | | | | | | | |
| Initial | 85.7 | ND | ND | ND | <QL | 0.51 | ND | 0.33 | <QL | 0.32 | 1.16 |
| 2W 40° C./75% RH | 90.9 | ND | ND | ND | <QL | 0.50 | 0.06 | 0.32 | <QL | 0.31 | 1.20 |
| 1M 25° C./60% RH | 90.5 | ND | ND | ND | <QL | 0.50 | ND | 0.32 | <QL | 0.32 | 1.14 |
| 1M 40° C./75% RH | 90.0 | ND | ND | ND | <QL | 0.50 | ND | 0.32 | <QL | 0.32 | 1.14 |
| F4-5 | | | | | | | | | | | |
| Initial | 85.3 | ND | ND | ND | <QL | 0.50 | <QL | 0.33 | <QL | 0.31 | 1.15 |
| 2W 40° C./75% RH | 87.8 | ND | ND | <QL | <QL | 0.51 | <QL | 0.33 | <QL | 0.31 | 1.15 |
| 1M 25° C./60% RH | 88.2 | <QL | <QL | ND | <QL | 0.51 | ND | 0.33 | <QL | 0.31 | 1.15 |
| 1M 40° C./75% RHF | 71.9 | <QL | <QL | ND | <QL | 0.51 | ND | 0.34 | <QL | 0.30 | 1.15 |
| F4-7 | | | | | | | | | | | |
| Initial | 95.5 | ND | 0.05 | ND | <QL | 0.52 | <QL | 0.40 | <QL | 0.31 | 1.28 |
| 2W 40° C./75% RH | 96.3 | ND | <QL | ND | 0.06 | 0.52 | <QL | 0.39 | <QL | 0.31 | 1.27 |
| 1M 25° C./60% RH | 95.7 | ND | <QL | ND | <QL | 0.52 | ND | 0.39 | <QL | 0.31 | 1.22 |
| 1M 40° C./75% RH | 93.3 | ND | <QL | ND | 0.08 | 0.52 | ND | 0.39 | <QL | 0.31 | 1.29 |

QL = quantitation limit = 0.05%;
RRT = relative retention time.
Shaded cells = changed observed;
ND = not determined No significant changes in assay were observed with the exception of F4-5, 1 month 40° C./75% RH condition. As there was no change in impurity profile, this result was likely related to capsule fill weight or the extraction procedure utilized in the assay method.

No significant changes (≥0.10%) were observed for impurities in any of the formulations. F4-5 had equivalent impurity values (none ≥QL). F4-1 and F4-7 each had one impurity that grows >QL at the 40° C./75% RH condition.

The gastric pH of each animal was measured prior to pretreatment, and prior to Compound 1 dosing. Blood samples were collected from each animal to obtain Compound 1 concentrations.

The formulations tested in the Study are described in Table 11, and summarized below.

Figure 12:
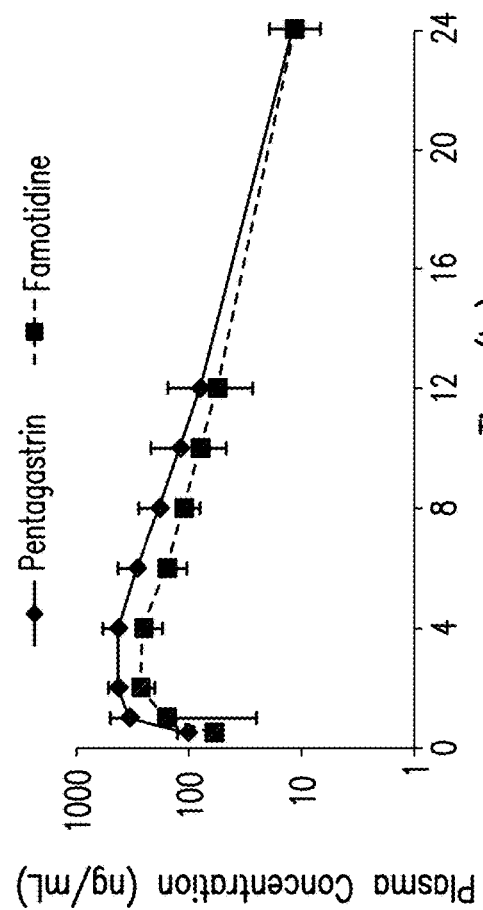
FIG. 12 shows the plasma concentration of Compound 1 over a 24 hour post dose time after administration of Formulation F4-1 of Study 4 formulations in Table 11.
Figure 13:
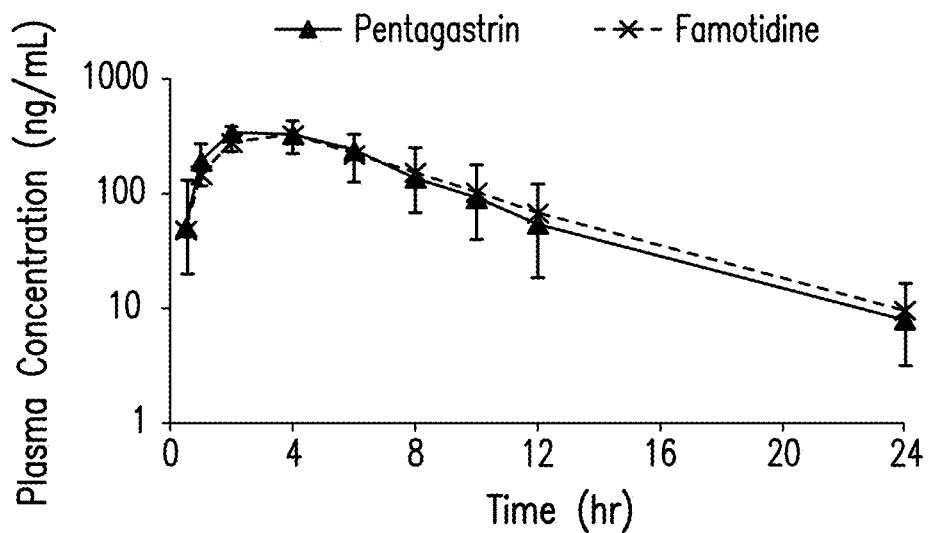
FIG. 13 shows the plasma concentration of Compound 1 over a 24 hour post dose time after administration of Formulation F4-5 of Study 4 formulations in Table 11.
Figure 14:
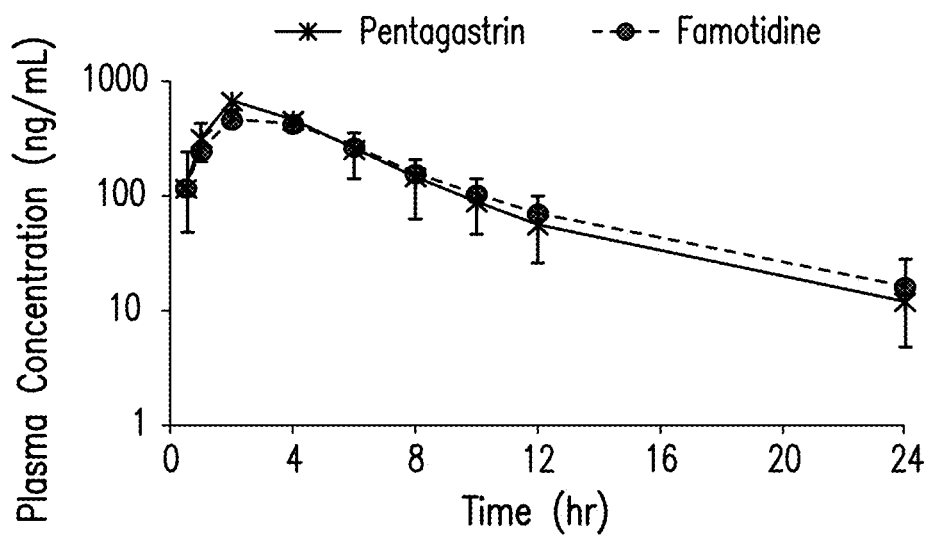
FIG. 14 shows the plasma concentration of Compound 1 over a 24 hour post dose time after administration of Formulation F4-7 of Study 4 formulations in Table 11.
Figure 15:
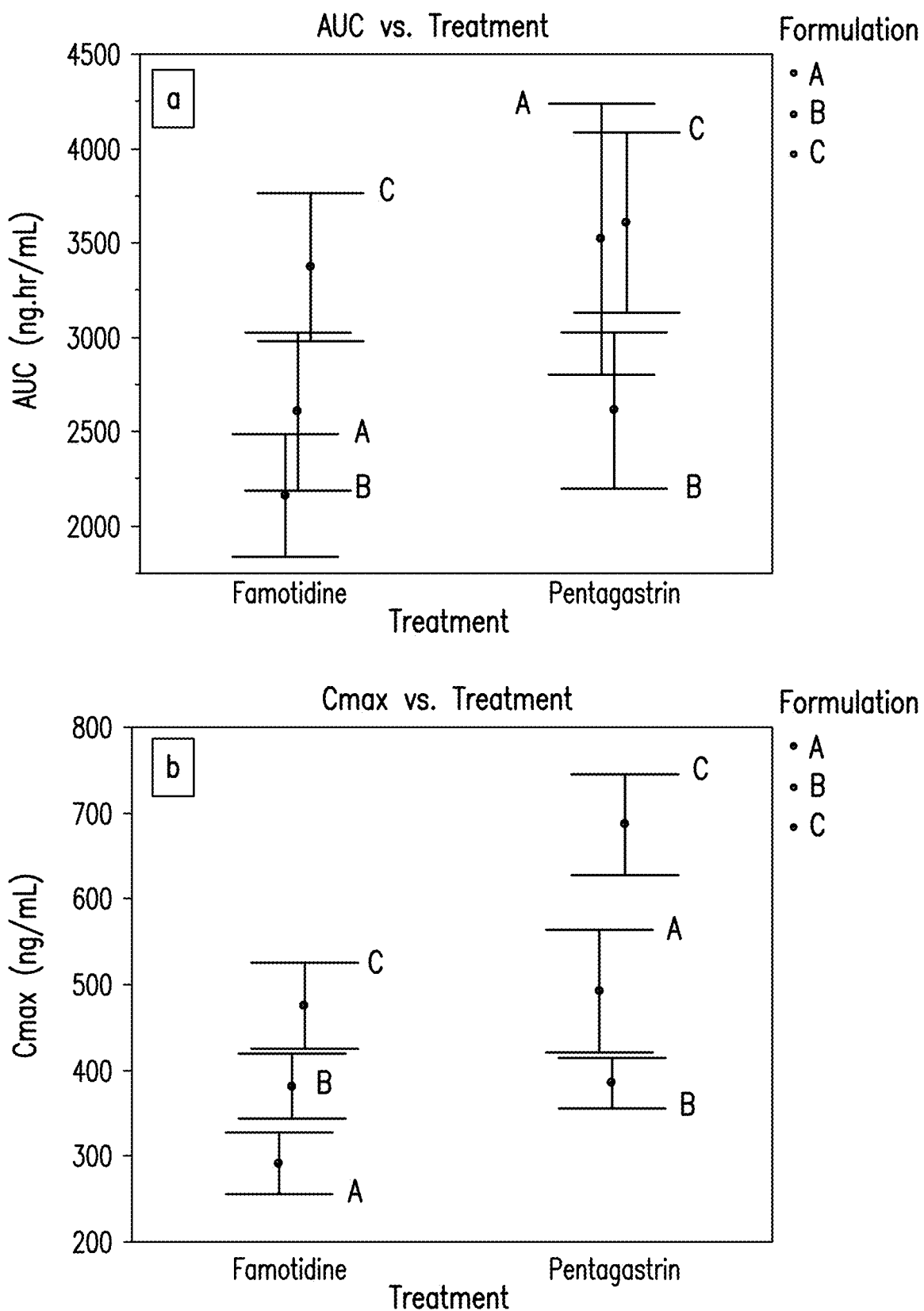
FIG. 15 shows the comparison in AUC and $C_{max}$ across Formulations F4-1, F4-5 and F4-7 of Study 4 formulations in the two pH-controlled dog groups as provided in Table 13.

F4-1: Conventional formulation: 10% Compound 1
F4-5: Enhanced formulation: 10% Compound 1+10% citric acid+5% SLS F4-7: Enabled formulation: spray-dried intermediate (10% active, 14.8% HPMC, 2.8% TPGS) with conventional excipients Table 13 listed the gastric pH and PK results for the study. FIG. 12, FIG. 13 and FIG. 14 showed the plasma concentration of Compound 1 over a 24 hour post dose time. FIG. 15 showed the comparison in AUC and $C_{max}$ across the three different formulations in the two pH-controlled dog groups.

TABLE 13

Mean Pharmacokinetic Parameters Following a Single Oral Capsule Administration of Compound 1 to Male Beagle Dogs

| Formulation | Pre-treatment | Gastric pH[1] | $T_{max}$ (hr)[2] | $C_{max}$ (ng/mL) | $AUC_{24h}$ (ng*h/mL) |
|---|---|---|---|---|---|
| F1 (Standard) | Pentagastrin | 3.4 (2.2-5.0) | 2.0 (1.0-4.0) | 492 ± 160 | 3520 ± 1610 |
| | Famotidine | 7.5 (7.1-7.9) | 2.0 (1.0-4.0) | 292 ± 80.4 | 2160 ± 726 |
| F5 (Enhanced) | Pentagastrin | 2.7 (2.2-3.8) | 4.0 (2.0-4.0) | 385 ± 65.9 | 2610 ± 926 |
| | Famotidine | 7.5 (7.3-7.7) | 2.0 (1.0-4.0) | 382 ± 84.6 | 2610 ± 936 |
| F7 (Enabled) | Pentagastrin | 2.4 (1.9-3.2) | 2.0 (2.0) | 686 ± 131 | 3610 ± 1070 |
| | Famotidine | 7.1 (5.5-7.7) | 2.0 (2.0-4.0) | 475 ± 112 | 3370 ± 877 |

$AUC_{24h}$ = area under the plasma concentration-time curve from time 0 to 24 hours post-dose;
$C_{max}$ = maximum plasma concentration;
$T_{max}$ = time to maximum plasma concentration ($C_{max}$)
[1]Gastric pH measured prior to Compound 1 administration. Average for each group and range reported.
[2]$T_{max}$ values are reported as median (range), while other parameters are reported as mean ± SD (n = 5).

The conventional formulation (F4-1) exhibited the highest variability in exposure between two pH treatment groups, and is not proposed as the FIH formulation.

The enabled formulation (F4-7) containing the SDD demonstrated higher $C_{max}$ and AUC than the enhanced formulation (F4-5), and demonstrated less variability in comparison to F4-1.

The enhanced formulation (F4-5) containing the crystalline API demonstrated the most consistent $C_{max}$ and AUC values at both low and high gastric pH conditions. The average $C_{max}$ and AUC values were approximately equivalent to F4-1, and the average AUC was 75% and $C_{max}$ was approximately 65% of the F4-7 results.

The enhanced formulation was selected for the FIH formulation due to more consistent PK results over the pH range studied and the elimination of the manufacture of the spray dried dispersion (SDD).

6.9 Conclusions

Clinical exposure to Compound 1 could vary based upon patient stomach pH. A systematic formulation development was undertaken to minimize the impact of gastric pH variability on exposure, thereby reducing intra- and inter-patient PK variability.

An enhanced formulation containing citric acid and sodium lauryl sulfate demonstrated minimal variability in exposure upon gastric pH change in an animal PK study.

The enabled formulation containing the SDD had the highest overall exposure, and showed moderate exposure variability with gastric pH. Given the dose range of interest in clinical studies, it is the exposure variability rather than the absolute exposure that is of most interest. The formulation required an additional spray drying step in the manufacturing process and offered little advantage over the enhanced formulation.

6.10 Summary of Compound 1 First in Human Formulation (FIH) Development Study

Compound 1 is intended for the treatment of colorectal cancer. A big portion of the patient population who take proton pump inhibitors (PPI) may exhibit higher gastric pH than normal patients. Compound 1 has a pH dependent solubility profile, resulting in potential intra- and inter-patient PK variability. Blend in capsule formulation development was undertaken to minimize the pH dependence on the drug substance release.

An enhanced formulation combining an acidifier (citric acid) and surfactant (sodium lauryl sulfate) for control of local pH and enhancing drug solubility exhibited minimal change in Compound 1 exposures in dogs pretreated with pentagastrin (increases gastric acid secretion) or famotidine (inhibits stomach acid production). This formulation was the starting composition for FIH formulation development studies.

Systematic development and evaluation (stability and dissolution) of formulations containing conventional excipients, acidifiers, surfactants, antioxidants, and lubricants was performed. The combination of surfactant and acidifier improved the chemical stability over just the surfactant, with fumaric acid having better chemical stability than citric acid. Formulations containing citric acid (low dose in gelatin capsules) showed capsule shell breakage at accelerated stability condition. Therefore, fumaric acid was selected as the acidifier in lieu of citric acid in the formulation. Based on the accelerated stability assessment program (ASAP) data, the FIH formulation had a projected shelf life of three years at room temperature, irrespective of packaging and desiccant addition.

The addition of surfactant and acidifier to a conventional formulation reduced the differences in dissolution release profile across the physiological pH range, with the pH 6.8 buffer system having the fastest release. Inter capsule dissolution release variability was noted in formulations containing fumaric acid and sodium laureth sulfate filled into HPMC capsules shells. It should be noted that the dissolution variability was drastically minimized when the same formulation was filled into Gelatin capsule shells. Thus, Gelatin capsule shells were recommended for this formulation.

The FIH formulations had been successfully scaled to 2 kg. The clinical dose range is 1 to 150 mg, and a common blend may not cover the entire range. Additionally, the needle particle morphology of the drug substance resulted in poor flow for high drug load blends. Initially, three capsule strengths (1, 5, and 25 mg) were targeted, however in balancing drug load for a passable flow, and capsule size, the highest capsule strength was reduced to 20 mg. Blend flow, stratified capsule homogeneity, and sticking on the tamping pins may be manufacturing challenges, and were monitored during development.

6.11 Introduction

The objective of the Compound 1 first in human (FIH) development program was to create a phase-appropriate immediate-release, solid oral dosage form and manufacturing process that consistently meets safety and efficacy requirements of the Quality Target Product Profile (QTPP) throughout the product's intended shelf life.

A prototype blend in capsule (BIC) formulation was selected based on previous animal PK studies as a starting point for FIH formulation development. Information from an initial Target Product Profile (TPP) was used as the design basis for the drug product, which is summarized in Table 14.

TABLE 14

Target Product Profile (Initial for FIH)

| | |
|---|---|
| Dosage Form | Solid oral (formulated blend in capsule) |
| Dose | Target range 1 to 150 mg, obtained from multiple dosage form strengths |
| Storage | Room temperature |

Table 15 represents a contemporary form of the Quality Target Product Profile, and lists the type of information that was used to provide further guidance during FIH formulation development.

TABLE 15

Quality Target Product Profile (Initial for FIH)

| | |
|---|---|
| Delivery/Release Characteristics | Appropriate dissolution profile for an immediate release oral solid dosage form |
| Safety and Efficacy Attributes | Assay: 90 to 110% of label claim<br>Content Uniformity: Meets USP <905><br>Related substances (degradants): Conform to proposed specifications<br>Microbial Quality: Meets USP <61> and USP <62> |
| Patient Compliance | Capsule no larger than size #0 |
| Shelf Life | ≥18 months at room temperature storage conditions |

6.12 Formulation Development and Evaluation

Based upon dog PK study, an enhanced formulation blend (F4-5) containing an acidifier and a surfactant in gelatin capsules (Table 16) was selected as the base formulation for FIH formulation development. A one-month stability study of F4-5 showed no change in the impurity profile after storage at 25° C./60% RH and 40° C./75% RH.

TABLE 16

Composition of Prototype Dog PK Formulation

| Component | Formulation F5 (% w/w) |
|---|---|
| Compound 1 | 13.36 |
| Avicel PH102 | 33.02 |
| Mannitol | 33.02 |
| Citric acid | 10 |
| Sodium lauryl sulfate | 5 |
| Kollidon CL | 4 |
| Colloidal silicon dioxide | 0.6 |
| Stearic acid | 1 |
| Total percent | 100 |
| Total weight (mg) | 200 |
| Capsule strength (mg) | 20 |

6.13 Selection of Dose Strengths and Drug Loadings

The projected clinical dose range is 1 to 150 mg, and three dosage form strengths (1, 5, and 25 mg) were targeted.

A preliminary evaluation of several drug loadings was conducted based on the bulk density and potential dosage unit size of the resulting blends (Table 17). Given the lower limit of capsule fill weight of 75 mg from the processibility perspective, the lowest drug loading was determined to be 1.8% for a dose strength of 1 mg. The desired capsule size is size 1 or below from patient compliance perspective. Therefore, the "common blend" approach was deemed not applicable for dry blending process. As a result, the drug loadings of 6.8% and 22.5% were selected for a dose strength of 5 mg and 25 mg respectively. The low drug loading of 1.800 and the high drug loading of 22.5%0 were evaluated from the chemical stability perspective and the dissolution perspective, respectively, in subsequent formulation development studies.

TABLE 17

Formulation and Dosage Form Characteristics

| Strength (mg) | Drug loading (%) | Bulk density (g/mL) | Target fill weight (mg) | Capsule size | Max fill weight (mg) | % of capsule volume |
|---|---|---|---|---|---|---|
| 1 | 1.8 | 0.44 | 75 | 4 | 92 | 82 |
| 5 | 1.8 | 0.44 | 375 | 00 | 400 | 94 |
| 5 | 6.8 | 0.41 | 100 | 3 | 123 | 81 |
| 25 | 13.5 | 0.32 | 250 | 00 | 291 | 86 |
| 25 | 22.5 | 0.30 | 150 | 1el | 162 | 93 |

6.14 Evaluation of Formulation Stability and Dissolution

The base formulation (Table 16) selected from the animal PK study was optimized in order to achieve the desired formulation stability and dissolution profile. Experiments were performed to determine the appropriate types and levels of excipients to incorporate into the FIH formulation.

6.15 Impact of Excipient Level on Dissolution

Figure 16:
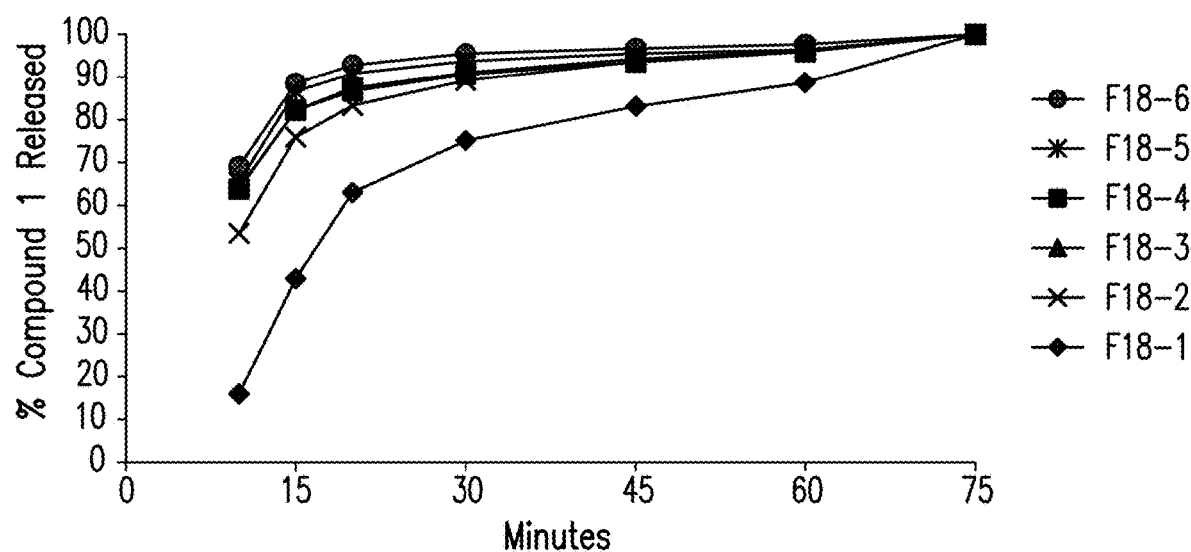
FIG. 16 shows the dissolution profiles of Formulations F18-1 to F18-6 of Table 18 with basket rotation speed at 100 RPM and in pH 6.5 Fasted State Simulated Intestinal Fluid (FaSSIF) as provided in Table 19.
Figure 17:
FIG. 17 shows that Formulations F18-2 and F18-5 containing citric acid and encapsulated in gelatin capsule shells showed capsule brittleness after 3 months at 40° C./75% RH and capsule breakage after 1 month at 50° C./75% RH.

10% citric acid and 5% SLS were used in the base formulation. In order to optimize the level of excipients, six 25 mg formulations in gelatin capsules: F18-1 (conventional) as the control, and varying levels of an acidifier (citric acid—CA) and surfactant (sodium lauryl sulfate—SLS) were prepared (Table 18). Dissolution of each formulation in pH6.5 FaSSIF media was evaluated and the results are listed in Table 19 and plotted in FIG. 16.

TABLE 18

Formulation F18-1-F18-6 Varying Acidifier and Surfactant Levels

| | Formulation (% w/w) | | | | | |
|---|---|---|---|---|---|---|
| Component | F18-1 | F18-2 | F18-3 | F18-4 | F18-5 | F18-6 |
| Compound 1 | | | 22.5 | | | |
| Aerosil 200 | | | 0.6 | | | |
| Crospovidone | | | 4 | | | |
| Magnesium stearate | | | 1 | | | |
| Citric acid, anhydrous | 0 | 0 | 0 | 5 | 10 | 5 |

TABLE 18-continued

Formulation F18-1-F18-6 Varying Acidifier and Surfactant Levels

| Component | Formulation (% w/w) | | | | | |
|---|---|---|---|---|---|---|
| | F18-1 | F18-2 | F18-3 | F18-4 | F18-5 | F18-6 |
| Sodium lauryl sulfate | 0 | 1 | 2.5 | 0 | 5 | 2.5 |
| Avicel PH 102 | 18.0 | 17.7 | 17.4 | 16.7 | 14.2 | 16.1 |
| Mannitol | 54.0 | 53.2 | 52.1 | 50.2 | 42.7 | 48.3 |

TABLE 19

Dissolution comparison F18-1-F18-6
Baskets, 100 RPM, pH 6.5 FaSSIF

| | 10 min | 15 min | 20 min | 30 min | 45 min | 60 min | 75 min |
|---|---|---|---|---|---|---|---|
| % Dissolved (Normalized to 100% at Infinity) in FaSSIF | | | | | | | |
| F1 | 16.0 | 42.9 | 63.0 | 75.1 | 83.1 | 88.7 | 100.0 |
| F2 | 63.8 | 82.2 | 87.4 | 91.0 | 94.2 | 96.3 | 100.0 |
| F3 | 64.0 | 82.2 | 86.7 | 90.6 | 93.5 | 95.9 | 100.0 |
| F4 | 53.5 | 75.9 | 83.3 | 89.2 | 93.6 | 96.3 | 100.0 |
| F5 | 65.4 | 86.6 | 90.8 | 93.7 | 95.5 | 96.4 | 100.0 |
| F6 | 69.1 | 88.5 | 92.8 | 95.5 | 96.7 | 97.7 | 100.0 |
| % Dissolved (as is) in FaSSIF | | | | | | | |
| F1 | 13.7 | 36.8 | 54.0 | 64.4 | 71.2 | 76.0 | 85.7 |
| F2 | 57.0 | 73.2 | 77.3 | 80.8 | 83.4 | 85.4 | 89.1 |
| F3 | 57.7 | 74.4 | 79.0 | 82.4 | 85.2 | 87.1 | 90.5 |
| F4 | 46.7 | 66.3 | 72.7 | 77.8 | 81.7 | 84.0 | 87.3 |
| F5 | 60.9 | 80.7 | 84.6 | 87.3 | 89.0 | 89.8 | 93.2 |
| F6 | 60.9 | 78.0 | 81.8 | 84.1 | 85.3 | 86.2 | 88.2 |

Dissolution conditions: 900 mL FaSSIF, apparatus I (basket), 100 rpm. FaSSIF=fasted-state simulated intestinal fluid (pH 6.5 and contains 3 mM Sodium Taurocholate, 0.75 mM Lecithin).

The slowest dissolution was the conventional formulation (F18-1) without acidifier or surfactant. F18-6 (5% CA and 2.5% SLS) had the fastest release profile, slightly faster than F18-5 (5% CA and 5% SLS). Both showed faster release than F18-2 (1% SLS), F18-3 (2.5% SLS), and F18-4 (5% CA), indicating a synergistic effect of the acidifier in combination with the surfactant on drug dissolution. The release profiles with the surfactant level of 1% was comparable to that with 5% SLS. Therefore, a base formulation containing 5% CA and 1% SLS was selected for subsequent formulation development studies.

6.16 Stability Studies with Various Diluents, Acidifiers, Antioxidants, and Lubricants Stability studies evaluating the various components of the formulation were studied.

Citric acid (CA) and stearic acid (SA) showed degradation in the excipient compatibility study. Therefore, alternative acidifiers and lubricants were evaluated to mitigate potential stability risks. Formulation F20-1 (conventional) is the control; and 8 additional formulations were prepared. F20-2 contains CA+SLS; F20-3 and F20-4 include either butylated hydroxytoluene (BHT) or sodium metabisulfite (SMB) as an antioxidant; F20-5 and F20-6 contain either CA or SLS; F20-7 includes an alternative acidifier (fumaric acid); F20-8 and F20-9 include an alternative lubricant stearic acid or sodium stearyl fumarate (SA or SSF).

Formulation compositions are listed in Table 20. Formulations were encapsulated into hard gelatin capsules. Capsules were packaged in heat-induction sealed HDPE bottles (7 count per bottle) and staged on stability at 50° C./75% RH.

TABLE 20

1 mg Formulation Component Screening Composition and Function

| Component | Formulation (% w/w) | | | | | | | | |
|---|---|---|---|---|---|---|---|---|---|
| | F20-1 | F20-2 | F20-3 | F20-4 | F20-5 | F20-6 | F20-7 | F20-8 | F20-9 |
| Compound 1 | | | | | 1.84 | | | | |
| Disintegrant: Crospovidone | | | | | 4 | | | | |
| Glidant: Aerosil 200 | | | | | 0.6 | | | | |
| Diluent: Avicel PH102 | 23.14 | 21.64 | 21.62 | 21.62 | 21.89 | 22.89 | 21.89 | 21.64 | 21.64 |
| Diluent: Mannitol | 69.42 | 64.92 | 64.85 | 64.85 | 65.67 | 68.67 | 65.67 | 64.92 | 64.92 |
| Solubilizer: SLS | 0 | 1 | 1 | 1 | 0 | 1 | 0 | 1 | 1 |
| Acidifier | | | | | | | | | |
| Citric acid | 0 | 5 | 5 | 5 | 5 | 0 | 0 | 5 | 5 |
| Fumaric acid | 0 | 0 | 0 | 0 | 0 | 0 | 5 | 0 | 0 |
| Antioxidant | | | | | | | | | |
| Butylated hydroxytoluene | 0 | 0 | 0.1 | 0 | 0 | 0 | 0 | 0 | 0 |
| Sodium metabisulfite | 0 | 0 | 0 | 0.1 | 0 | 0 | 0 | 0 | 0 |
| Lubricant | | | | | | | | | |
| Magnesium stearate | 1 | 1 | 1 | 1 | 1 | 1 | 1 | 0 | 0 |
| Stearic acid | 0 | 0 | 0 | 0 | 0 | 0 | 0 | 1 | 0 |
| Sodium stearyl fumarate | 0 | 0 | 0 | 0 | 0 | 0 | 0 | 0 | 1 |

SLS = sodium lauryl sulfate.

6.17 Assessment of Compound 1 Form Conversion

Formulations were assessed by X-ray powder diffraction (XRPD) initially and after 1 month storage at 50° C./75% RH to evaluate for Compound 1 polymorphic form conversion or disproportionation of the citrate salt (Table 21).

citric acid. RRT 0.88 degradation product formula by mass spectrometry is $C_{24}H_{26}C_3N_7O_2$. This corresponds to a loss of hydrogen fluoride. This impurity has been observed in alkaline conditions.

No degradation was observed in formulation (F20-2).

TABLE 22

Stability % Impurity Results for 1 mg Formulations 1-9

| Time | Initial % impurity | | | | | | | | |
|---|---|---|---|---|---|---|---|---|---|
| Formulation | F20-1 | F20-2 | F20-3 | F20-4 | F20-5 | F20-6 | F20-7 | F20-8 | F20-9 |
| RRT 0.88 | | | | | | | | | |
| Des-F 91516 | 0.52 | 0.51 | 0.52 | 0.5 | 0.52 | 0.52 | 0.51 | 0.51 | 0.51 |
| CC-20048 | 0.36 | 0.36 | 0.36 | 0.36 | 0.36 | 0.36 | 0.36 | 0.36 | 0.36 |
| RRT 1.10 | | | | 0.13 | | | | | |
| Bis-F 91516 | 0.32 | 0.32 | 0.32 | 0.32 | 0.32 | 0.32 | 0.32 | 0.32 | 0.32 |
| Total Imps | 1.2 | 1.2 | 1.2 | 1.3 | 1.2 | 1.2 | 1.2 | 1.2 | 1.2 |

| Time | 1 month at 50° C./75% RH | | | | | | | | |
|---|---|---|---|---|---|---|---|---|---|
| Formulation | F1 | F2 | F3 | F4 | F5 | F6 | F7 | F8 | F9 |
| RRT 0.88 | 0.15 | | | | | 0.31 | 0.09 | | |
| Des-F 91516 | 0.52 | 0.52 | 0.52 | 0.52 | 0.52 | 0.52 | 0.52 | 0.52 | 0.52 |
| CC-20048 | 0.36 | 0.37 | 0.36 | 0.36 | 0.36 | 0.37 | 0.36 | 0.36 | 0.36 |
| RRT 1.10 | | | | | | | | | |
| Bis-F 91516 | 0.32 | 0.32 | 0.32 | 0.33 | 0.33 | 0.32 | 0.33 | 0.32 | 0.32 |
| Total Imps | 1.4 | 1.2 | 1.2 | 1.2 | 1.2 | 1.5 | 1.3 | 1.2 | 1.2 |

Note:
Only peaks ≥ quantitation level reported.

Disappearance of drug peaks at the lower diffraction angles was observed, but a form change from Form B to Form A or salt disproportionation is challenging to detect at the 1.84% drug loading level. XRPD was also performed on higher DL conventional and enhanced formulations (22% DL). No evidence was observed of form change or salt disproportionation.

TABLE 21

Summary of XRPD Results for F1-F9

| Sample | Initial | 1 month (50° C./75% RH) |
|---|---|---|
| 8204-014-F1 | Crystalline | No Major Changes (peak at 5.5° 2θ disappears) |
| 8204-014-F2 | Crystalline | Drug peaks disappear |
| 8204-014-F3 | Crystalline | Drug peaks disappear |
| 8204-014-F4 | Crystalline | Drug peaks disappear and peak at 26.1° 2θ diminishes significantly |
| 8204-014-F5 | Crystalline | Drug peaks disappear |
| 8204-014-F6 | Crystalline | Drug peaks disappear |
| 8204-014-F7 | Crystalline | Peaks at 5.5 and 28.8° 2θ disappear |
| 8204-014-F8 | Crystalline | Drug peaks disappear |
| 8204-014-F9 | Crystalline | Drug peaks disappear |

Note:
Major Compound 1 Form B peaks that are readily distinguishable are three peaks between 4° and 7° 2θ.

6.18 Capsule Appearance

Capsule appearance was evaluated after 1 month storage at 50° C./75% RH. All the formulations containing CA showed significant capsule shell breakage. Citric acid is hygroscopic, and it was suspected that the moisture uptake results in brittleness of capsule shells.

6.19 Chemical stability

Degradation (RRT 0.88) was only observed for formulations F20-1, F20-6, F20-7 after 1 month storage at 50° C./75% RH (Table 22). These formulations do not contain 6.20 Stability Studies with Two Acidifiers and HPMC/Gelatin Capsule Shells Five 1 mg formulations encapsulated in gelatin or hydroxypropyl methylcellulose (PMC) capsule shells were manufactured and evaluated for stability. F20-2, F20-5, F20-6, and F20-7 were previously described in Table 20: Anew formulation, F23-14, contains the acidifier fumaric acid (FA), which was substituted for citric acid. The formulations are listed in Table 23.

TABLE 23

Composition of 1 mg Formulations

| | Formulation (% w/w) | | | | |
|---|---|---|---|---|---|
| Component | F20-2 | F20-5 | F20-6 | F20-7 | F23-14 |
| Compound 1 | | | 1.84 | | |
| Crospovidone | | | 4 | | |
| Aerosil 200 | | | 0.6 | | |
| Magnesium stearate | | | 1 | | |
| Avicel PH102 | 21.64 | 21.89 | 22.89 | 21.89 | 21.64 |
| Mannitol | 64.92 | 65.67 | 68.67 | 65.67 | 64.92 |
| Acidifier | | | | | |
| Citric acid | 5 | 5 | 0 | 0 | 0 |
| Fumaric acid | 0 | 0 | 0 | 5 | 5 |
| Sodium lauryl sulfate | 1 | 0 | 1 | 0 | 1 |

Capsule appearance and formation of degradation product RRT 0.88 were monitored for stability, and results up to 3 months are provide in Table 24.

Formulations F20-2 and F20-5 containing citric acid and encapsulated in gelatin capsule shells showed capsule brittleness after 3 months at 40° C./75% RH and capsule breakage after 1 month at 50° C./75% RH. No change in appearance was noted for any other formulation of capsule shell.

Formulation F6 containing SLS and no acidifier had the highest level of RRT 0.88 degradation product. Addition of acidifier improved the chemical stability. F23-14 (FA+SLS) formulation showed lower levels of RRT 0.88 than F20-2 (CA+SLS) formulation.

F23-14 (FA+SLS) and F20-7 (FA) in HPMC and gelatin shells, and F20-5 (CA) in HPMC shells showed acceptable accelerated stability results.

TABLE 24

Stability Results for 1 mg Formulations

| Formulation | Shell | % RRT 0.88 degradation product | | | | Capsule appearance | |
|---|---|---|---|---|---|---|---|
| | | 40° C./75% RH | | 50° C./75% RH | | 40° C./ 75% RH | 50° C./ 75% RH |
| | | 1 Mo | 3 Mo | 1 Mo | 2 Mo | 3 Mo | 1 Mo |
| F2 | HPMC | 0.02 | 0.06 | 0.11 | 0.17 | No Change | No Change |
| (CA + SLS) | Gelatin | 0 | 0.04 | 0 | NT | Brittle | Breakage |
| F5 | HPMC | 0 | 0.03 | 0.05 | 0.08 | No Change | No Change |
| (CA) | Gelatin | 0 | 0.03 | 0 | NT | Brittle | Breakage |
| F6 | HPMC | 0.04 | 0.17 | 0.2 | 0.40 | No Change | No Change |
| (SLS) | Gelatin | 0.03 | 0.13 | 0.31 | NT | No Change | No Change |
| F7 | HPMC | 0 | 0 | 0 | 0.02 | No Change | No Change |
| (FA) | Gelatin | 0 | 0 | 0.09 | NT | No Change | No Change |
| F14 | HPMC | 0 | 0 | 0.02 | 0.03 | No Change | No Change |
| (FA + SLS) | Gelatin | 0 | 0 | 0.03 | 0.03 | No Change | No Change |

CA = citric acid;
FA = fumaric acid;
NT = not tested;
SLS = sodium lauryl sulfate.

An accelerated stability assessment program (ASAP) was performed on formulations blends F23-14 (FA+SLS) and F20-5 (CA) (Table 25). Formulation F23-14 demonstrated lower levels of RRT 0.88 degradation product throughout study.

TABLE 25

ASAP Stability Conditions and RRT 0.88 Degradation Product Levels

| Sample | Time (Days) | Storage Condition | % RRT 0.88 | |
|---|---|---|---|---|
| | | | F5—CA | F14—FA + SLS |
| 1 | 0 | Initial | ND | ND |
| 2 | 0 | | ND | ND |
| 3 | 8 | 52° C./60% RH | ND | ND |
| 4 | 14 | | 0.02 | ND |
| 5 | 7 | 60° C./11% RH | 0.01 | ND |
| 6 | 14 | | 0.01 | ND |
| 7 | 1 | 70° C./28% RH | ND | ND |
| 8 | 11 | | 0.13 | 0.02 |
| 9 | 1 | 69° C./81% RH | 0.04 | 0.02 |
| 10 | 2 | | 0.06 | 0.05 |
| 11 | 1 | 79° C./9% RH | 0.02 | ND |
| 12 | 7 | | 0.14 | 0.04 |
| 13 | 3 | 49° C./85% RH | ND | ND |
| 14 | 14 | | 0.01 | 0.02 |
| 15 | 1 | 79° C./49% RH | 0.10 | 0.05 |
| 16 | 2 | | 0.18 | 0.07 |

A humidity corrected Arrhenius equation (i.e., ASAP Prime version 4.0.1) was used to assess the stability results. Activation energy (Ea) and the moisture sensitivity (B) to degradation were assessed and are listed in Table 26. B term demonstrated that the formulations have a low to moderate sensitivity to moisture mediated degradation. The activation energy of both formulations were equivalent to lower than other tested formulations (average 27 kcal/mole for 69 formulations tested), and in combination should lead to a stable dosage form. This is borne out with the high probability of meeting proposed shelf life under various scenarios. Based on the model prediction, F23-14 was expected to demonstrate long-term stability at 25° C./60% RH, with or without desiccant.

TABLE 26

Degradation Kinetics and Shelf Life Probability

| Parameter | F20-5 (CA) | F23-14 (FA + SLS) |
|---|---|---|
| Activation Energy ($E_a$, kcal/mol)[a] | 36.8 kcal/mol | 27.2 kcal/mol |
| Moisture Sensitivity Coefficient (B)[b] | 0.025 | 0.032 |
| Correlation Coefficient ($R^2$) | 0.987 | 0.918 |
| Probability of passing specification | | |
| 1.0% Spec at 25° C./60% RH, 3 years | 100.00 | 99.95 |
| 1.0% Spec at 40° C./75% RH, 6 months | 100.00 | 100.00 |
| 1.0% Spec at 25° C./60% RH, 3 years, 1.0 g of Desiccant | 100.00 | 99.99 |
| 1.0% Spec at 40° C./75% RH, 6 months, 1.0 g of Desiccant | 100.00 | 100.00 |
| 0.20% Spec at 25° C./60% RH, 3 years | 99.90 | 96.86[d] |
| 0.20% Spec at 40° C./75% RH, 6 months | 99.97 | 96.24 |
| 0.20% Spec at 25° C./60% RH, 3 years, 1.0 g of Desiccant | 99.67 | 99.36 |
| 0.20% Spec at 40° C./75% RH, 6 months, 1.0 g of Desiccant | 99.98 | 99.93 |

CA = citric acid;
FA = Fumaric acid;
SLS = sodium lauryl sulfate
[a]Average activation energy of an impurity is 27 kcal/mol
[b]Average moisture sensitivity coefficient of an impurity is 0.034
[c]Probability of passing specification
[d]Decrease in probability of meeting specification is likely caused by poor model fit (too little degradation during study to appropriately model the data)

Simulations assumed 7 count in a 100 cc HDPE bottle which was heat induction sealed.

6.21 Dissolution of High Drug Load Formulations F10, F12, F13, F15, F16

Five high drug loading (23%) 25 mg formulations were prepared and filled into gelatin capsules. F27-10 (CA+SLS) and F27-11 (conventional) were the controls; and 4 additional formulations were prepared. F27-12 and F27-16 contained either CA or FA; F27-13 contained sodium lauryl sulfate; F27-15 was the same as F10, with FA in place of CA.

Formulation compositions are listed in Table 27. The capsules were tested using apparatus I (baskets) at 100 RPM.

TABLE 27

Compositions of 25 mg Formulations

| | Formulation (% w/w) | | | | | |
|---|---|---|---|---|---|---|
| Component | F27-10 | F27-11 | F27-12 | F27-13 | F27-15 | F27-16 |
| API | | | 23.02 | | | |
| Crospovidone | | | 4 | | | |
| Aerosil 200 | | | 0.6 | | | |
| Magnesium Stearate | | | 1 | | | |
| Avicel PH102 | 16.35 | 17.85 | 16.60 | 17.60 | 16.35 | 16.60 |
| Mannitol | 49.04 | 53.54 | 49.79 | 52.79 | 49.04 | 49.79 |
| Citric acid | 5 | 0 | 5 | 0 | 0 | 0 |
| SLS | 1 | 0 | 0 | 1 | 1 | 0 |
| Fumaric acid | 0 | 0 | 0 | 0 | 5 | 5 |
| Fill Weight (mg) | | | 150 | | | |

SLS = sodium lauryl sulfate

Figure 18:
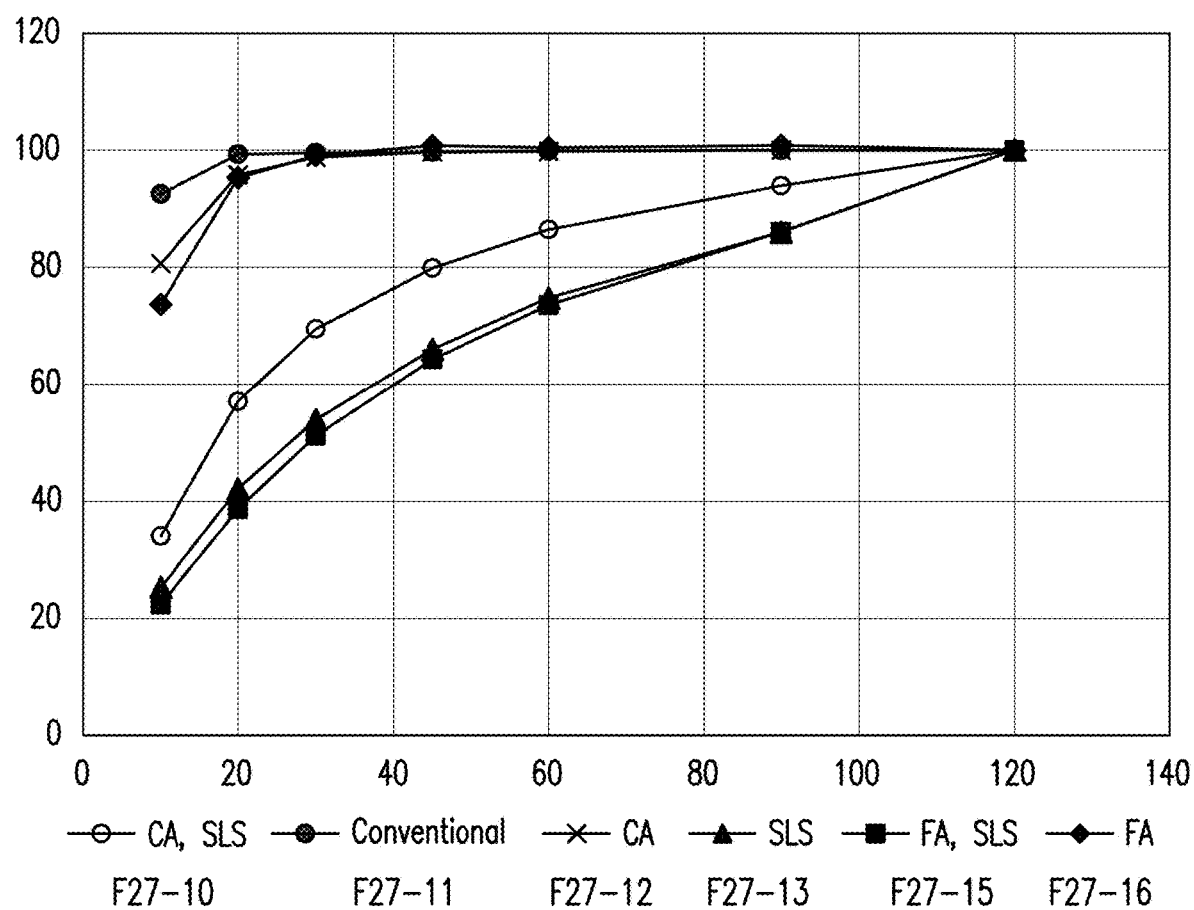
FIG. 18 shows the release profiles of each formulation in Table 27 in 0.1 N HCl.
Figure 19:
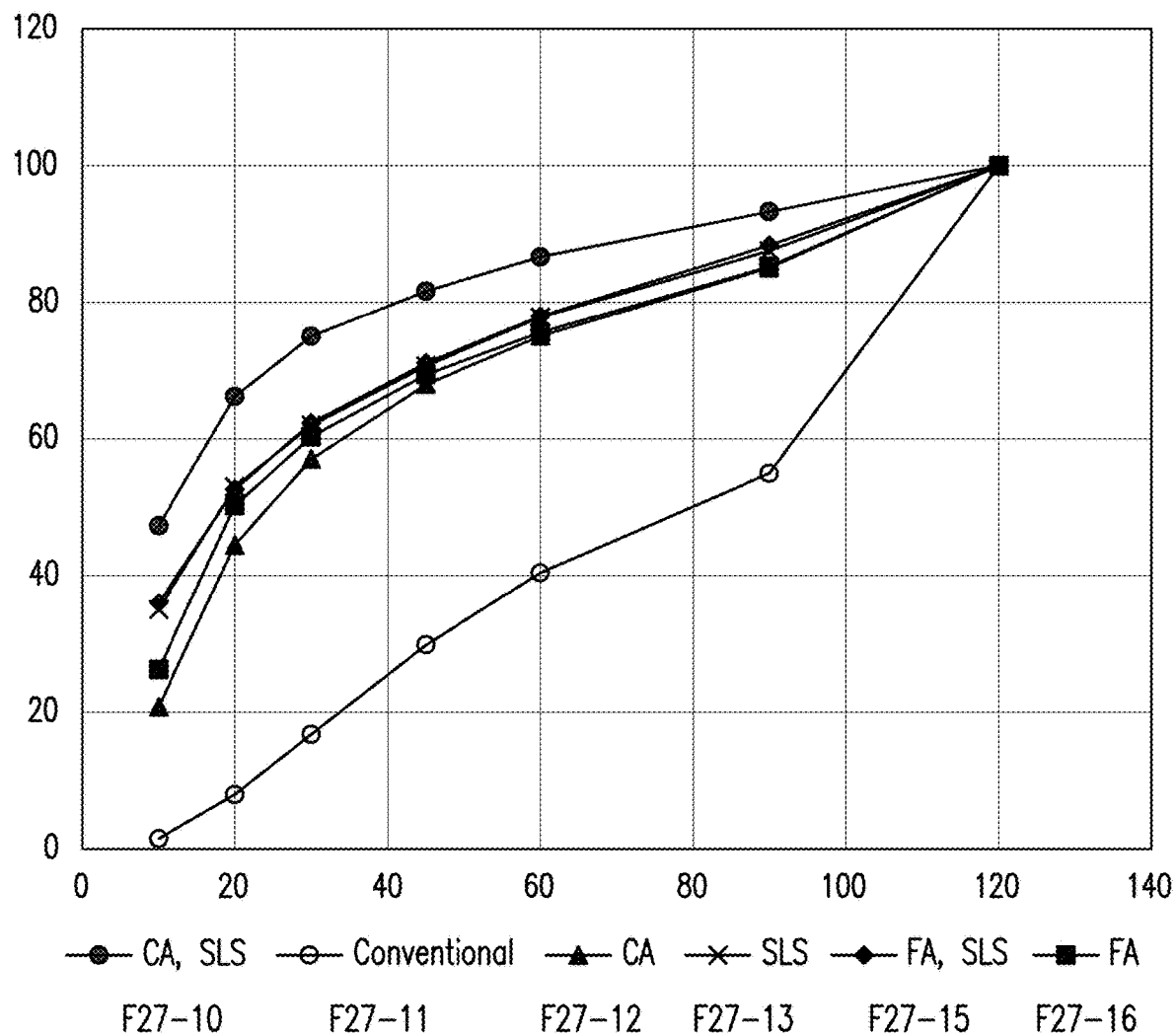
FIG. 19 shows the release profiles of each formulation in Table 27 in pH 4.5 acetate buffer (50 mM).
Figure 20:
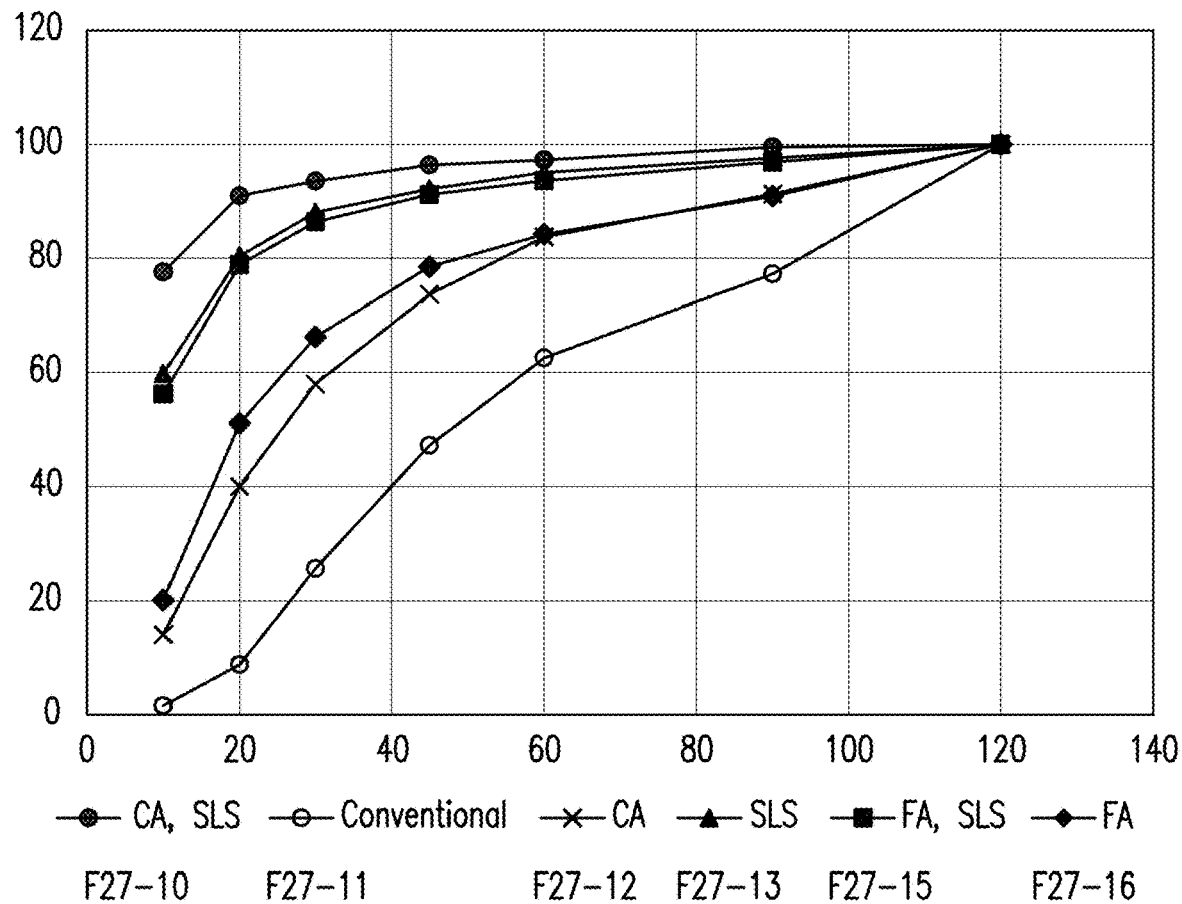
FIG. 20 shows the release profiles of each formulation in Table 27 in pH 6.8 phosphate buffer (50 mM).

The release profiles of each formulation in 0.1 N HCl (FIG. 18), pH 4.5 acetate buffer (50 mM) (FIG. 19), and pH 6.8 phosphate buffer (50 mM) (FIG. 20) are provided.

At low pH, Compound 1 was soluble (~1.7 mg/mL). The formulations were grouped, with the conventional (F27-11) releasing slightly faster than formulations containing just FA (F27-16) or CA (F27-12). The formulations containing SLS were similarly grouped with F27-10 (CA+SLS) releasing faster than F27-13 (SLS), which had a similar release profile to F27-15 (FA+SLS).

At pH 4.5, Compound 1 (pKa ~5.1) was less soluble (~0.25 mg/mL) than in more acidic media. The formulations were grouped, with the enhanced formulations releasing faster than the conventional formulation. For the enhanced formulations, F27-10 (CA+SLS) released faster than F27-15 (FA+SLS) and F27-13 (SLS), which released slightly faster than the FA (F27-16) and CA (F27-12) formulations.

At pH 6.8, Compound 1 had low solubility (0.002 mg/mL at pH 7.3). The formulations were grouped in the same order as pH 4.5, however the spacing between the groups was larger. For the enhanced formulations, F27-10 (CA+SLS) released faster than F27-15 (FA+SLS) and F27-13 (SLS), which released faster than FA (F27-16) and CA (F27-12) formulations.

SLS containing formulations had the slowest release rate at low pH, and the fastest release at pH 6.8. The release profiles were slightly faster for the SLS formulations at pH 4.5 when compared to low pH media. SLS is anionic and Compound 1 (pKa ~5.1) is cationic in acidic media. It is possible that an ionic interaction is occurring between SLS and the drug substance, creating a neutral species that suppresses the release rate for these formulations.

Figure 21:
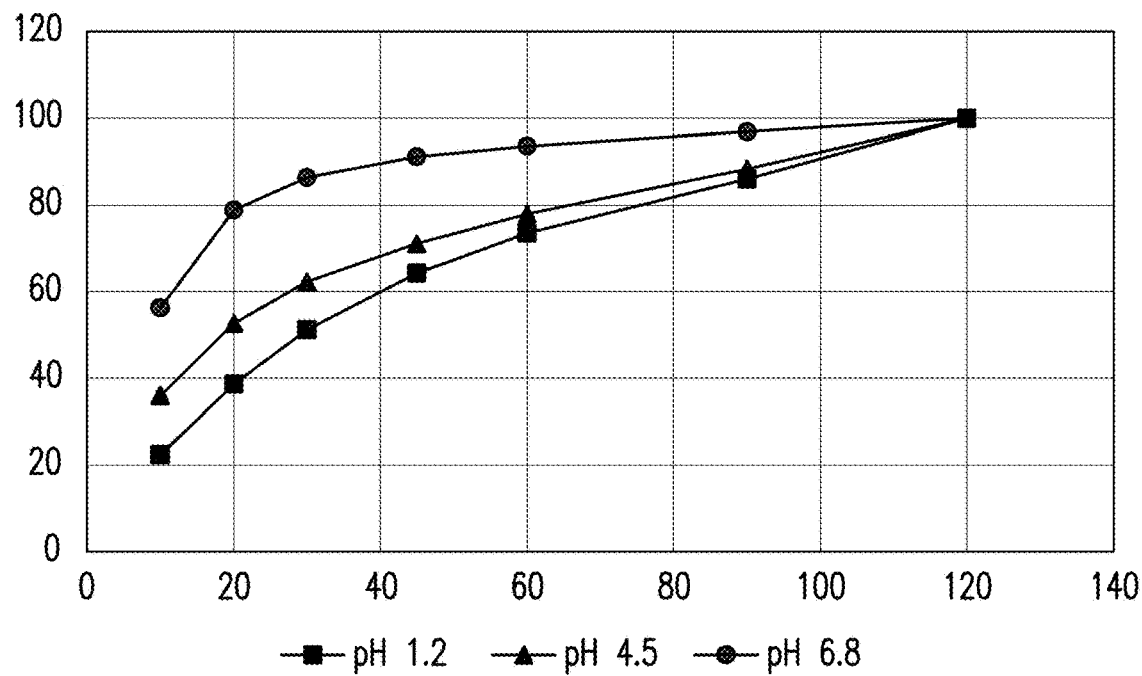
FIG. 21 shows the dissolution profiles of the 25 mg enhanced formulation (F27-15, Table 27) with apparatus I at 100 RPM in 0.1N HCl, pH 4.5 acetate buffer and pH 6.8 phosphate buffer.

Dissolution profiles of the 25 mg enhanced formulation (FA+SLS) (F27-15, Table 27) with apparatus I at 100 RPM in 0.1N HCl, pH 4.5 acetate buffer and pH 6.8 phosphate buffer is shown in FIG. 21.

Figure 22:
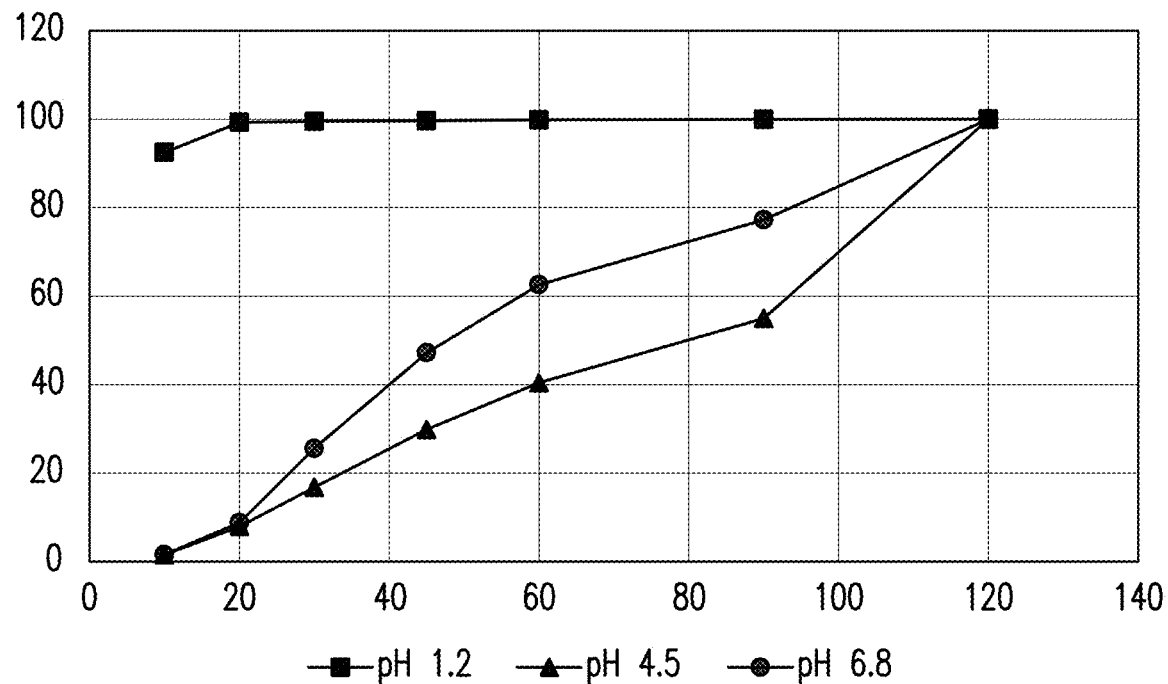
FIG. 22 shows the dissolution profiles of a conventional formulation (F4-1 in Table 11) with apparatus I at 100 RPM in 0.1N HCl, pH 4.5 acetate buffer and pH 6.8 phosphate buffer.

The same dissolution conditions were used to evaluate a conventional formulation for comparison, and the profiles are shown in FIG. 22. A comparison of the profiles showed that the enhanced FIH formulation had a consistent release profile, and had less variability as a function of pH compared to a conventional formulation.

At pH 4.5 and 6.8, the non-SLS containing formulations had a much slower release than at low pH. The combination of acidifier and SLS provided the fastest dissolution at medium and neutral pH and moderate dissolution at low pH.

6.22 Evaluation of Capsule Shell Composition on Dissolution

Formulation F27-15 in Table 27 encapsulated in HPMC and gelatin shells were evaluated at pH 6.8, with and without the addition of 0.05% SLS into the dissolution media.

Figure 23:
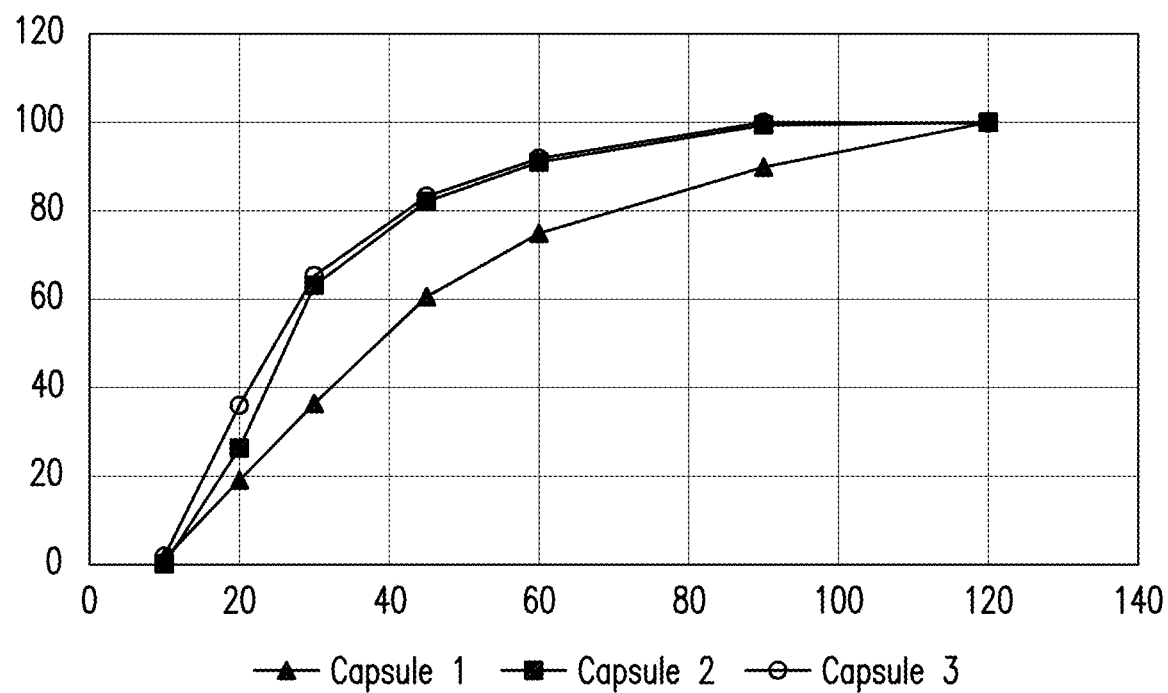
FIG. 23 shows high variability in dissolution of enhanced formulation (F27-15, Table 27) with HPMC capsule shells (25 mg strength) at neutral pH.
Figure 24:
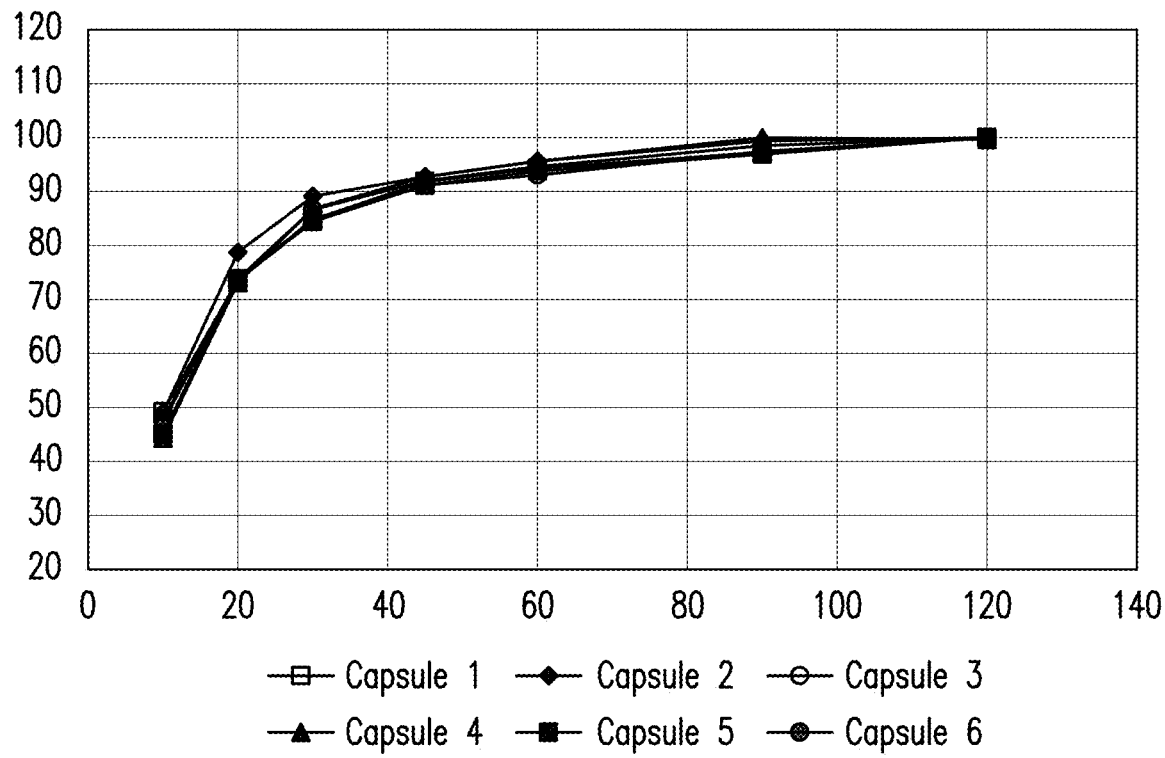
FIG. 24 shows that no variability was observed in dissolution of enhanced formulation (F27-15, Table 27) with gelatin capsule shells (25 mg strength) at neutral pH.

At neutral pH, high variability in dissolution of Formulation F27-15 in Table 27 was observed in FA+SLS formulation with HPMC capsule shells (25 mg strength) (FIG. 23), but not with gelatin capsule shells (FIG. 24).

Figure 25:
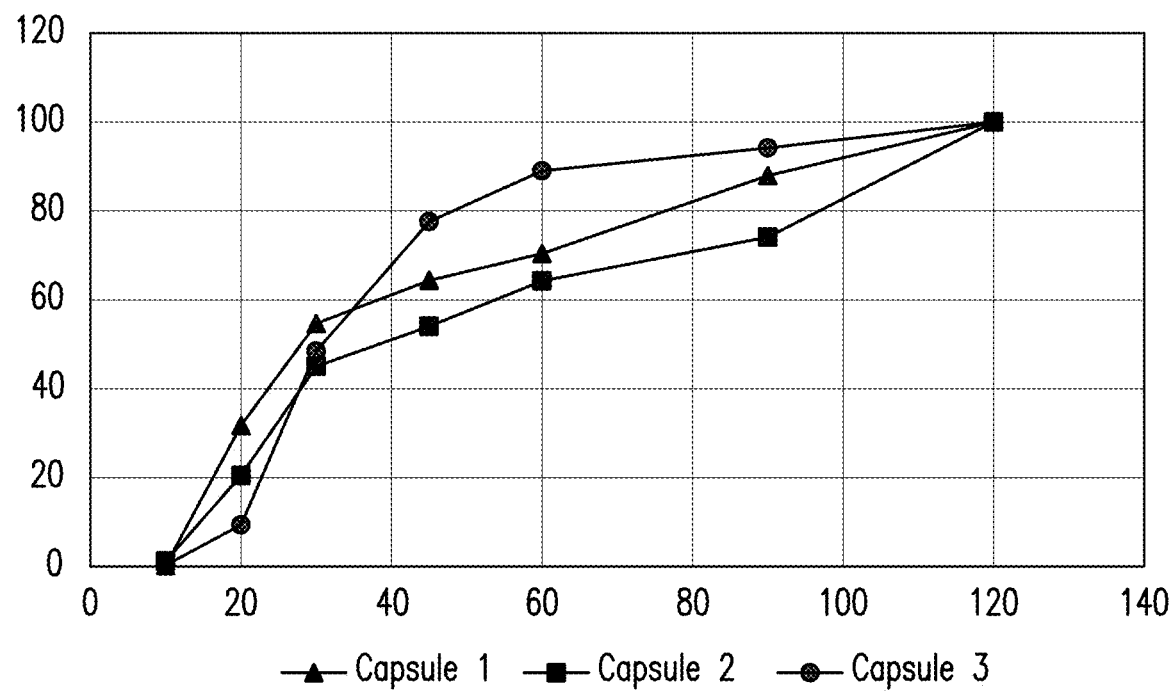
FIG. 25 shows high variability in dissolution of enhanced formulation (F27-15, Table 27) with HPMC capsule shells (25 mg strength) at neutral pH in the dissolution media with 0.5% SLS.
Figure 26:
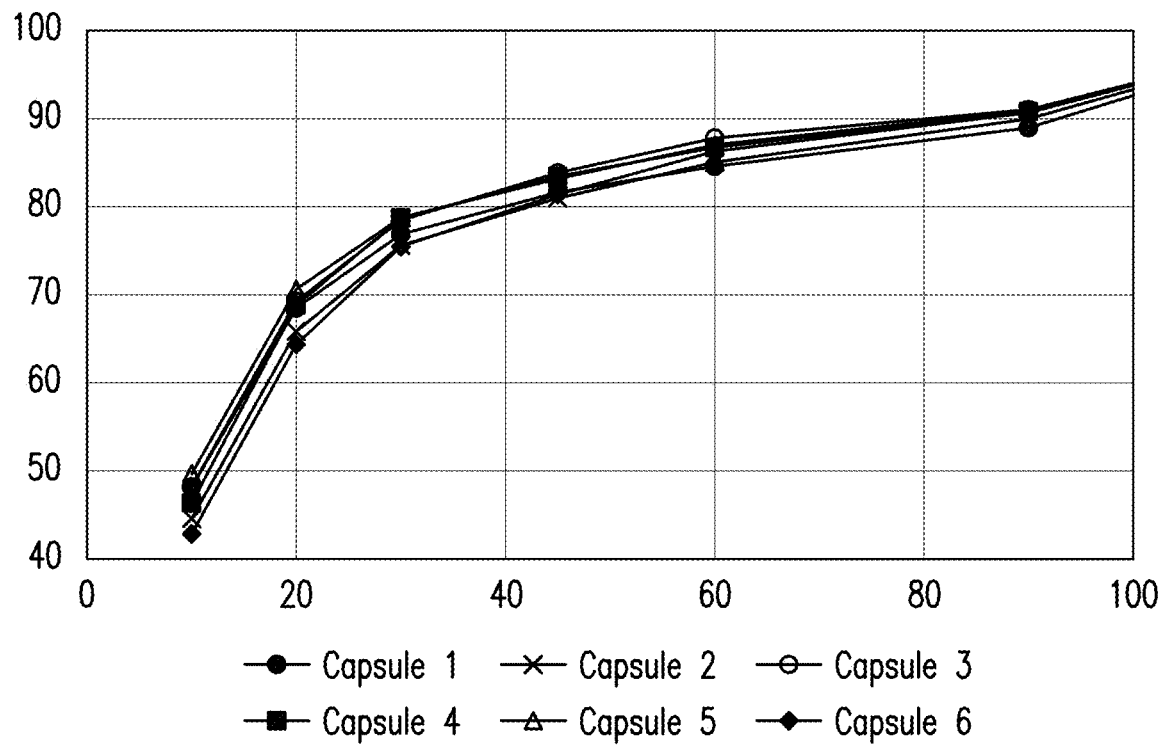
FIG. 26 shows that no variability was observed in dissolution of enhanced formulation (F27-15, Table 27) with gelatin capsule shells (25 mg strength) at neutral pH in the dissolution media with 0.5% SLS.

0.5% SLS was added to the dissolution media, and high dissolution variability of Formulation F27-15 in Table 27 continued to be observed in FA+SLS formulation with HPMC capsule shells (FIG. 25), but not with gelatin capsule shells (FIG. 26).

Figure 27:
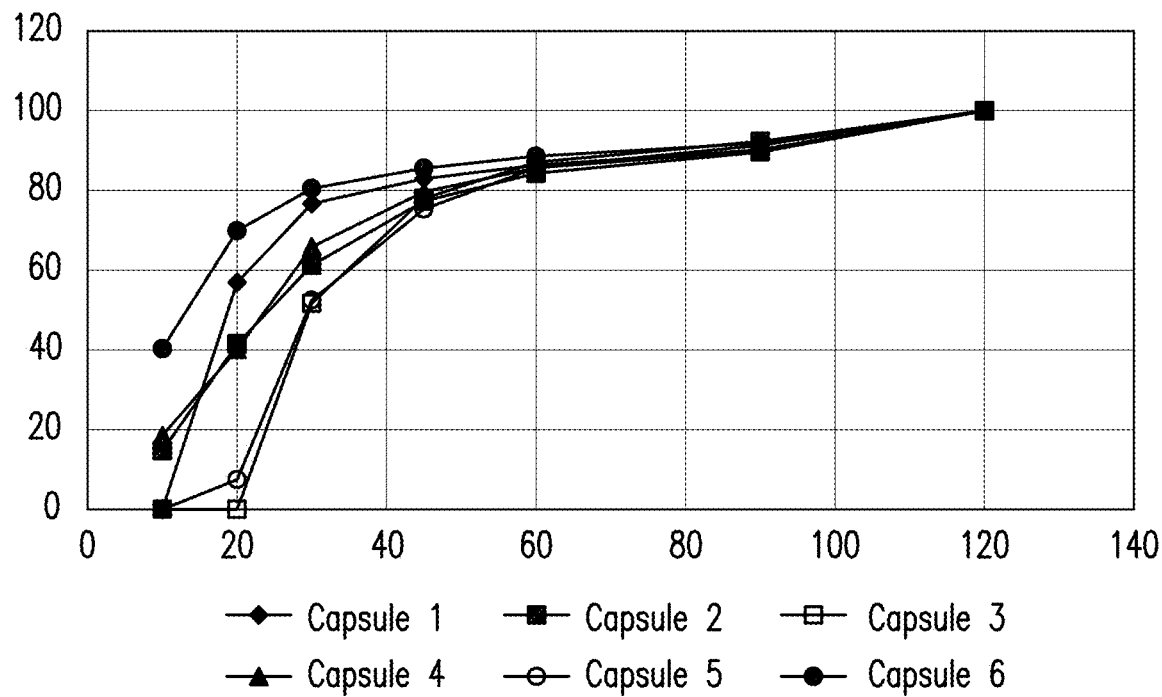
FIG. 27 shows that the SLS only formulation (F27-13 in Table 27) behaved similarly in HPMC capsule shells in the dissolution media with 0.5% SLS and without 0.5% SLS.
Figure 28:
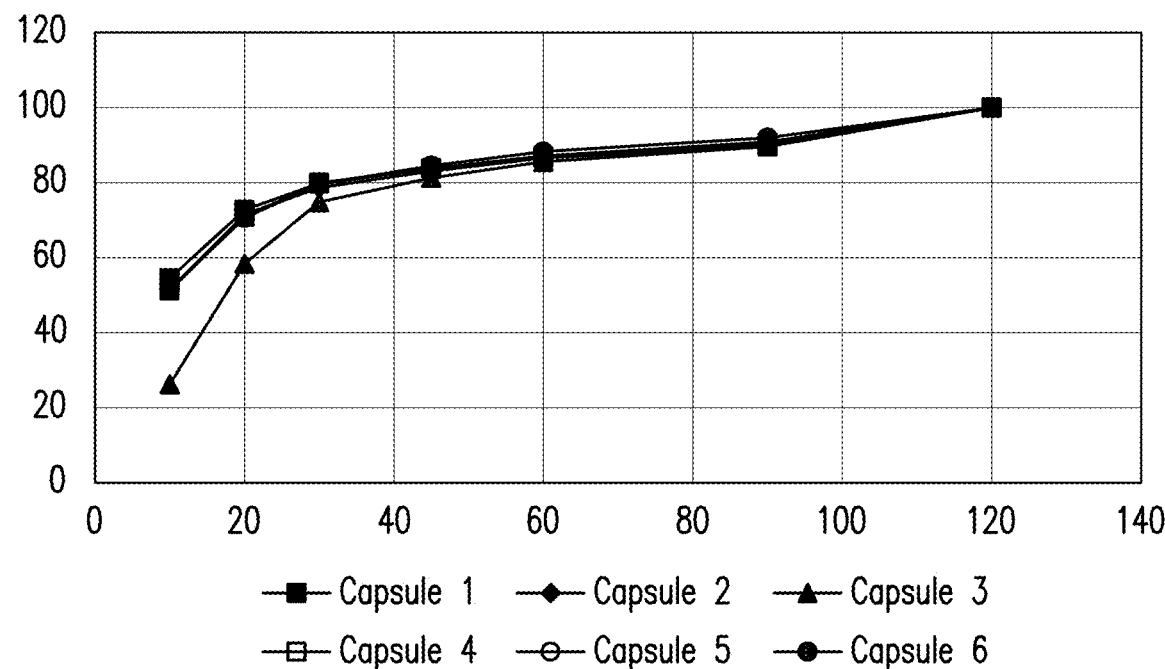
FIG. 28 shows that the SLS only formulation (F27-13 in Table 27) behaved similarly in gelatin capsule shells in the dissolution media with 0.5% SLS and without 0.5% SLS.
Figure 29:
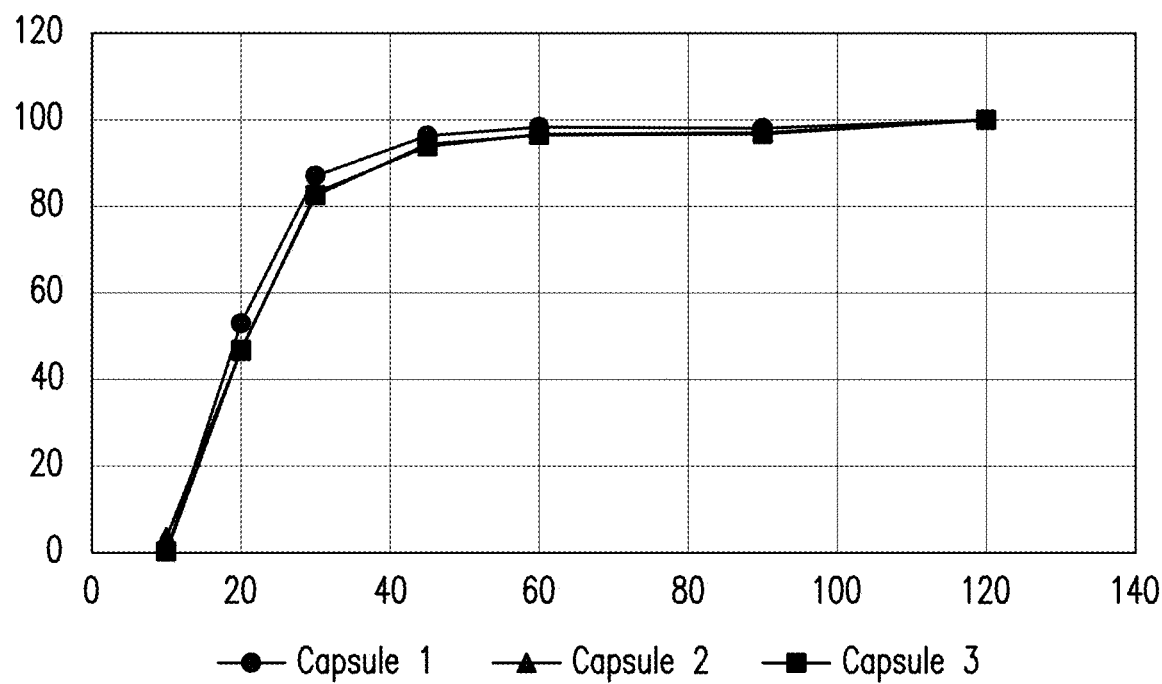
FIG. 29 shows that the CA+SLS formulation (F27-10 in Table 27) behaved differently in HPMC capsule shells in the dissolution media with 0.5% SLS and without 0.5% SLS.

The SLS only formulation (F27-13 in Table 27) behaved similarly (HPMC: FIG. 27, gelatin: FIG. 28), however this phenomenon was not observed in CA+SLS formulation (F27-10 in Table 27) in HPMC (FIG. 29).

It was suspected that interaction between FA, SLS, and HPMC capsule shells resulted in the varied drug release.

Figure 30:
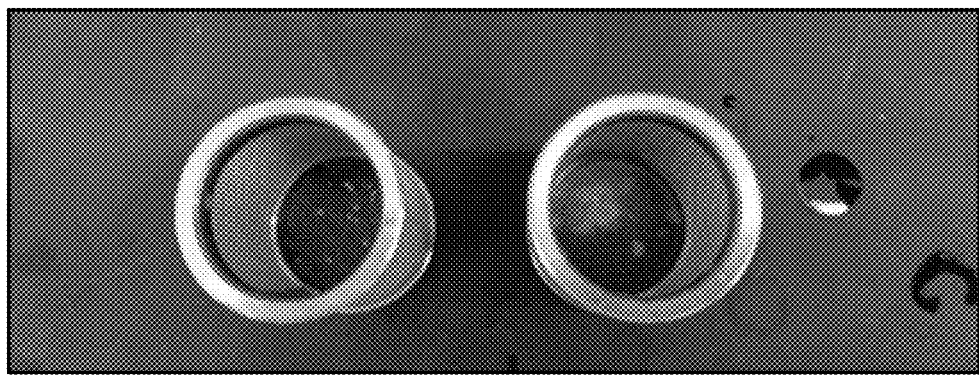
FIG. 30 shows that HPMC capsules retained gel-like and lumpy residual solids in the basket at the end of dissolution.

At the end of dissolution, HPMC capsules retained gel-like, lumpy residual solids in the basket. See FIG. 30. If these gelatinous materials entrapped Compound 1, variable dissolution profiles could result.

6.23 Results

Based on the stability and dissolution result, Formulation F27-15 in Table 27 which contained 5% fumaric acid and 1% SLS and filled in hard gelatin capsule shells had the best overall stability and dissolution characteristics.

6.24 Process Development and Evaluation

The physical properties of the drug substance such as particle size, shape, and surface characteristics can play a role in the manufacturability of the formulation. Compound 1 (citrate salt form B) crystallized in a needle shape.

Needle-like particle shapes have poor powder flow and low densities. Compound 1 had a bulk density of 0.2 g/mL and a tap density 0.38 g/mL. Reduced drug loadings (dilution of the poor flow component) improved flow characteristics of the resultant blend. The flowability of six conventional formulations has been listed in Table 28.

TABLE 28

Flowability Assessment of Six Prototype Formulation Blends

| | Formulation (% w/w) | | | | | |
|---|---|---|---|---|---|---|
| Component | F28-1 | F28-2 | F28-3 | F28-4 | F28-5 | F28-6 |
| Compound 1 | 1.8 | 6.74 | 13.48 | 22.46 | 22.46 | 22.46 |
| Avicel PH102 | 46.3 | 43.83 | 40.46 | 35.97 | 23.98 | 23.98 |
| Mannitol | 46.3 | 43.83 | 40.46 | 35.97 | 47.96 | |
| Lactose | | | | | | 47.96 |
| Crospovidone | | | 4 | | | |
| Aerosil 200 | | | 0.6 | | | |
| Magnesium Stearate | | | 1 | | | |
| FFC | 11.6 | 5.9 | 3.2 | 2.5 | 2.5 | 2.5 |

FFC = flow function coefficient.

Flow function coefficients (FFC) were measured by ring shear. FFC values greater than 5 had good flow properties. Formulations F28-1 and F28-2 were assessed to have good flow properties. The FFC value is directly related to drug loading (F28-1<F28-2<F28-3<F28-4-F28-6). Changing the ratio of Avicel to Mannitol (F28-4 vs. F28-5) or replacing mannitol with lactose (F28-5 vs. F28-6) did not impact flowability.

6.25 600 g Manufacturing Trial 1

Five formulations of various drug loadings were developed (Table 29) to cover the anticipated FIH dose range.

For a 1 mg dose, and a 75 mg weight, the resulting drug load was calculated to be 1.8%. For the 5 mg dose, a fill weight of 100 mg resulted in a drug loading of 6.9%. For the 25 mg dose, a fill weight of 150 mg resulted in a drug load of 23%. Based on the poor flow properties for high drug loading formulations (FFC=2.5, Table 28) a lower DL (13.81%, corresponding to 250 mg fill weight) was also evaluated. A 20 mg dose was also developed, and a fill weight of 250 mg resulted in a drug loading of 11%

TABLE 30

Formulation Characterization

| Characteristics | F29-1 | F29-2 | F29-3 | F29-4 | F29-5 |
|---|---|---|---|---|---|
| Dose Strength (mg) | 1[a] | 25[a] | 5[a] | 25[a] | 20[a] |
| Drug Loading (%) | 1.8 | 23.0 | 6.9 | 13.8 | 11.0 |
| Fill Weight (mg) | 75 | 150 | 100 | 250 | 250 |
| Bulk Density (g/mL) | 0.46 | 0.28 | 0.44 | 0.34 | 0.41 |
| Tap Density (g/mL) | 0.59 | 0.55 | 0.61 | 0.58 | 0.61 |

[a]Based on free-base. 1.0 mg Compound 1 (free-base) was equivalent to 1.34 mg Compound 1 (citrate salt). Drug substance lot potency factor for these experiments was (0.725 or 1/1.38).

The CU results of F29-1, F29-3, and F29-5 are shown in Table 31. The failed CU data suggest that manual sieving used in the process may not be an effective way to deagglomerate blends, resulting in blend heterogeneity. Additional trials were conducted with an improved process (substitution of a Comil for manual sieve) and were described in the next section.

TABLE 31

Stratified CU Results F29-1, F29-3 and F29-5

| | F29-1 (1 mg), 75 mg fill, Size #4 | | | | | | F29-3 (5 mg), 100 mg fill, Size #4 | | | | | |
|---|---|---|---|---|---|---|---|---|---|---|---|---|
| | Beginning | | Middle | | End | | Beginning | | Middle | | End | |
| | Capsule Weight | % LC | Capsule Weight | % LC | Capsule Weight | % LC | Capsule Weight | % LC | Capsule Weight | % LC | Capsule Weight | % LC |
| Average | 111.3 | 90.4 | 110.8 | 95.1 | 110.3 | 93.8 | 144.4 | 106.5 | 149.9 | 110.8 | 146.9 | 108.6 |
| STD | 1.0 | 4.5 | 0.9 | 5.2 | 0.5 | 5.7 | 3.8 | 4.8 | 2.1 | 2.3 | 3.2 | 2.9 |
| AV | | 19.0 | | 15.9 | | 18.3 | | 16.4 | | 14.9 | | 14.1 |
| Pass L1 | | No | | No | | No | | No | | Yes | | Yes |

| | F29-5 (20 mg), 250 mg fill, Size #1 | | | | | |
|---|---|---|---|---|---|---|
| Average | 351.2 | 99.4 | 353.8 | 104.1 | 343.3 | 99.7 |
| STD | 7.8 | 4.1 | 14.4 | 5.6 | 24.6 | 10.4 |
| AV | | 9.8 | | 16.1 | | 25.0 |
| Pass L1 | | Yes | | No | | Mo |

TABLE 29

Formulation Composition and Characterization

| | Formulation (% w/w) | | | | |
|---|---|---|---|---|---|
| Component | F29-1 | F29-2 | F29-3 | F29-4 | F29-5 |
| Compound 1 | 1.84 | 23.02 | 6.91 | 13.81 | 11.05 |
| Avicel PH102 | 21.64 | 16.35 | 20.37 | 18.65 | 19.34 |
| Mannitol | 64.92 | 49.04 | 61.12 | 55.94 | 58.01 |
| Citric acid | | | 5 | | |
| SLS | | | 1 | | |
| Crospovidone | | | 4 | | |
| Aerosil 200 | | | 0.6 | | |
| Magnesium Stearate | | | 1 | | |

SLS = sodium lauryl sulfate.
NB Ref: 8204-015.

Figure 31:
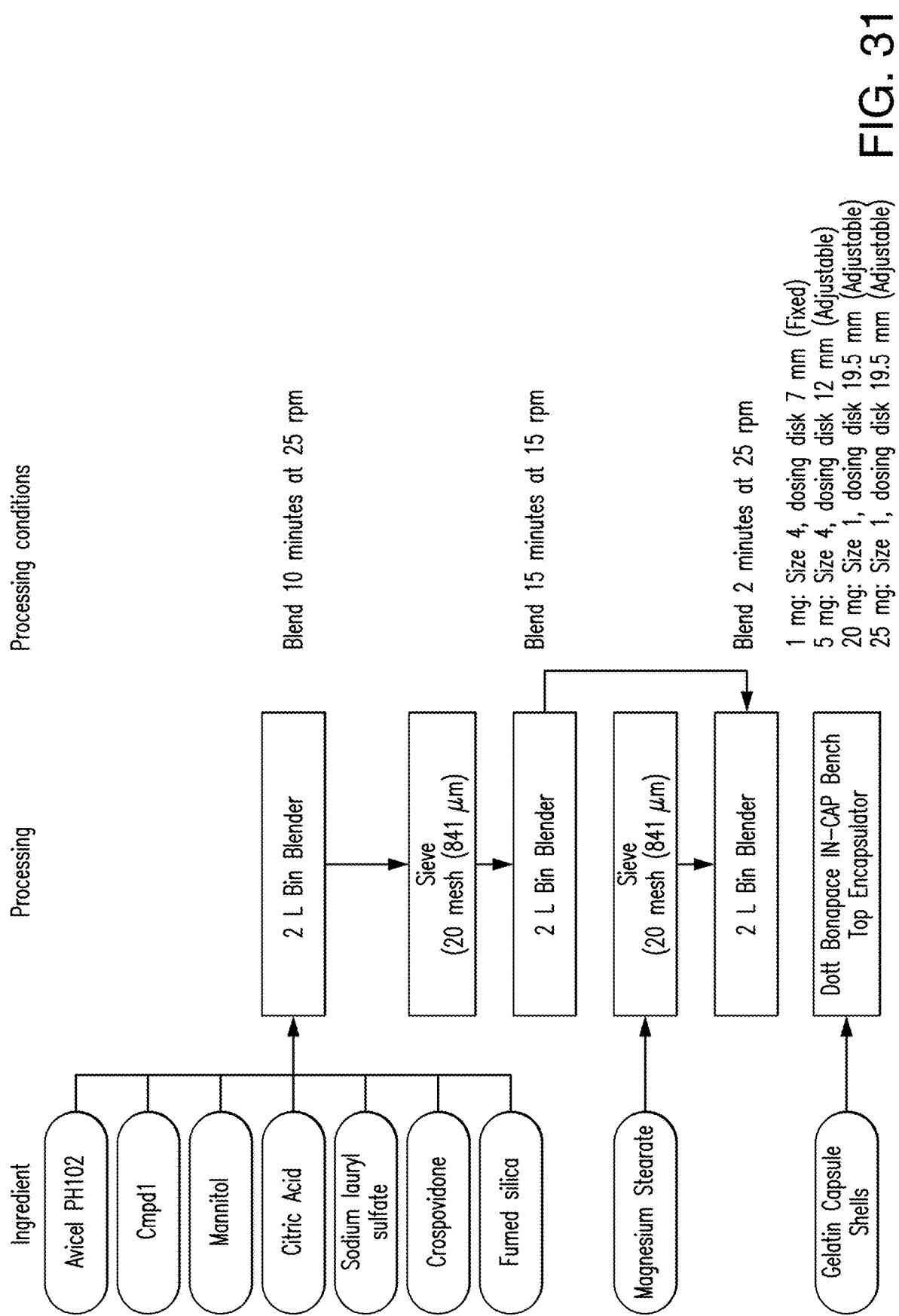
FIG. 31 shows that the 600 g trial 1 batch process flow diagram for preparation of 600 g formulations.

Five 600 g trial formulations were manufactured with the process flow shown in FIG. 31.

The 5 formulations covered drug loadings of 1.8-23.0% and 1-25 mg strengths. The bulk and tap densities for each formulation are included in Table 30.

The 25 mg formulations with drug loading of 13.8% and 23% had poor flow and the encapsulation process was paused several times. A spatula or hammer was used to facilitate powder flow in the feeding hopper. It was concluded that such high drug loading was not suitable for a dry blending process.

When the drug loading was reduced to 11%, the flow was improved. Therefore, the highest dose strength was reduced from an initial target of 25 mg to 20 mg to ensure a good processability and an appropriate capsule size.

6.26 600 g Manufacturing Trial 2

Figure 32:
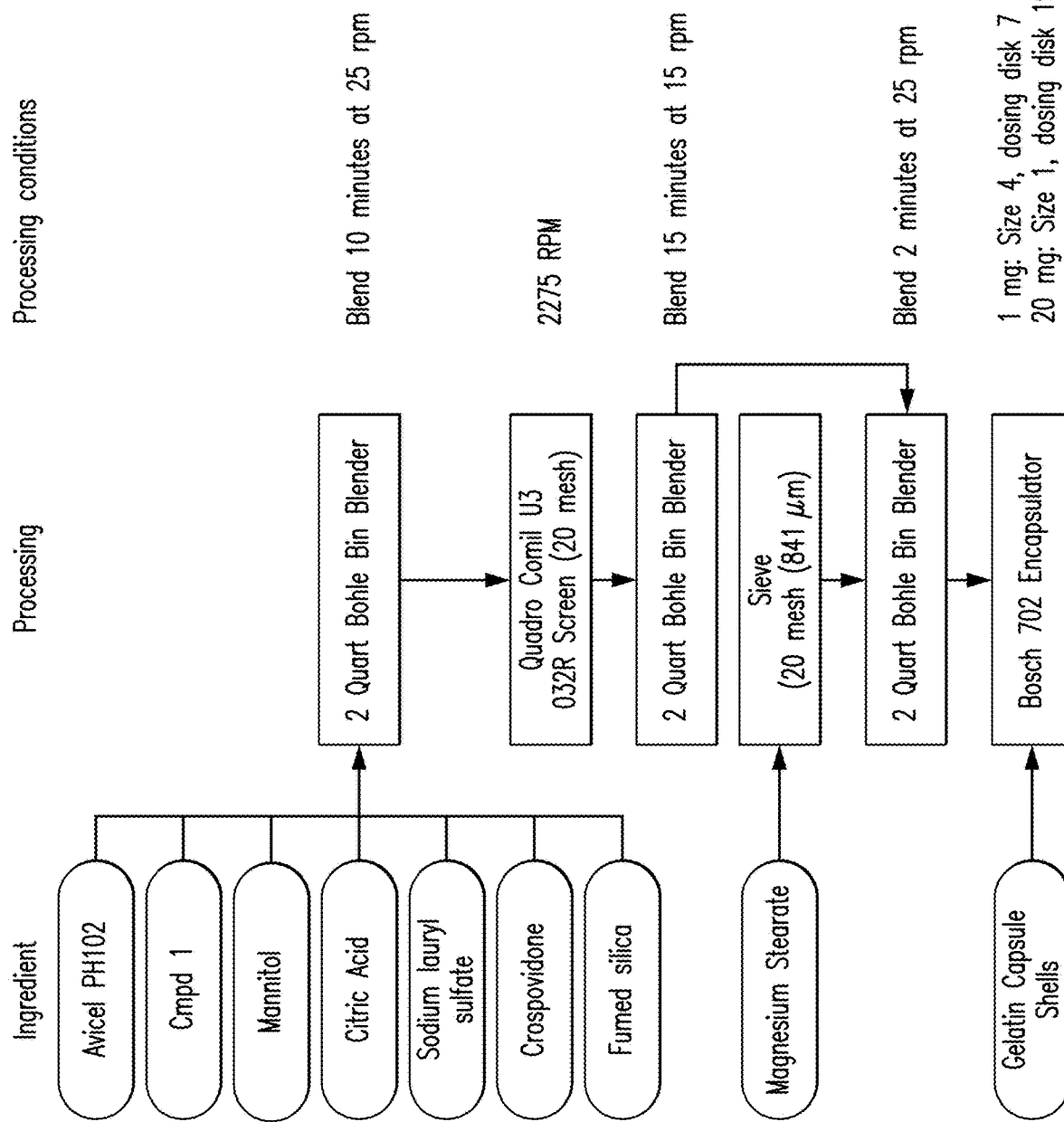
FIG. 32 shows that the 600 g trial 2 batch process flow diagram for preparation of 600 g formulations.

Based on Trial 1 results, two additional 600 g batches were manufactured, one of formulation F29-1 (low drug loading at 1.8%) and the second of formulation F29-5 (high drug loading at 11%) (Table 29). In order to improve the blend uniformity and be more representative of the scale-up process, a Quadro Comil U3 was used for deagglomeration and Bosch GKF 702 was used for encapsulation (FIG. 32). The encapsulation parameters for both batches are listed in Table 32.

TABLE 32

Encapsulation Setup Parameters

| Parameter | | F29-1 (1 mg) | F29-5 (20 mg) |
|---|---|---|---|
| Dosing Disc | | 4 | 1 |
| Dosing Disc Size (mm) | | 7 (Fixed) | 19.5 |
| Tamping Pin | 1 | 2 | 9 |
| Setting | 2 | 2 | 11 |
| | 3 | 3 | 13 |
| | 4 | 2 | 14 |
| | 5 | 2 | 16 |

For both batches, sticking to pin tips was observed. For the 1 mg lot, the sticking was correlated to the hard tamping (pins maxed, maximum tamping).

Good fill weight and content uniformity (CU) results (Table 33) were obtained except for the end samples. This poor CU was attributed to the small batch size rather than segregation, as there was insufficient powder in the feed frame towards the end of the run. Stratified CU samples was tested as the program progresses to confirm this assumption.

TABLE 33

Stratified CU Results of F29-1 and F29-5

| | F29-1 (1 mg), 75 mg fill, Size #4 | | | | | | F29-5 (20 mg), 250 mg fill, Size #1 | | | |
|---|---|---|---|---|---|---|---|---|---|---|
| | Beginning | | Middle | | End | | Beginning | | End | |
| | Capsule Weight | % LC | Capsule Weight | % LC | Capsule Weight | % LC | Capsule Weight | % LC | Capsule Weight | % LC |
| Average | 108.2 | 97.5 | 111.4 | 102.1 | 112.2 | 100.1 | 321.7 | 99.5 | 309.6 | 95.0 |
| STD | 1.5 | 1.2 | 1.2 | 1.5 | 1.4 | 7.0 | 2.3 | 2.0 | 13.4 | 5.8 |
| AV | | 3.9 | | 4.1 | | 16.9 | | 4.7 | | 17.5 |
| Pass L1 | | Yes | | Yes | | No | | Yes | | No |

USP <905> Uniformity of Dosage Units Acceptance Value (AV) ≤15.0 to pass requirements.
STD = standard deviation Based on the good potency and acceptance value results, the process was scaled to 2 kg technical batches.

6.27 2 kg Technical Batch Manufacturing Trials

One batch each of 1, 5, and 20 mg capsule strengths (F29-1, F29-3 and F29-5) were manufactured at the 2 kg scale. The formulation composition for these batches are shown in Table 34.

The final formulation compositions for FIH are shown in Section 6.28.

TABLE 34

2-kg technical batches of 1 mg, 5 mg, and 20 mg

| | (% w/w) | | |
|---|---|---|---|
| Component | F29-1 | F29-3 | F29-5 |
| Compound 1 | 1.80 | 6.73 | 11.05 |
| MCC (Avicel PH102) | 21.65 | 20.42 | 19.34 |
| Mannitol (Parteck M200) | 64.95 | 61.25 | 58.01 |
| Fumaric acid | | 5 | |
| SLS | | 1 | |
| Crospovidone (Kollidon CL) | | 4 | |
| Fumed silica (Aerosil 200) | | 0.6 | |
| Magnesium Stearate (HyQual VG 2257) | | 1 | |
| Fill weight | 75 mg | 100 mg | 250 mg |
| Capsule[a] | Size #4 | Size #4 | Size #1 |

[a]Capsule = Hard gelatin, white opaque
[a]Based on free-base. 1.0 mg Compound 1 (free-base) was equivalent to 1.34 mg Compound 1 (citrate salt). Drug substance lot potency factor for these experiments was (0.725 or 1/1.38).

Figure 33:
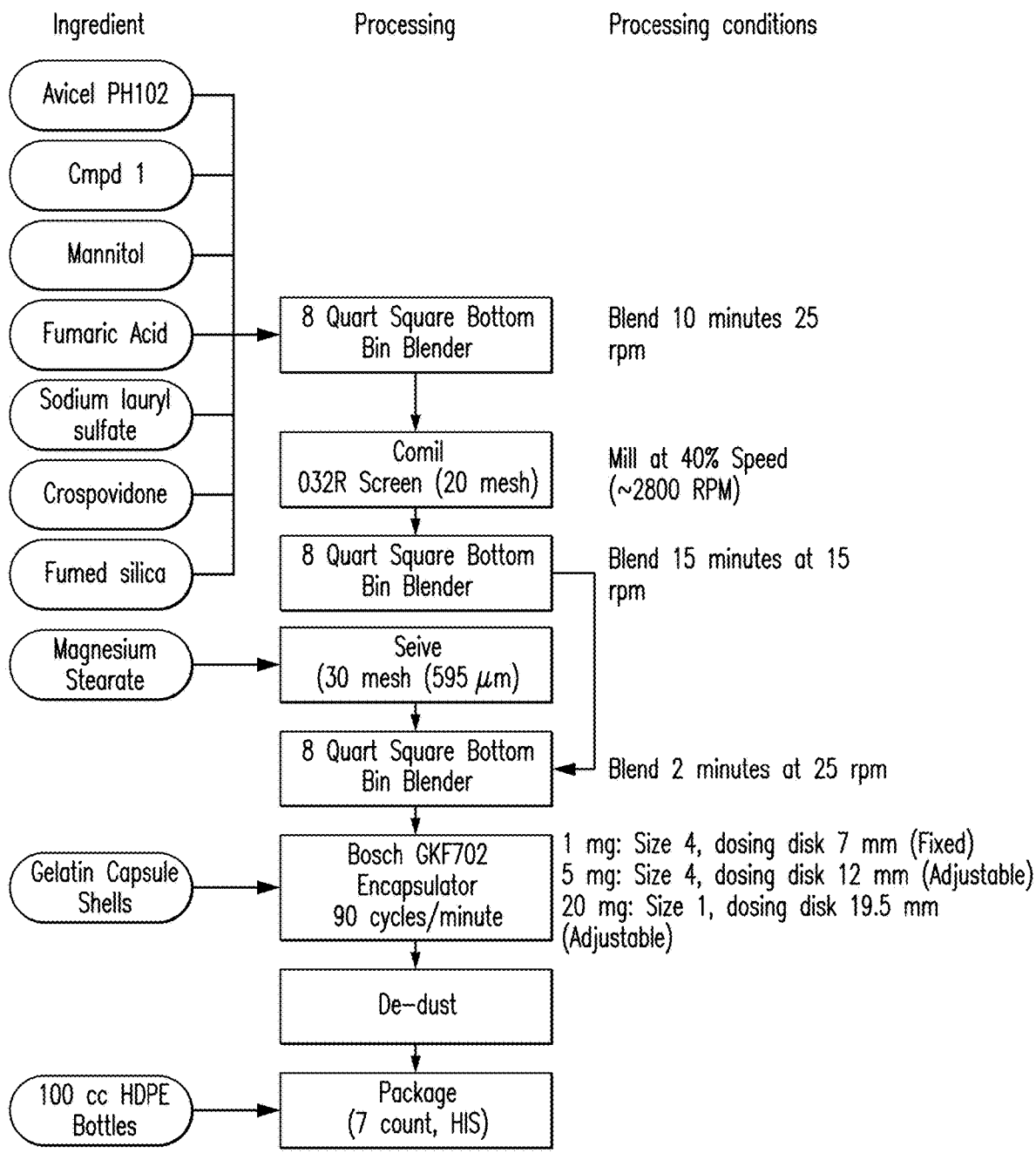
FIG. 33 shows the batch process flow diagram for the manufacture of the 2 kg technical batches.

The process flow diagram for the manufacture of the 2 kg technical batches is shown in FIG. 33. The encapsulation parameters for the batches are listed in Table 35.

A narrative of the process is listed below.

Weigh out each raw material in individual plastic bags.

Load the dispensed API and excipients except for magnesium stearate into the 8-QT square Bin.

Blend the material for 10 min at 25 rpm.

Charge the Comil with the blended material. Using a 20 mesh Comil screen, pass the blend through Comil at approximately 2800 rpm (40% speed).

Transfer the material into the blender bin. Blend the material for 15 min at 15 rpm.

Pass the dispensed magnesium stearate through a 30 mesh (595 micron) screen directly into screen pan and add to the blender.

Blend the material for 2 minutes at 25 rpm.

Discharge the blend into feeding bowl of Bosch GKF702 Encapsulator.

Set up the Bosch GKF702 Encapsulator with the following Change parts:

a. 75 mg fill, size #4 capsules: 7 mm fixed dosing disk b. 100 mg fill, size #4 capsules: 12 mm adjustable dosing disk c. 250 mg fill, size #1 capsules: 19.5 mm adjustable dosing disk Set encapsulation speed at 90 cycles per minute. Start encapsulation and adjust the machine to provide target weight.

Collect capsules as they are discharged from the Encapsulator on a suitable sieve. As the capsules fill the sieve, use the vacuum to de-dust the capsules. Place the capsules into the tared double polyethylene bag lined container.

Package the bulk capsules in the bag container into 100 cc HDPE bottles (7 count per bottle, heat induction sealed).

TABLE 35

Encapsulation Setup Parameters

| Parameter | | F29-1 (1 mg) | F29-3 (5 mg) | F29-5 (20 mg) |
|---|---|---|---|---|
| Dosing Disc | | 4 | 4 | 1 |
| Dosing Disc Size (mm) | | 7 | 12 | 19.5 |
| Machine Speed (cycles/min) | | 90 | 90 | 90 |
| Tamping Pin Setting | 1 | 2 | 4 | 9 |
| | 2 | 2 | 5 | 10 |
| | 3 | 2 | 4 | 11 |
| | 4 | 2 | 5 | 14 |
| | 5 | 2 | 9 | 17 |

For all batches, drug substance sticking to pin tips was observed. For the 1 mg lot, the tamping pins were set at maximum.

Bulk and tap densities and flow properties for the 2 kg technical batches are listed in Table 36. Flow property scales for Carr's (Compressibility) Index and Hausner's Ratio are described in Table 37. The flow of the blends was assessed as very poor to passible.

TABLE 36

Bulk and Tap Density and Flow Properties for the Technical Batches

| Property | F29-1 (1 mg) | F29-3 (5 mg) | F29-5 (20 mg) |
|---|---|---|---|
| Bulk Density (g/mL) | 0.4672 | 0.4363 | 0.4229 |
| Tapped Density (g/mL) | 0.6088 | 0.6371 | 0.6278 |
| Hausner's Ratio | 1.30 | 1.46 | 1.48 |
| Carr's Index | 23.3 | 31.5 | 32.6 |

Carr's (Compressibility) Index = (tapped density − bulk density)*100/tapped density
Hausner's Ratio = tapped density/bulk density

TABLE 37

Generally Accepted Scales of Flow Properties

| Flow Character | Carr's (Compressibility) Index (%) | Hausner's Ratio |
|---|---|---|
| Excellent | ≤10 | 1.00-1.11 |
| Good | 11-15 | 1.12-1.18 |
| Fair | 16-20 | 1.19-1.25 |
| Passible | 21-25 | 1.26-1.34 |
| Poor | 26-31 | 1.35-1.45 |
| Very Poor | 32-37 | 1.46-1.59 |
| Very, Very Poor | ≥38 | ≥1.60 |

Carr's (Compressibility) Index = (tapped density − bulk density)*100/tapped density
Hausner's Ratio = tapped density/bulk density FFC was assessed by ring shear, and the blends were assessed as having good flow properties (Table 38).

TABLE 38

Flowability Measurement by Ring Shear

| FFC | F29-1 | F29-3 | F29-5 |
|---|---|---|---|
| Test 1 | 15.48 | 10.2 | 6.17 |
| Test 2 | 20.78 | 11.02 | 6.22 |
| Test 3 | 20.56 | | |
| Average | 18.94 | 10.61 | 6.19 |

FFC = Flow function coefficients

FFC values greater than 5 had good flow properties, and all three batches had FFC>5.

The particle size distribution of the formulations was assessed using screens, and the results are listed in Table 39.

TABLE 39

Particle size distribution by sieve analysis

| | Parameter | PD01-282 | PD01-283 | PD01-284 |
|---|---|---|---|---|
| | Sample weight (g) | 5.042 | 5.025 | 5.0042 |
| | Shake Time (min) | 5 | 5 | 5 |
| Screen | Amplitude | 3 | 5 | 3 |
| 420 µm | Mesh #40 | 1.4 | 2.1 | 2.4 |
| 250 µm | Mesh #60 | 12.7 | 13.0 | 12.5 |
| 177 µm | Mesh #80 | 16.6 | 17.1 | 17.4 |
| 149 µm | Mesh #100 | 11.9 | 11.7 | 12.8 |
| 125 µm | Mesh #120 | 13.3 | 13.2 | 13.0 |
| 74 µm | Mesh #200 | 29.2 | 25.4 | 26.6 |
| 0 | pan | 14.9 | 17.6 | 15.3 |
| | Average particle size (µm) | 122.6 | 123.8 | 126.8 |

Stratified CU was tested, and acceptable results were obtained for beg, mid, and end samples as listed in Table 40, Table 41, and Table 42.

TABLE 40

Content Uniformity and Weight Variability PD01-282 (1 mg)

| Beginning | | | Middle | | | End | | |
|---|---|---|---|---|---|---|---|---|
| Sample | % LC | Weight | Sample | % LC | Weight | Sample | % LC | Weight |
| 1 | 93.7 | 108.3 | 1 | 91.1 | 107.8 | 1 | 95.4 | 110.4 |
| 2 | 92.7 | 109.8 | 2 | 94.3 | 111.0 | 2 | 99.7 | 112.3 |
| 3 | 93.9 | 110.3 | 3 | 91.6 | 108.4 | 3 | 93.9 | 110.5 |
| 4 | 90.7 | 109.6 | 4 | 93.6 | 111.4 | 4 | 98.2 | 112.6 |
| 5 | 92.2 | 110.0 | 5 | 95.5 | 110.8 | 5 | 98.4 | 112.9 |
| 6 | 93.7 | 109.0 | 6 | 92.6 | 108.3 | 6 | 96.4 | 111.7 |
| 7 | 93.1 | 108.7 | 7 | 93.7 | 110.9 | 7 | 96.3 | 112.1 |
| 8 | 91.7 | 107.2 | 8 | 94.5 | 110.7 | 8 | 95.3 | 111.8 |
| 9 | 90.8 | 109.2 | 9 | 90.5 | 107.2 | 9 | 98.8 | 113.0 |
| 10 | 90.0 | 108.9 | 10 | 94.0 | 109.2 | 10 | 97.4 | 111.9 |
| Average | 92.2 | 109.1 | Average | 93.1 | 109.6 | Average | 97.0 | 111.9 |

TABLE 40-continued

Content Uniformity and Weight Variability PD01-282 (1 mg)

| Beginning | | | Middle | | | End | | |
|---|---|---|---|---|---|---|---|---|
| Sample | % LC | Weight | Sample | % LC | Weight | Sample | % LC | Weight |
| SD | 1.4 | 0.9 | SD | 1.6 | 1.6 | SD | 1.8 | 0.9 |
| % RSD | 1.5 | 0.8 | % RSD | 1.7 | 1.4 | % RSD | 1.9 | 0.8 |
| AV | 9.6 | | AV | 9.2 | | AV | 5.9 | |

AV = acceptance value;
LC = label claim;
SD = standard deviation.
RSD = relative standard deviation

TABLE 41

Content Uniformity and Weight Variability F3 (5 mg)

| Beginning | | | Middle | | | End | | |
|---|---|---|---|---|---|---|---|---|
| Sample | % LC | Weight | Sample | % LC | Weight | Sample | % LC | Weight |
| 1 | 94.4 | 136.4 | 1 | 95.4 | 134.98 | 1 | 97.2 | 136.3 |
| 2 | 95.3 | 135.8 | 2 | 97.7 | 137.64 | 2 | 99.5 | 140.8 |
| 3 | 97.3 | 138.1 | 3 | 95.3 | 134.45 | 3 | 99.1 | 139.8 |
| 4 | 101.3 | 142.2 | 4 | 97.2 | 137.47 | 4 | 99.4 | 139.2 |
| 5 | 97.6 | 138.9 | 5 | 95.4 | 134.64 | 5 | 98.1 | 138.3 |
| 6 | 94.3 | 134.1 | 6 | 102.0 | 142.2 | 6 | 104.5 | 141.7 |
| 7 | 97.5 | 136.5 | 7 | 96.4 | 136.81 | 7 | 98.3 | 138.1 |
| 8 | 97.1 | 138.6 | 8 | 95.9 | 134.53 | 8 | 98.9 | 137.9 |
| 9 | 97.4 | 138.1 | 9 | 97.8 | 136.71 | 9 | 100.0 | 138.0 |
| 10 | 97.6 | 138.2 | 10 | 98.5 | 138.15 | 10 | 99.5 | 139.1 |
| Average | 97.0 | 137.7 | Average | 97.2 | 136.8 | Average | 99.5 | 138.9 |
| SD | 2.0 | 2.2 | SD | 2.0 | 2.4 | SD | 1.9 | 1.6 |
| % RSD | 2.1 | 1.6 | % RSD | 2.1 | 1.7 | % RSD | 1.9 | 1.1 |
| AV | 6.4 | | AV | 6.2 | | AV | 4.7 | |

AV = acceptance value;
LC = label claim;
SD = standard deviation;
RSD = relative standard deviation

TABLE 42

Content Uniformity and Weight Variability F5 (20 mg)

| Beginning | | | Middle | | | End | | |
|---|---|---|---|---|---|---|---|---|
| Sample | % LC | Weight | Sample | % LC | Weight | Sample | % LC | Weight |
| 1 | 98.7 | 327.5 | 1 | 94.0 | 319.63 | 1 | 97.0 | 317.4 |
| 2 | 98.5 | 328.4 | 2 | 95.4 | 325.48 | 2 | 99.1 | 321.8 |
| 3 | 96.3 | 322.2 | 3 | 98.9 | 331.33 | 3 | 99.3 | 321.6 |
| 4 | 96.9 | 326.3 | 4 | 99.2 | 330.39 | 4 | 98.1 | 318.0 |
| 5 | 93.9 | 317.8 | 5 | 97.9 | 328.89 | 5 | 101.5 | 327.2 |
| 6 | 98.2 | 330.0 | 6 | 94.3 | 318.8 | 6 | 93.0 | 307.0 |
| 7 | 96.8 | 326.0 | 7 | 94.3 | 317.63 | 7 | 97.9 | 320.3 |
| 8 | 96.8 | 321.6 | 8 | 96.0 | 321.43 | 8 | 97.8 | 317.9 |
| 9 | 91.8 | 310.8 | 9 | 97.2 | 327.27 | 9 | 98.3 | 319.5 |
| 10 | 94.9 | 320.8 | 10 | 94.2 | 327.76 | 10 | 96.8 | 316.5 |
| Average | 96.3 | 323.1 | Average | 96.1 | 324.9 | Average | 97.9 | 318.7 |
| SD | 2.2 | 5.8 | SD | 2.0 | 5.1 | SD | 2.2 | 5.1 |
| % RSD | 2.3 | 1.8 | % RSD | 2.1 | 1.6 | % RSD | 2.2 | 1.6 |
| AV | 7.5 | | AV | 7.2 | | AV | 5.8 | |

AV = acceptance value;
LC = label claim;
SD = standard deviation;
RSD = relative standard deviation The 3 technical batches have been set up on a formal (ICH) stability program to support the clinical program.

6.28 FIH Formulation Composition

In review of the data, and taking into consideration stability, dissolution performance, and manufacturability, the enhanced formulation (contain fumaric acid and sodium lauryl sulfate) in gelatin capsule shells was selected for the FIH study. Formulation compositions of the three strengths are listed in Table 43.

TABLE 43

FIH Formulation Composition

| Component | 1 mg[a] mg/cap | 1 mg[a] w/w % | 5 mg[a] mg/cap | 5 mg[a] w/w % | 20 mg[a] mg/cap | 20 mg[a] w/w % |
|---|---|---|---|---|---|---|
| Compound 1 | 1.34 | 1.79 | 6.70 | 6.70 | 26.80 | 10.72 |
| Avicel PH102 | 16.24 | 21.65 | 20.42 | 20.42 | 48.53 | 19.41 |
| Mannitol (Parteck M200) | 48.72 | 64.96 | 61.28 | 61.28 | 145.68 | 58.27 |
| Sodium lauryl sulfate | 0.75 | 1.0 | 1.00 | 1.0 | 2.50 | 1.0 |
| Fumaric acid | 3.75 | 5.0 | 5.00 | 5.0 | 12.50 | 5.0 |
| Crospovidone | 3.00 | 4.0 | 4.00 | 4.0 | 10.00 | 4.0 |
| Aerosil 200 | 0.45 | 0.6 | 0.60 | 0.6 | 1.50 | 0.6 |
| Magnesium Stearate | 0.75 | 1.0 | 1.00 | 1.0 | 2.50 | 1.0 |
| Fill weight | 75.00 | 100.0 | 100.00 | 100.0 | 250.00 | 100.0 |
| Capsule Shell[b] | Size #4 | | Size #4 | | Size #1 | |

[a]Based on free-base. 1.0 mg Compound 1 (free-base) is equivalent to 1.34 mg Compound 1 (citrate salt). Actual drug substance weight was based upon the drug substance lot potency factor, with adjustments in weight made to mannitol to obtain the target blend weight.
[b]Capsule = Hard gelatin, white opaque.

6.29 Conclusions

Blend in capsule formulation development was undertaken to minimize the pH dependence on the in vitro dissolution drug release. 1, 5, and 20 mg formulations were developed for FIH clinical trials based on dog PK, in vitro dissolution, and stability studies. The enhanced formulations contained an acidifier (fumaric acid) and surfactant (sodium lauryl sulfate) for control of local pH and enhancing drug solubility. This combination of excipients, leading to the enhanced formulation, reduced the variability in dissolution release profile observed with the conventional formulation in various pH media.

A dry blending process was developed for all strengths. The formulations have been successfully scaled to 2 kg. Acceptable CU was demonstrated for 2-kg batch size. The same process was expected to be tech transferred to a contract manufacturing organization for the manufacturing of 3-kg engineering and clinical trial material (CTM) batches.

6.30 Capsules A-J

Capsules A-H were produced and examined in the below studies. The composition of each capsule is provided in Table 44.

TABLE 44

Composition of Capsules

| Capsule Component | A | B | C | D | E | F | G | H |
|---|---|---|---|---|---|---|---|---|
| | Percent by weight | | | | | | | |
| Compound 1 | 37% | 25% | 25% | 50% | 50% | 50% | 50% | 50% |
| HPMC | 53% | — | — | 40% | — | — | 50% | — |
| PVA-P | — | 65% | — | — | 40% | — | — | 50% |
| PVP VA 64 | — | — | 65% | — | — | 40% | — | — |
| TPGS | 10% | 10% | 10% | 10% | 10% | 10% | — | — |
| Total | 100% | 100% | 100% | 100% | 100% | 100% | 100% | 100% |

Figure 34:
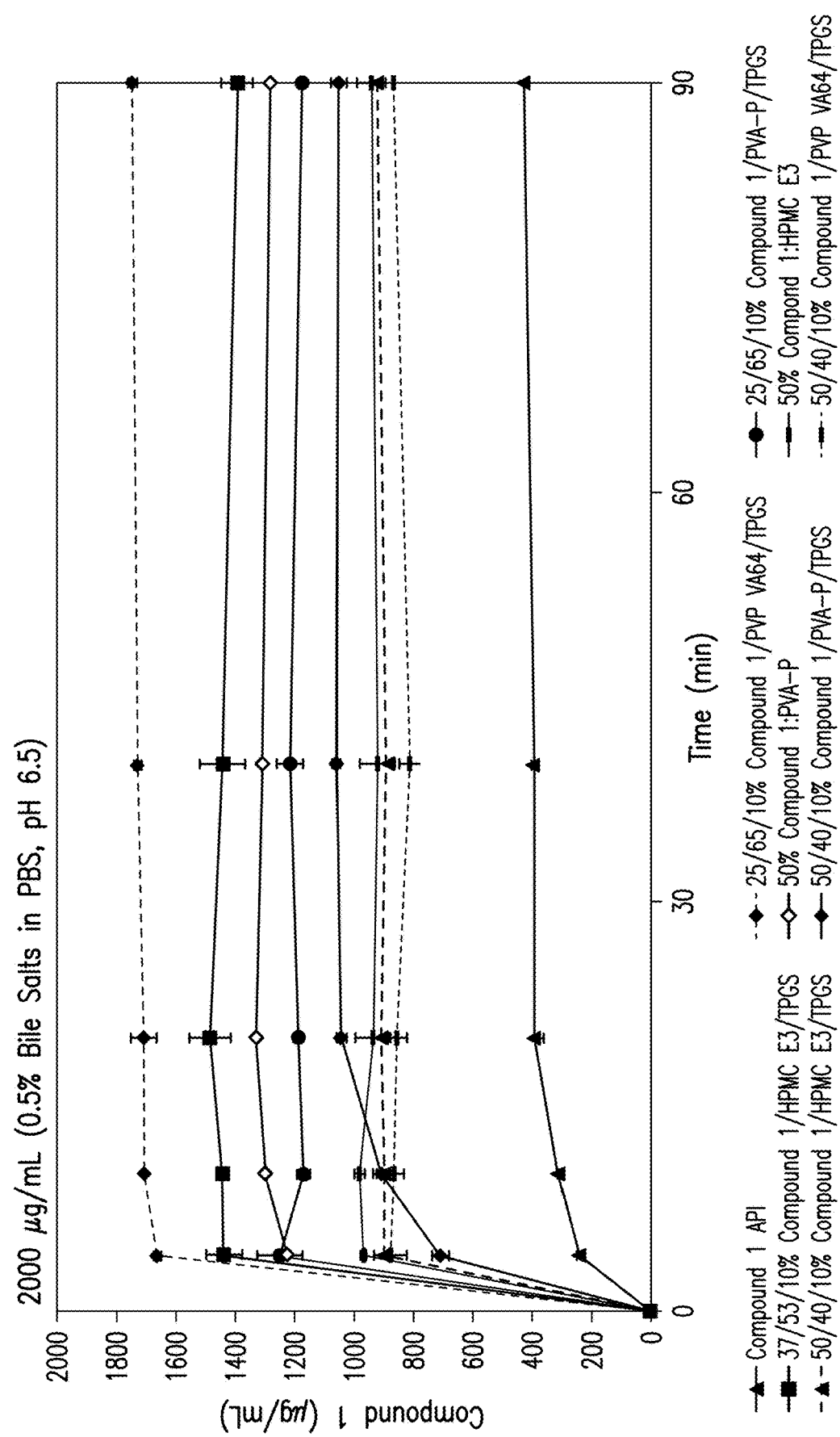
FIG. 34 shows dissolution profiles of Compound 1 formulations in intestinal buffer dissolution over 90 minutes.

FIG. 34 shows dissolution profiles of Compound 1 formulations in intestinal buffer dissolution over 90 minutes.

Figure 35:
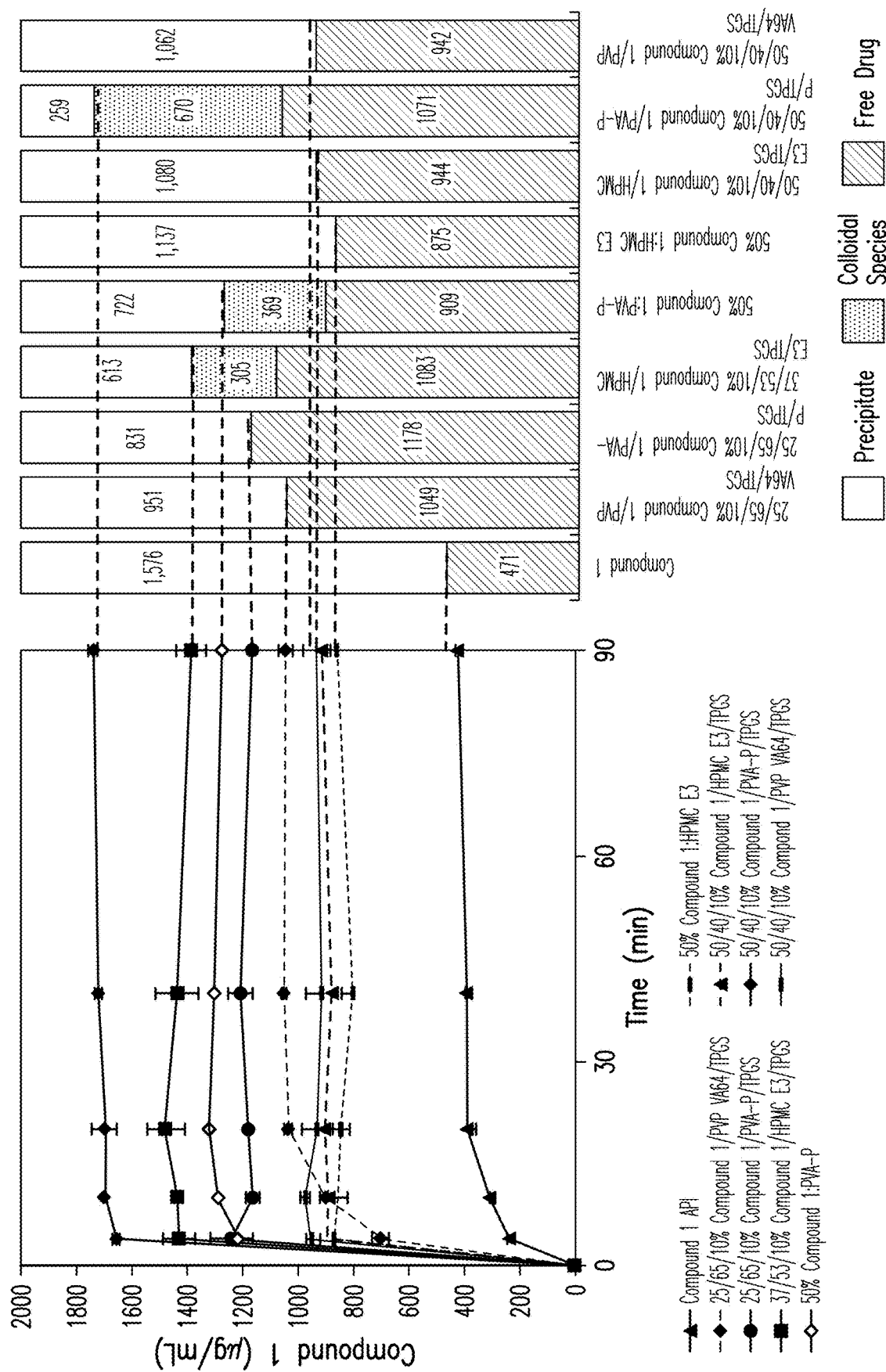
FIG. 35 shows dissolution profiles of Compound 1 formulations in intestinal buffer dissolution and speciation.

FIG. 35 shows dissolution profiles of Compound 1 formulations in intestinal buffer dissolution and speciation. Capsule E shows the best performance with regards to total solubilized drug. The higher loading PVA-P formulations showed better performance compared to their lower loading counterparts. The addition of TPGS to the formulation showed a positive impact on the solubility of Compound 1.

Figure 36:
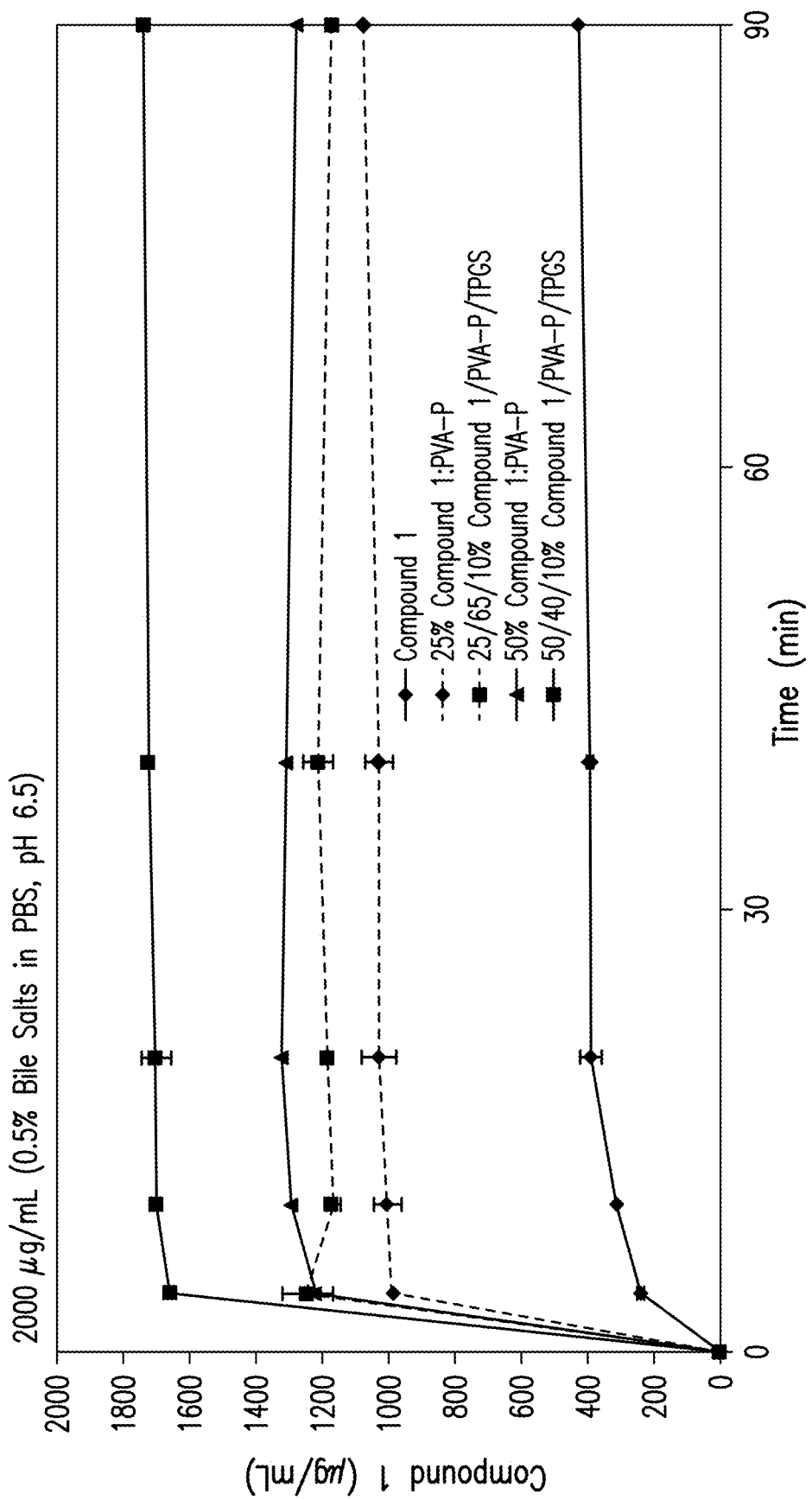
FIG. 36 shows a dissolution comparison across the PVA-P formulations (Capsule B, Capsule E, and Capsule H).

FIG. 36 shows a dissolution comparison across the PVA-P formulations (Capsule B, Capsule E, and Capsule H). The PVA-P formulations performed better at higher loading, as well as with the addition of TPGS.

Figure 37:
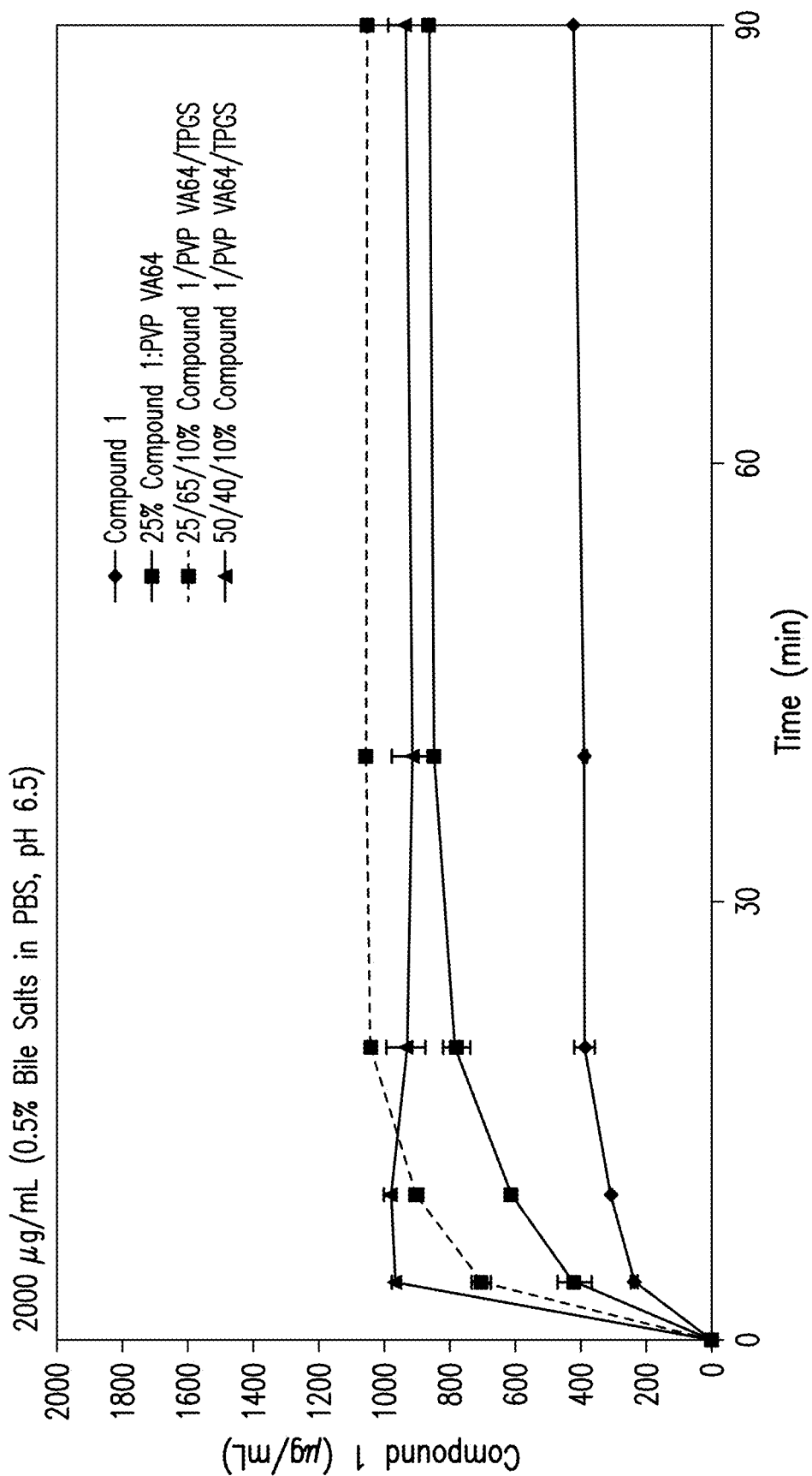
FIG. 37 shows a dissolution comparison across the PVP VA64 formulations (Capsule C and Capsule F).

FIG. 37 showed a dissolution comparison across the PVP VA64 formulations (Capsule C and Capsule F). Increased loading and the addition of TPGS showed only a modest improvement on formulations with PVP VA64 compared to other polymers.

Figure 38:
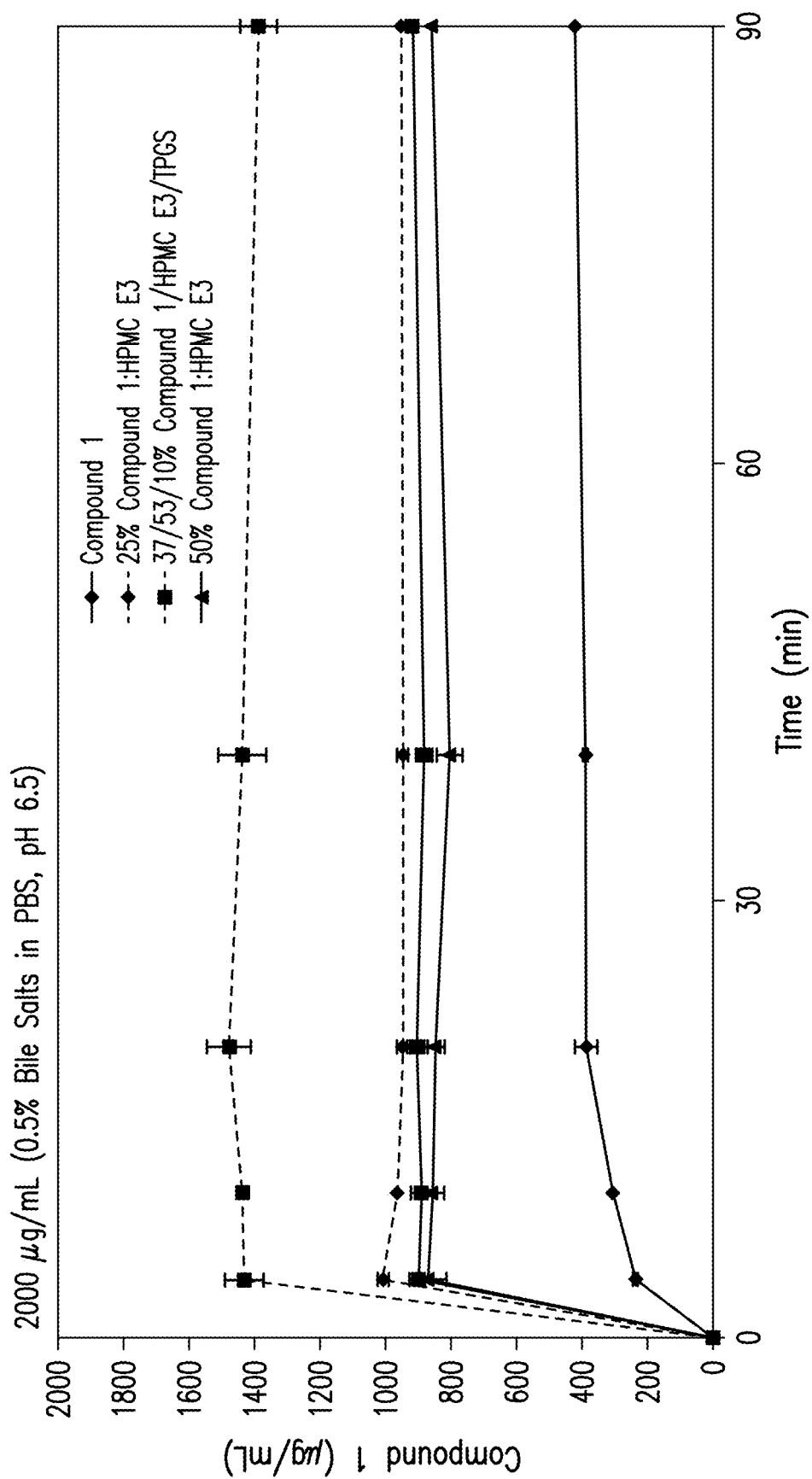
FIG. 38 shows a dissolution comparison across the HPMC formulations (Capsule A, Capsule D, and Capsule G).

FIG. 38 shows a dissolution comparison across the HPMC formulations (Capsule A, Capsule D, and Capsule G). Increasing the drug loading with HPMC had little impact on dissolution performance. TPGS showed a significant improvement in the solubility of Compound 1 in Capsule A.

Figure 39:
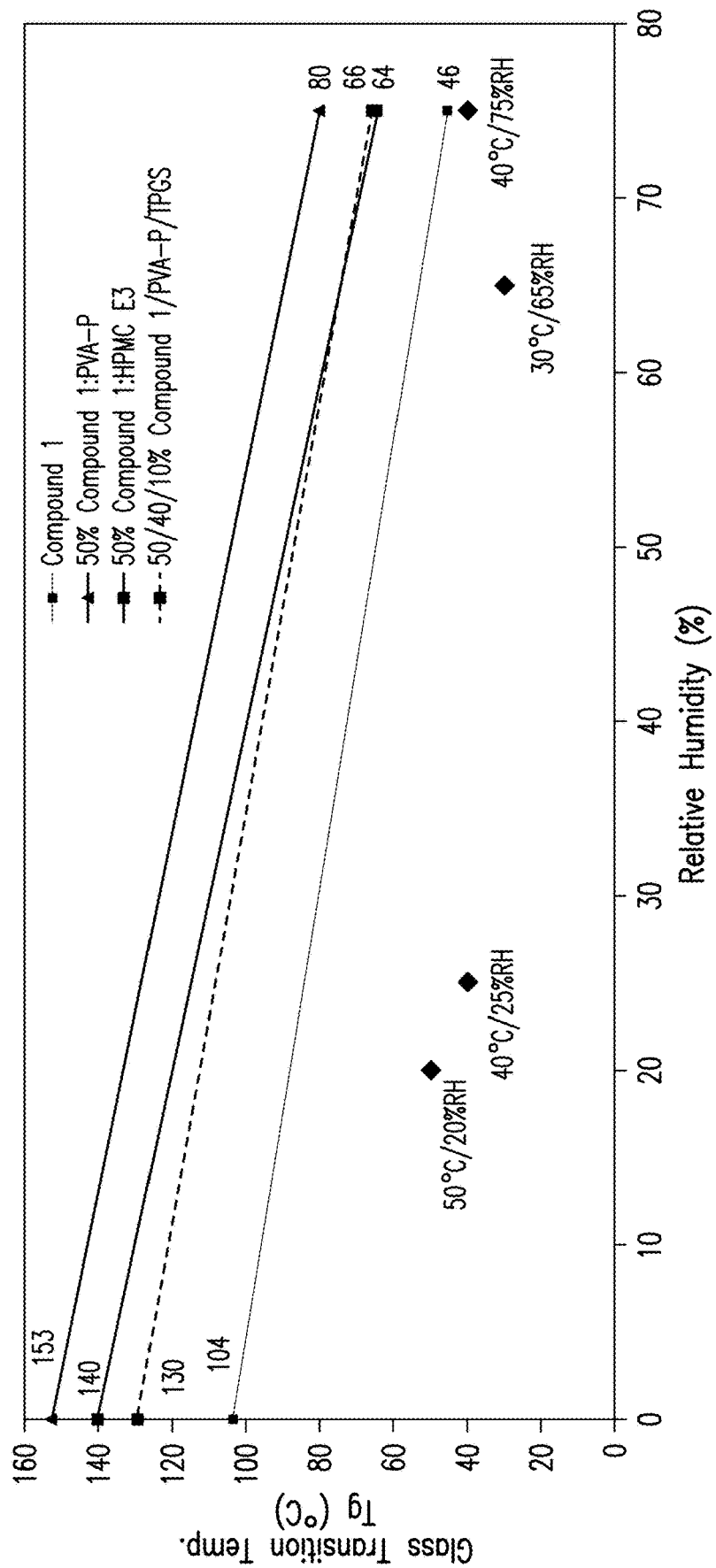
FIG. 39 shows the glass transition temperature versus relative humidity.

FIG. 39 shows the glass transition temperature versus relative humidity.

Figure 40:
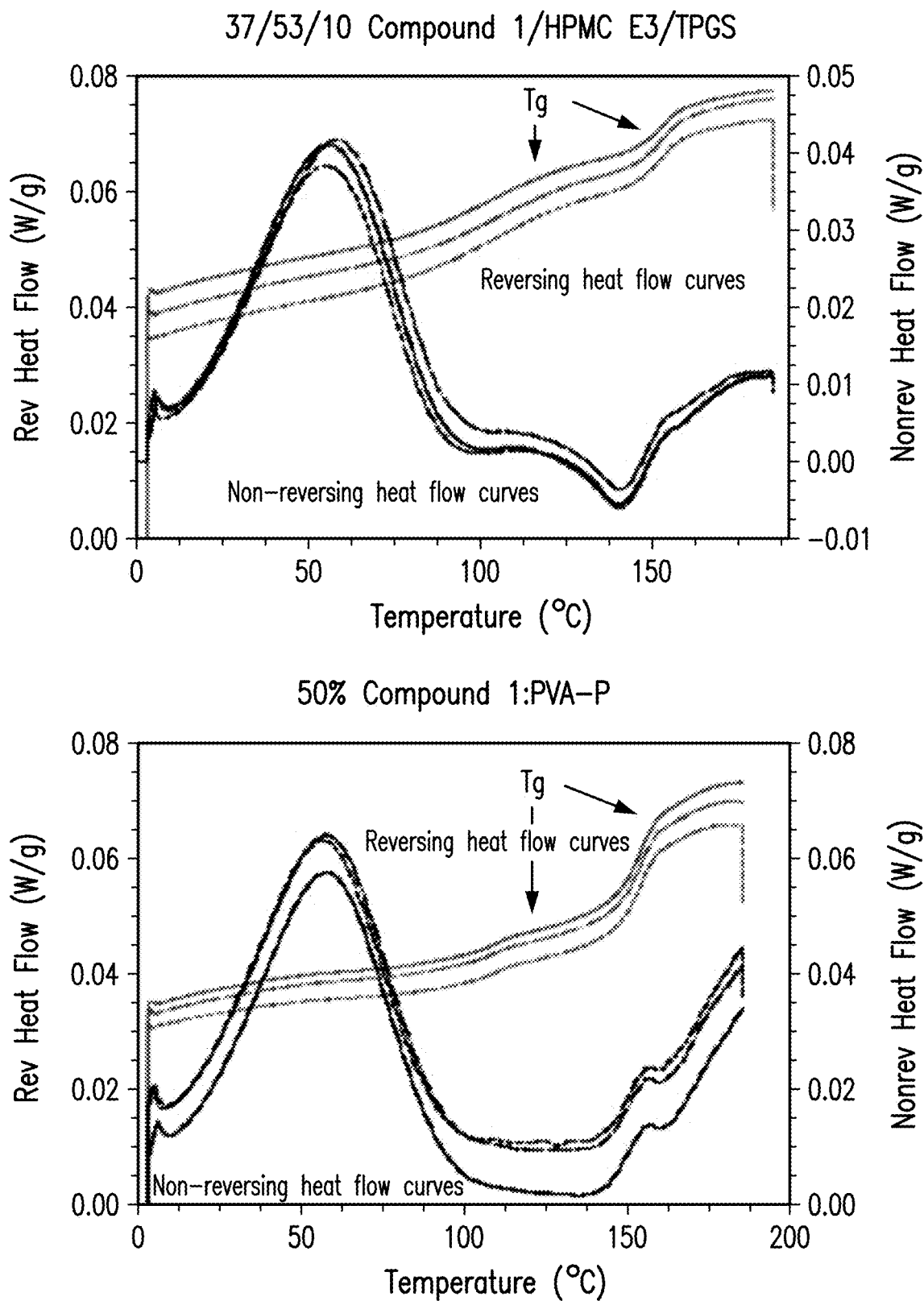
FIG. 40 shows the reversible and nonversible heat flow of Capsule A and Capsule H at less then 5% relative humidity.

FIG. 40 shows the reversible and nonversible heat flow of Capsule A and Capsule H at less then 5% relative humidity.

FIG. 41 shows the reversible and nonversible heat flow of Capsule A and Capsule H at 75% relative humidity.

Figure 42:
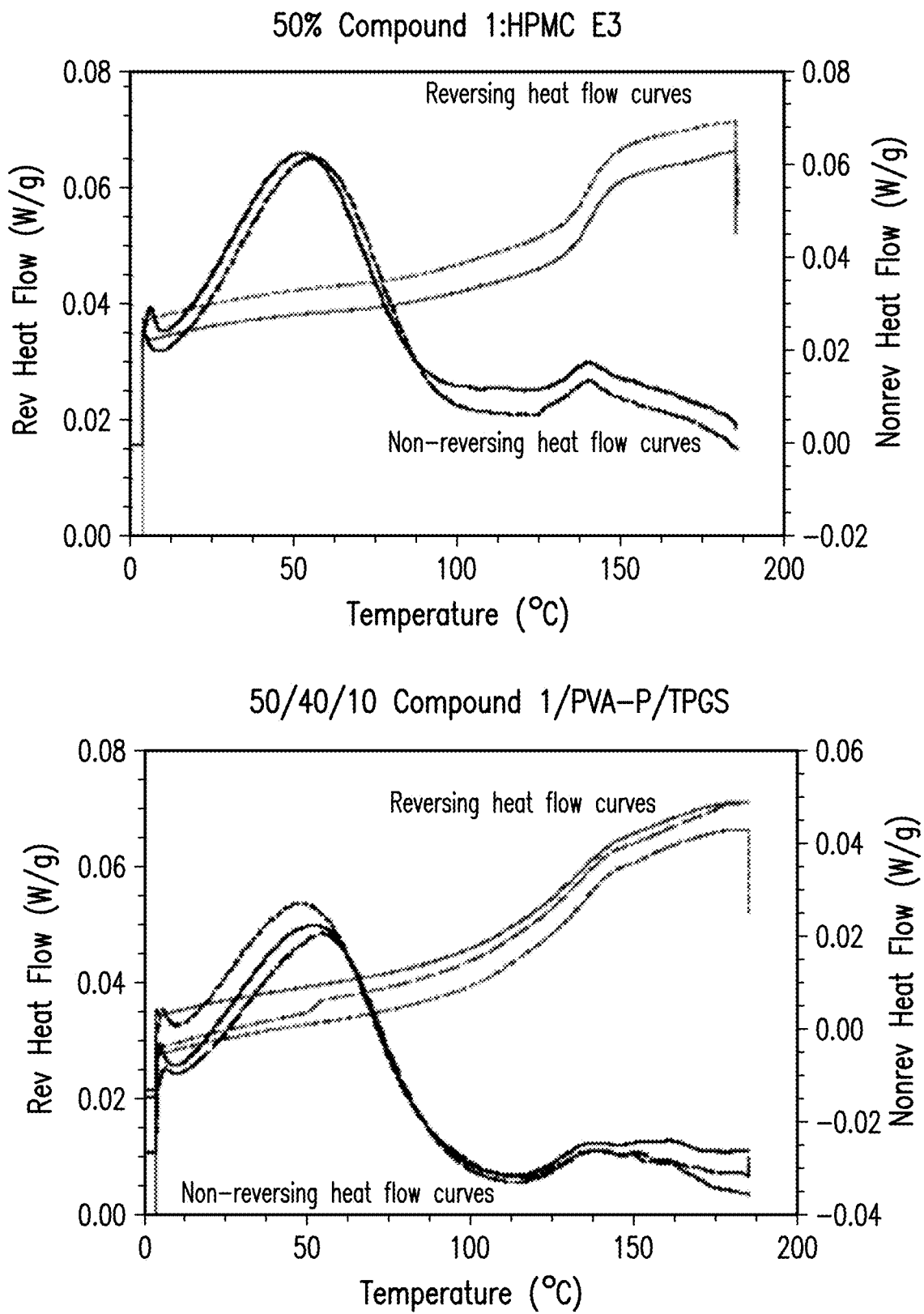
FIG. 42 shows the reversible and nonversible heat flow of Capsule G and Capsule E at less than 5% relative humidity.

FIG. 42 shows the reversible and nonversible heat flow of Capsule G and Capsule E at less than 5% relative humidity.

Figure 43:
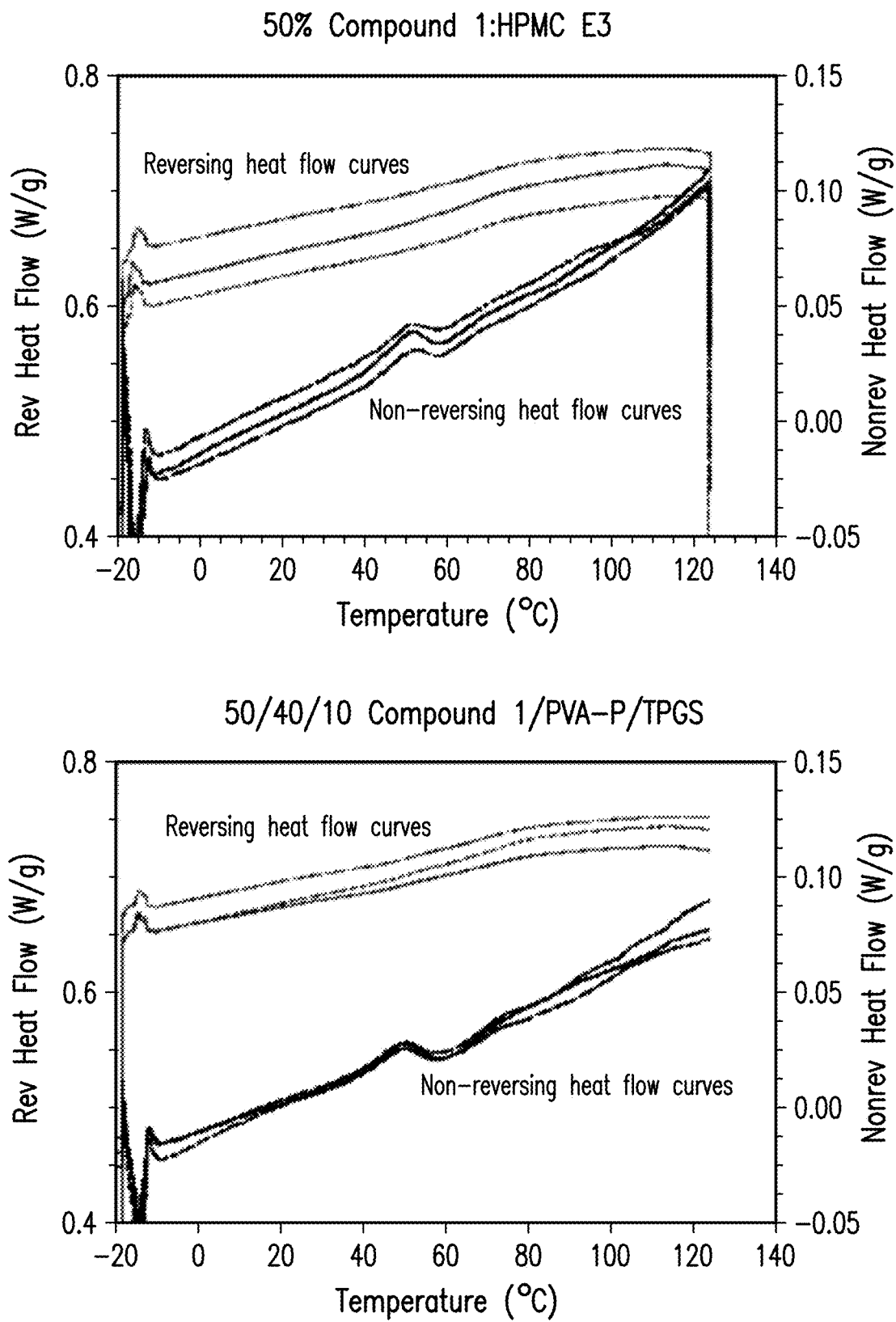
FIG. 43 shows the reversible and nonversible heat flow of Capsule G and Capsule E at 75% relative humidity.

FIG. 43 shows the reversible and nonversible heat flow of Capsule G and Capsule E at 75% relative humidity.

Figure 44:
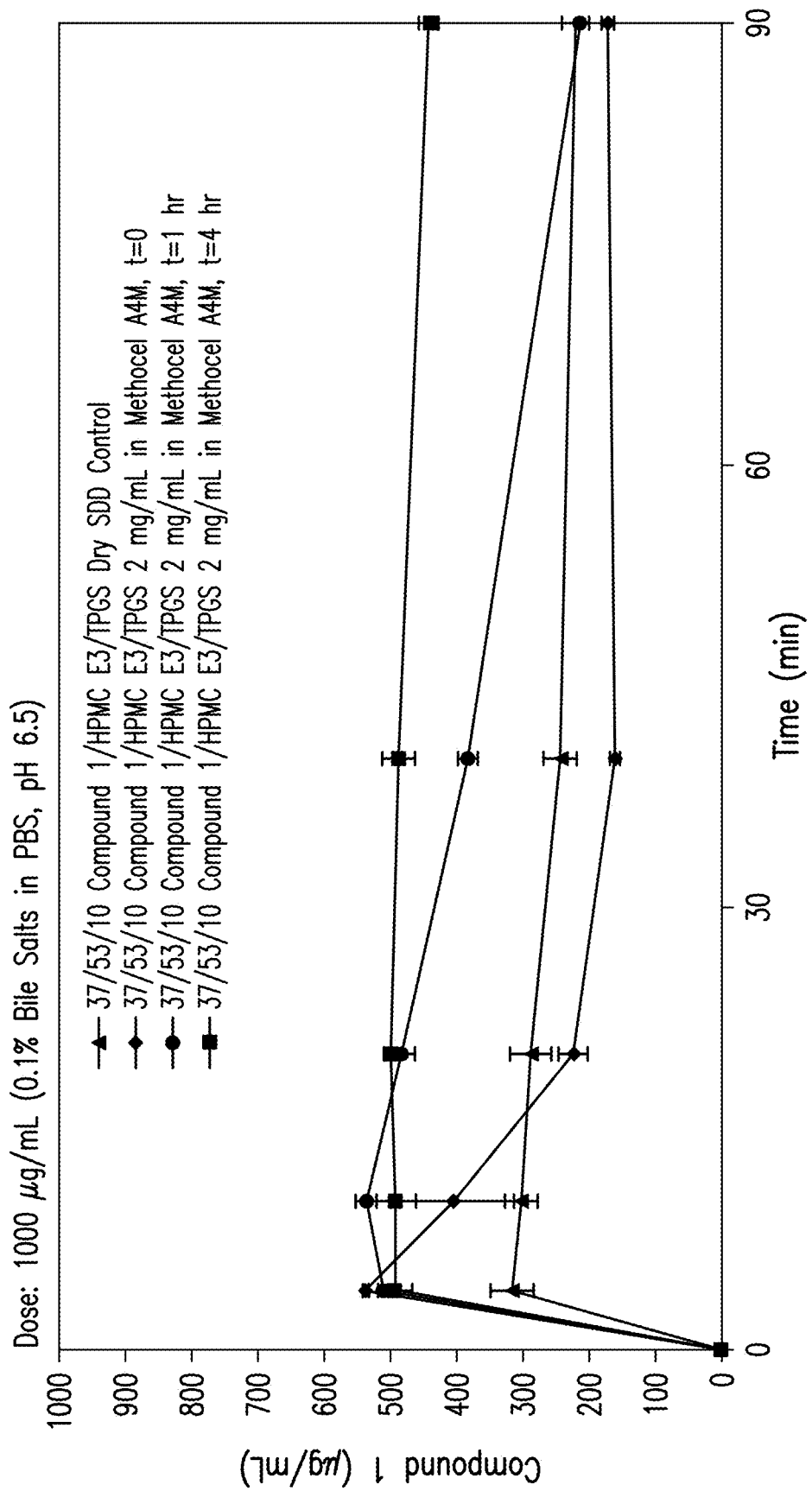
FIG. 44 shows the suspension stability of Capsule A in Methocel.

FIG. 44 shows the suspension stability of Capsule A in Methocel.

Figure 45:
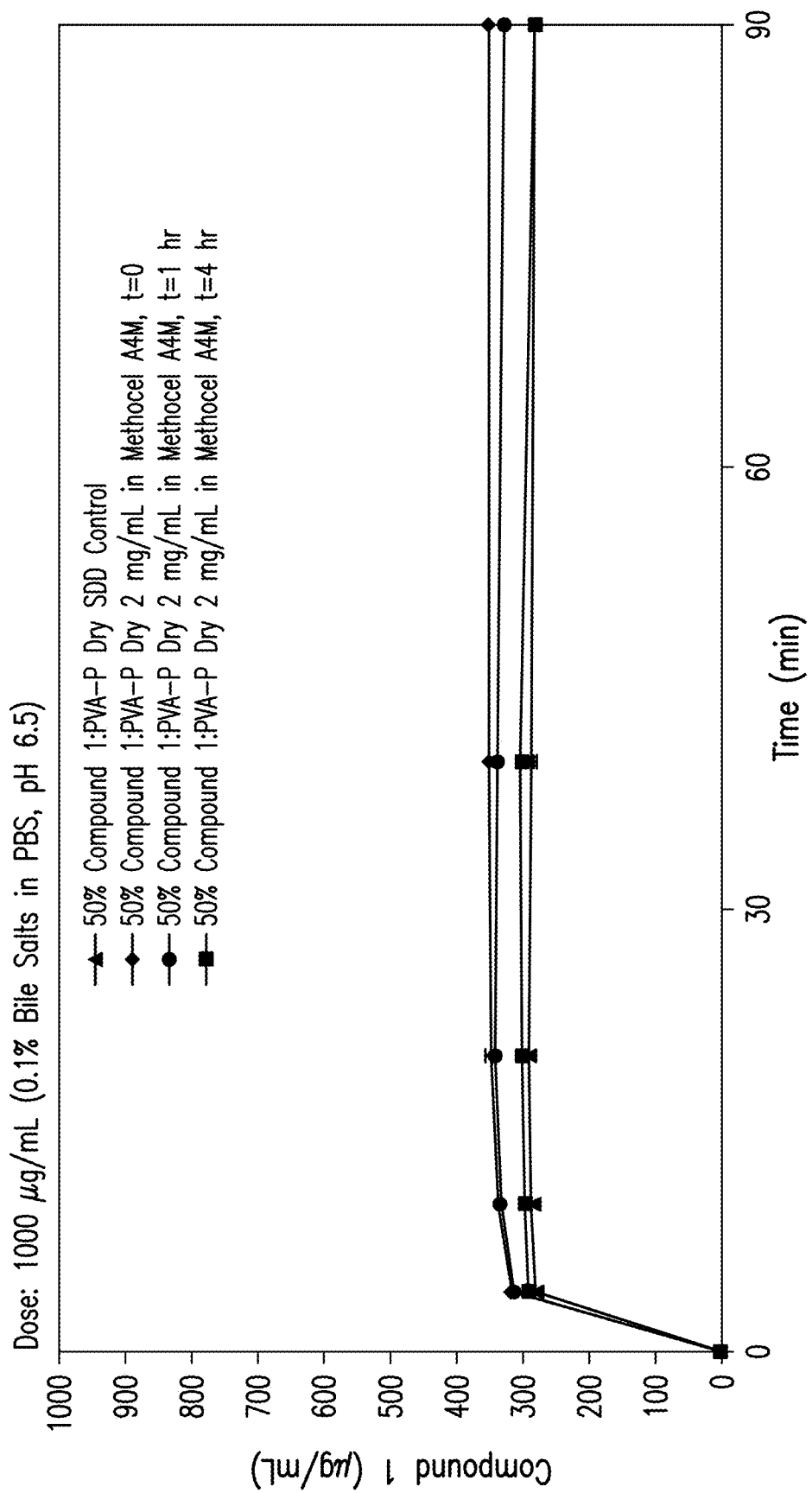
FIG. 45 shows the suspension stability of Capsule H in Methocel.

FIG. 45 shows the suspension stability of Capsule H in Methocel.

Figure 46:
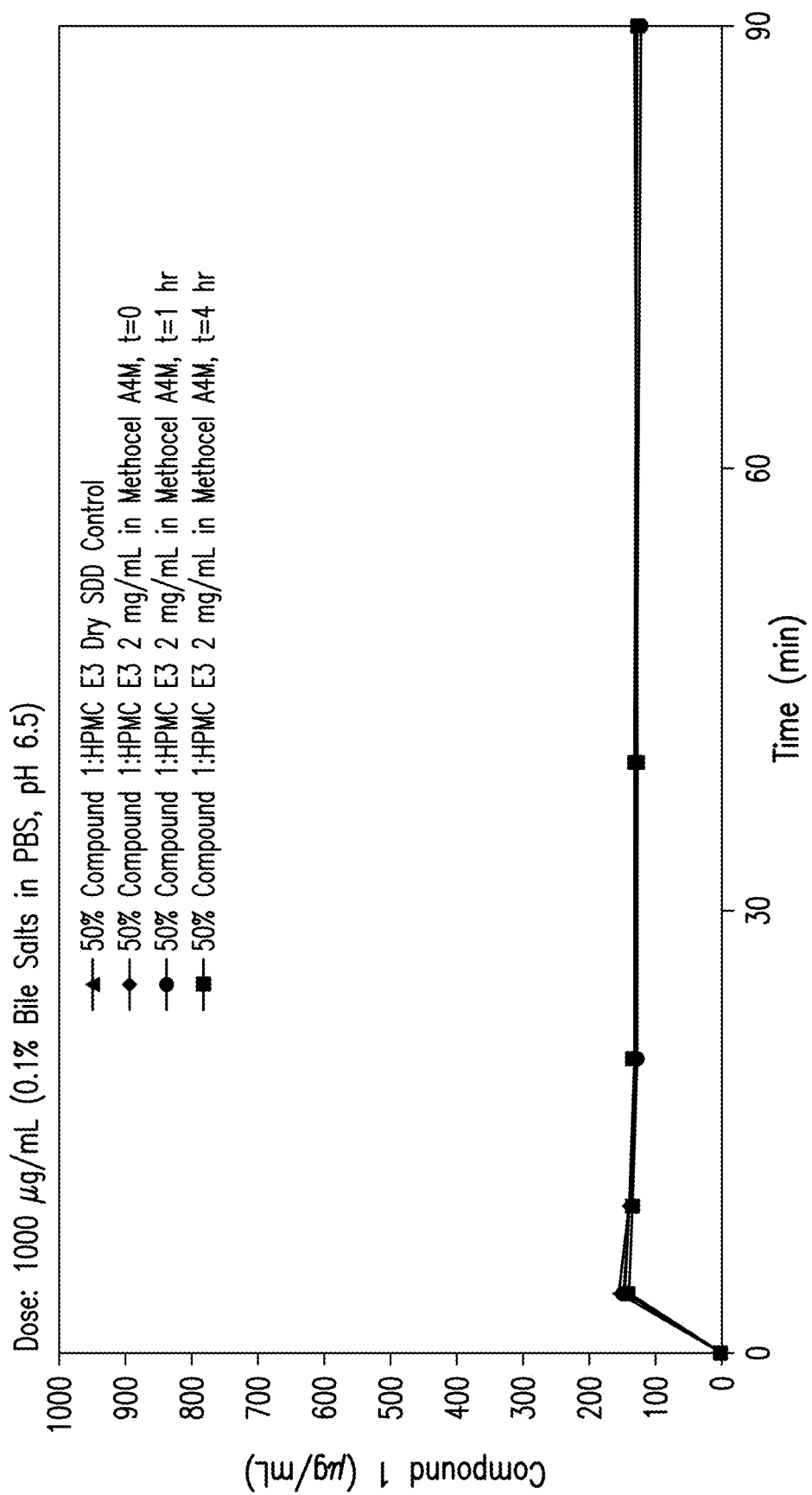
FIG. 46 shows the suspension stability of Capsule G in Methocel.

FIG. 46 shows the suspension stability of Capsule G in Methocel.

Figure 47:
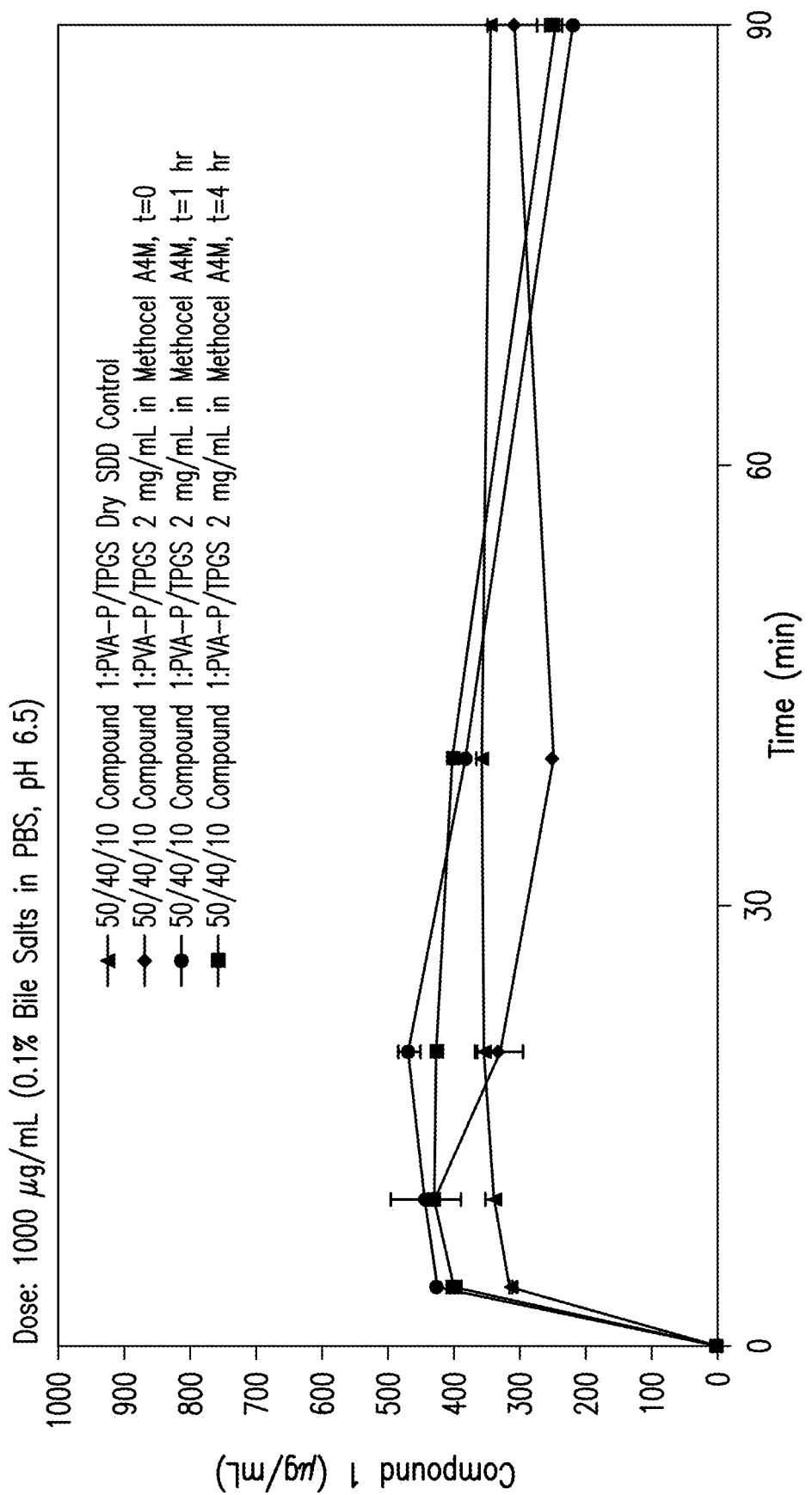
FIG. 47 shows the suspension stability of Capsule E in Methocel.

FIG. 47 shows the suspension stability of Capsule E in Methocel.

Figure 48:
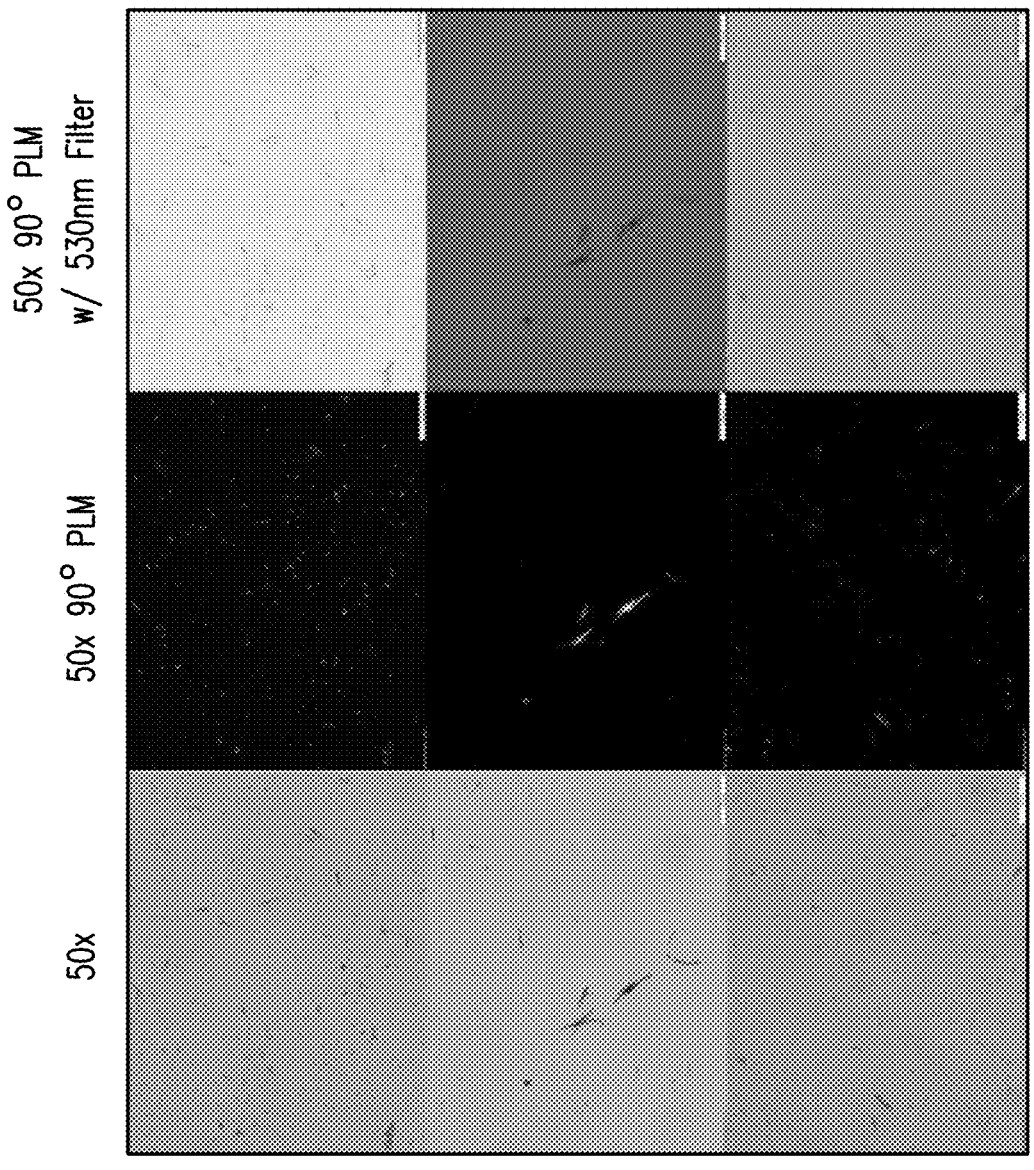
FIG. 48 shows the suspension stability, as visualized by PLM, of Capsule A in Methocel.

FIG. 48 shows the suspension stability, as visualized by PLM, of Capsule A in Methocel.

Figure 49:
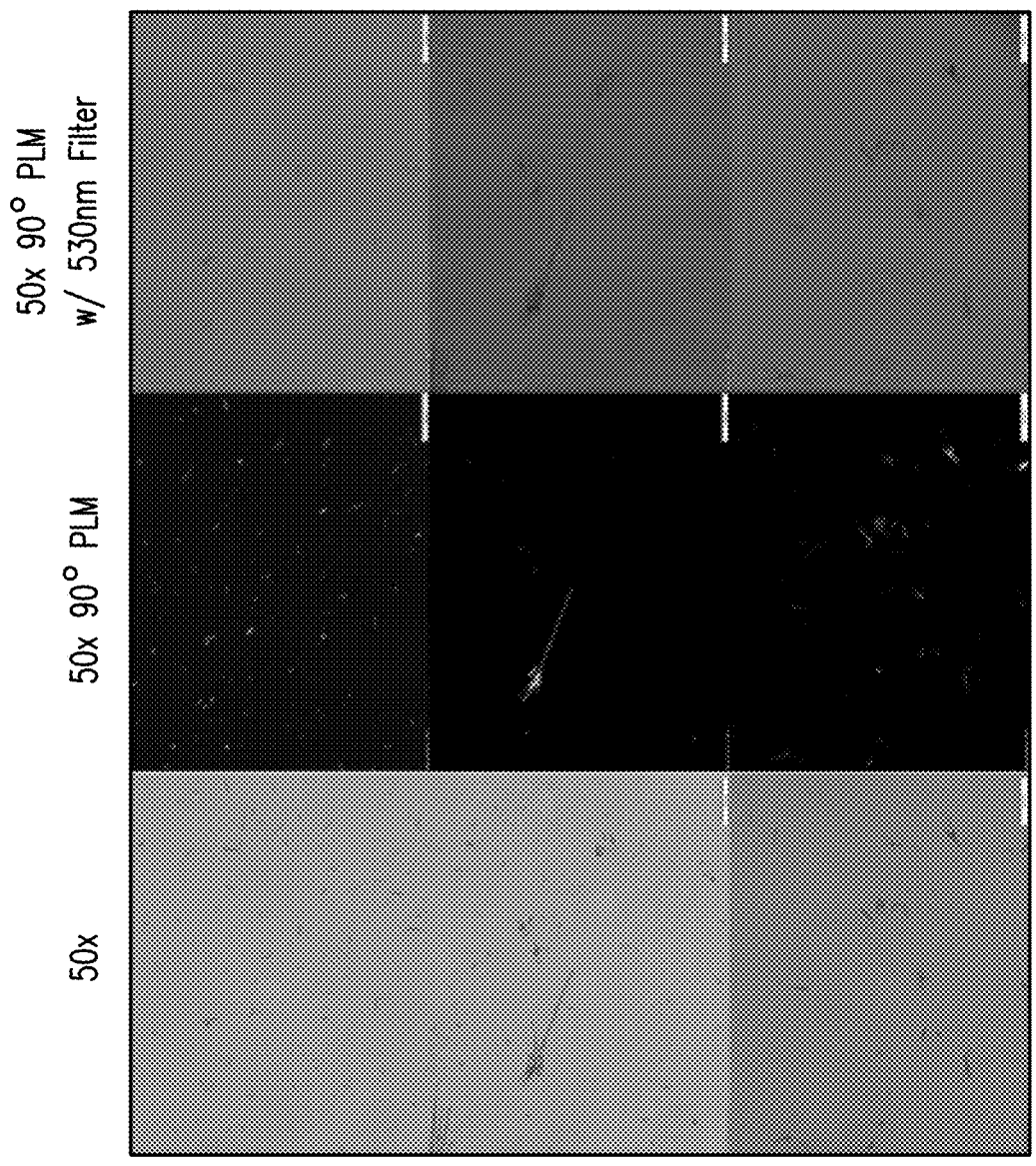
FIG. 49 shows the suspension stability, as visualized by PLM, of Capsule H in Methocel.

FIG. 49 shows the suspension stability, as visualized by PLM, of Capsule H in Methocel.

Figure 50:
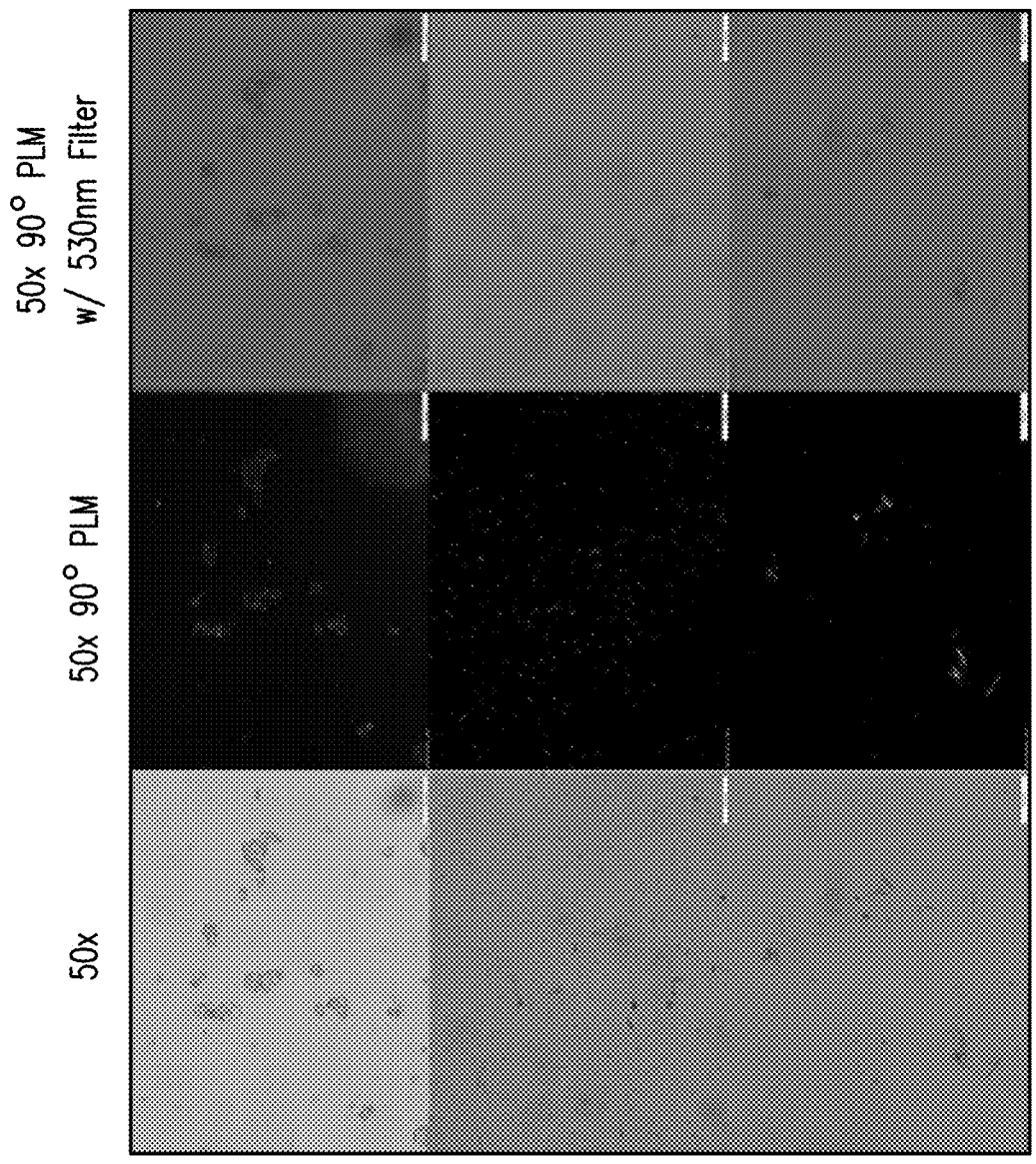
FIG. 50 shows the suspension stability, as visualized by PLM, of Capsule G in Methocel.

FIG. 50 shows the suspension stability, as visualized by PLM, of Capsule G in Methocel.

Figure 51:
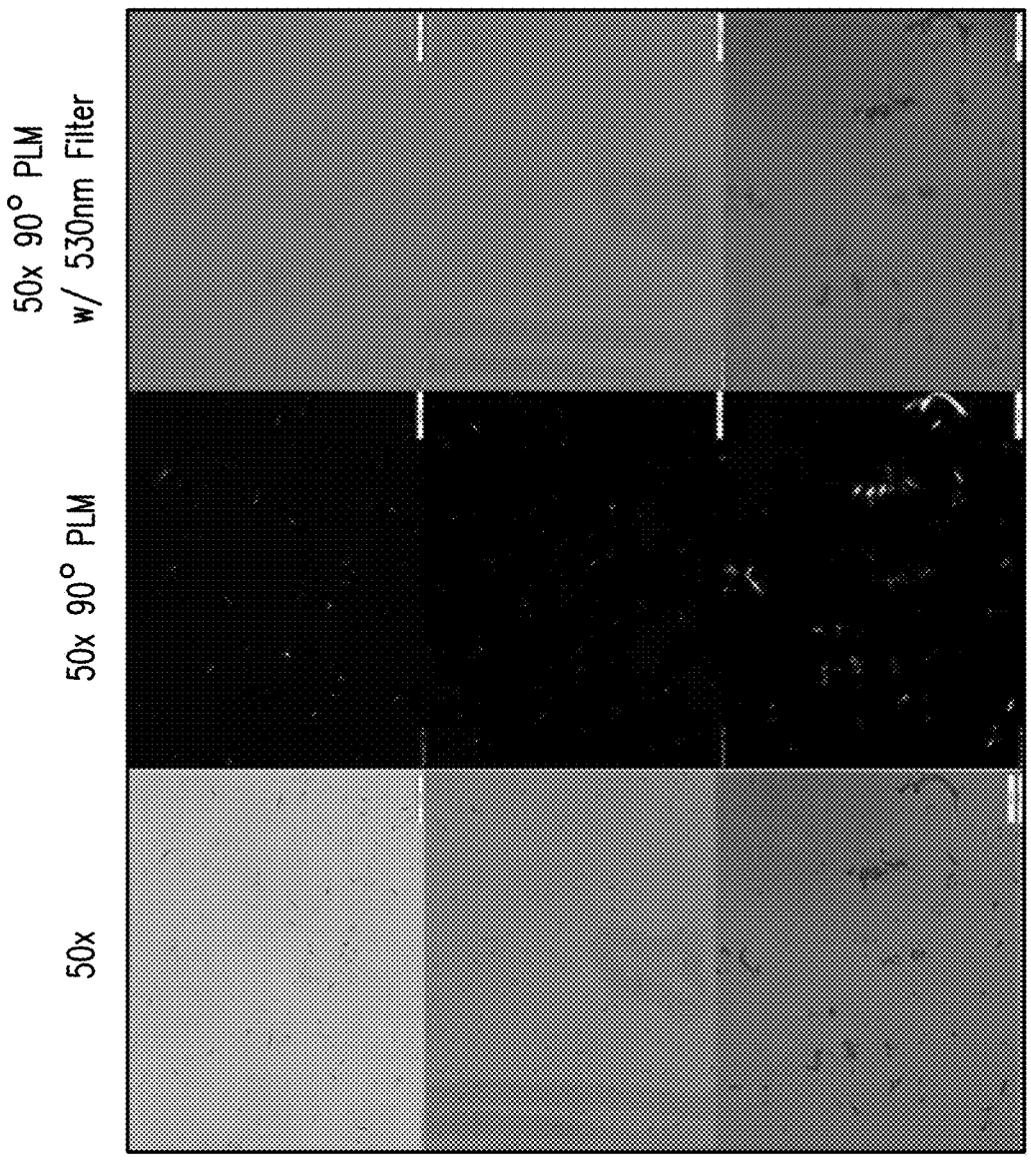
FIG. 51 shows the suspension stability, as visualized by PLM, of Capsule E in Methocel.

FIG. 51 shows the suspension stability, as visualized by PLM, of Capsule E in Methocel.

6.31 Mouse in vivo Pharmacokinetic Study

TABLE 45 mTOR + CD-1 Male Mouse Oral Dosing Pharmacokinetic Parameters

| CD-1 Male Mouse PK Parameters | Mean Value[1] | | | | Mean ± SD (N = 4) | |
|---|---|---|---|---|---|---|
| | Capsule G | Capsule E | Capsule A | Capsule H | Capsule I[2] | Capsule J[3] |
| Cmax (µM) | 1.16 | 0.902 | 0.703 | 0.612 | 0.464 ± 0.182 | 1.42 ± 0.549 |
| Tmax (hr) | 0.25 | 0.25 | 0.25 | 0.50 | 0.50 ± 0.00 | 0.50 ± 0.00 |
| $AUC_{(0-inf)}$ (µM · hr) | 1.12 | 1.00 | 1.36 | 1.41 | 1.24 ± 0.24 | 2.49 ± 0.68 |
| F % | 8.6 | 7.7 | 10 | 11 | 10 | 19 |

[1]Data obtained via non-serial sampling from two groups with n = 4 per group.
[2]Capsule I comprises .5% HPMC/1% TPGS.
[3]Capsule J comprises CMC/Tween.

This study evaluated the effect of two Spayed-dried dispersion (SDD) formulations Capsule G, Capsule E, Capsule A, and Capsule H on oral exposure of Compound 1 in male CD-1 mice at 10 mg/kg. The SDD formulations had 5000 loading of Compound 1. The overall exposure was comparable between the two DSS formulations. The exposure data was also similar to those from the other three tested formulations. Overall, all tested formulations did not improve exposure of Compound 1 in CD-1 mice at 10 mg/kg compared to the standard formulation in CMC/Tween. The results were as expected since solubility/dissolution of this compound was not the major limiting factor to exposure at low dose levels.

Table 46 shows the plasma concentration profile results following a single oral administration of Capsule G in male CD-1 mice.

TABLE 46

Capsule G: Tabular Summary of Plasma Concentration (µM)

Plasma Concentration of Compound 1 (µM)

| Time (hr) | Mouse 1/9 | Mouse 2/10 | Mouse 3/11 | Mouse 4/12 | Mean | SD |
|---|---|---|---|---|---|---|
| 0 | 0.00 | 0.00 | 0.0 | 0.00 | 0.0 | 0.0 |
| 0.25 | 0.891 | 0.975 | 2.42 | 0.364 | 1.162 | 0.881 |
| 0.5 | 0.990 | 0.230 | 0.533 | 0.413 | 0.541 | 0.324 |
| 1 | 0.224 | 0.265 | 0.657 | 0.062 | 0.302 | 0.252 |
| 2 | 0.179 | 0.145 | 0.072 | 0.163 | 0.140 | 0.048 |
| 4 | 0.0156 | 0.0538 | 0.0387 | 0.0065 | 0.0287 | 0.0216 |
| 6 | BLQ | 0.0189 | 0.0340 | 0.0356 | 0.0221 | 0.0166 |
| 8 | 0.035 | 0.0270 | 0.0113 | 0.0104 | 0.0209 | 0.0121 |
| 24 | BLQ | BLQ | BLQ | BLQ | BLQ | NC |

BLQ: below the limit of quantitation;
NC: not calculable.

Figure 52:
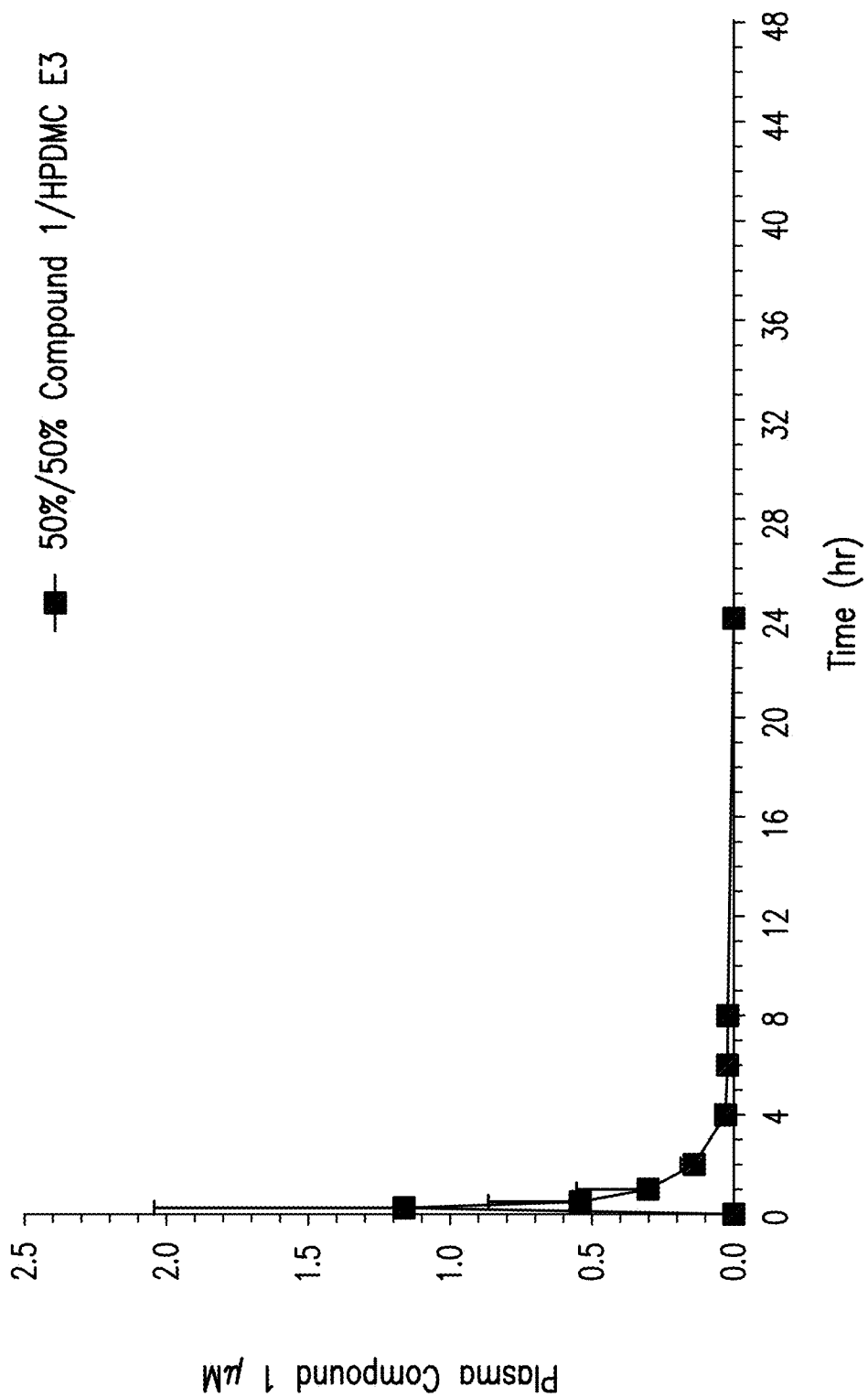
FIG. 52 shows the plasma concentration profile results following a single oral administration of Capsule G in male CD-1 mice.

FIG. 52 shows the plasma concentration profile results following a single oral administration of Capsule G in male CD-1 mice.

Table 47 shows the plasma concentration profile results following a single oral administration of Capsule E in male CD-1 mice.

TABLE 47

Capsule E: Tabular Summary of Plasma Concentration (µM)

Plasma Concentration of Compound 1 (µM)

| Time (hr) | Mouse 1/9 | Mouse 2/10 | Mouse 3/11 | Mouse 4/12 | Mean | SD |
|---|---|---|---|---|---|---|
| 0 | 0 | 0.0 | 0.00 | 0 | 0 | 0 |
| 0.25 | 0.570 | 0.601 | 1.622 | 0.817 | 0.902 | 0.492 |
| 0.5 | 0.293 | 0.978 | 0.539 | 0.277 | 0.522 | 0.327 |

TABLE 47-continued

Capsule E: Tabular Summary of Plasma Concentration (μM)

Plasma Concentration of Compound 1 (μM)

| Time (hr) | Mouse 1/9 | Mouse 2/10 | Mouse 3/11 | Mouse 4/12 | Mean | SD |
|---|---|---|---|---|---|---|
| 1.0 | 0.273 | 0.225 | 0.248 | 0.178 | 0.231 | 0.040 |
| 2 | 0.118 | 0.189 | 0.250 | 0.124 | 0.170 | 0.062 |
| 4 | 0.0420 | 0.0255 | 0.023 | 0.0361 | 0.0317 | 0.0089 |
| 6 | *0.0341* | BLQ | 0.0243 | 0.0217 | 0.0200 | 0.0144 |
| 8 | 0.0109 | 0.0110 | 0.0106 | 0.0102 | 0.0107 | 0.0004 |
| 24 | BLQ | BLQ | *0.00126* | BLQ | BLQ | NC |

BLQ: below the limit of quantitation;
NC: not calculable;
values in italics are estimated.

Figure 53:
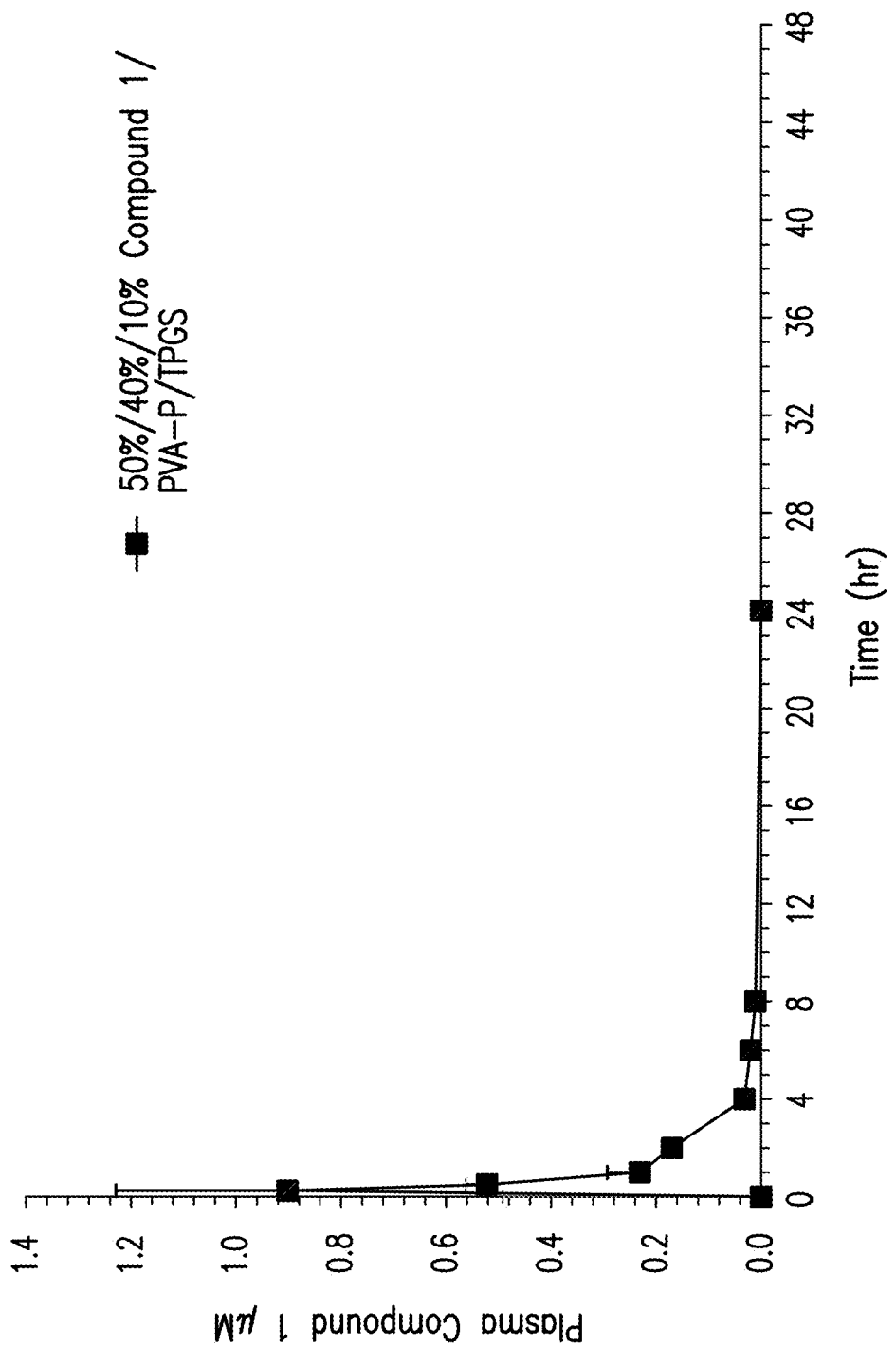
FIG. 53 shows the plasma concentration profile results following a single oral administration of Capsule E in male CD-1 mice.

FIG. 53 shows the plasma concentration profile results following a single oral administration of Capsule E in male CD-1 mice.

Table 48 shows the plasma concentration profile results following a single oral administration of Capsule 1 in male CD-1 mice.

TABLE 48

Capsule I: Tabular Summary of Plasma Concentration (μM)

Plasma Concentration of Compound 1 (μM)

| Time (hr) | Mouse 1 | Mouse 2 | Mouse 3 | Mouse 4 | Mean | SD |
|---|---|---|---|---|---|---|
| 0 | 0 | 0 | 0 | 0 | 0 | 0 |
| 0.5 | 0.357 | 0.377 | 0.736 | 0.385 | 0.464 | 0.182 |
| 1.5 | 0.150 | 0.092 | 0.223 | 0.191 | 0.164 | 0.056 |
| 3 | 0.125 | 0.0717 | 0.0926 | 0.171 | 0.115 | 0.043 |
| 5 | 0.0795 | 0.0568 | 0.0388 | 0.1042 | 0.0698 | 0.0283 |
| 8 | 0.0710 | 0.0326 | 0.0614 | 0.0365 | 0.0504 | 0.0187 |

Figure 54:
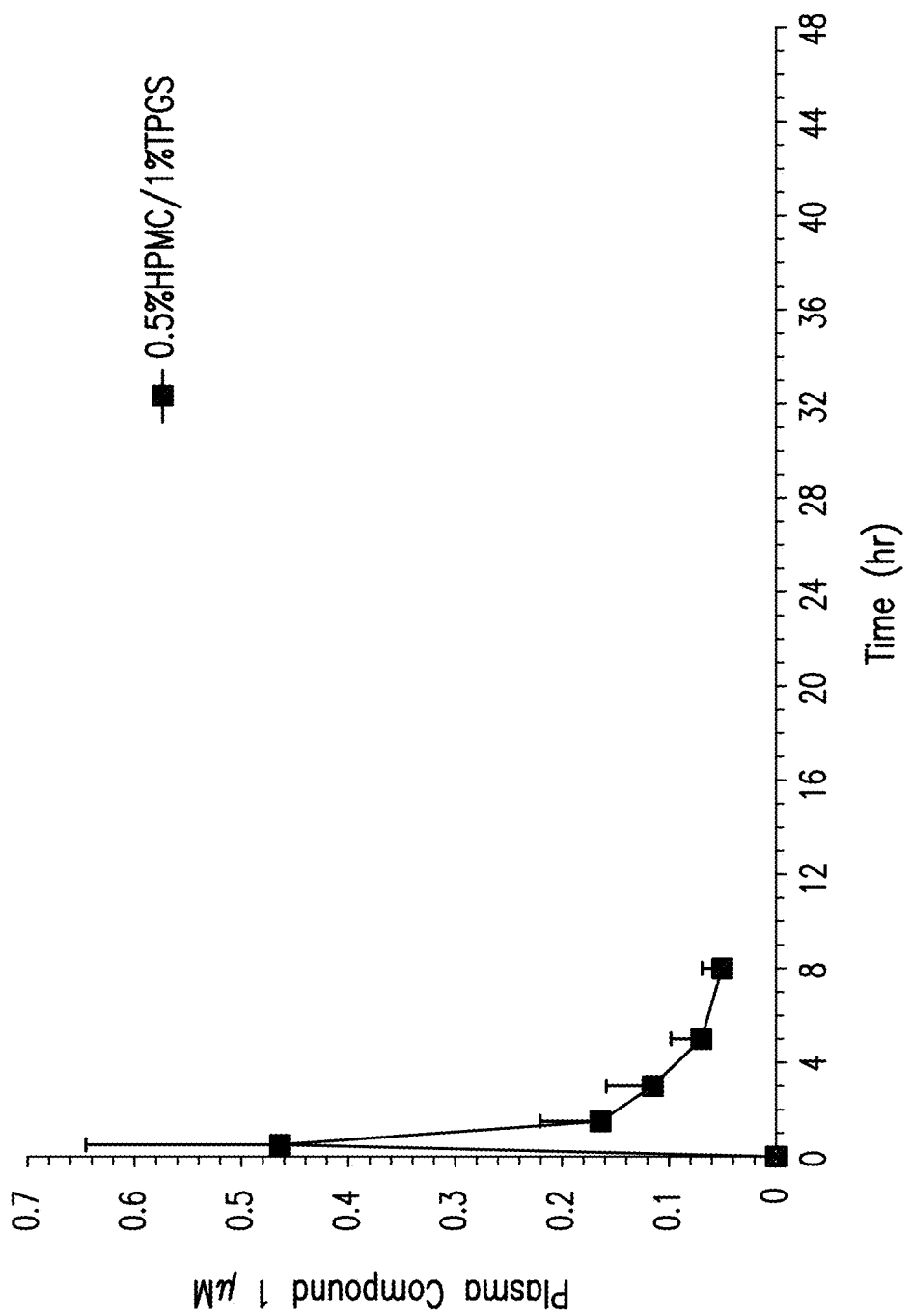
FIG. 54 shows the plasma concentration profile results following a single oral administration of Capsule I in male CD-1 mice.

FIG. 54 shows the plasma concentration profile results following single oral administration of Capsule I in male CD-1 mice.

Table 49 shows the plasma concentration profile results following a single oral administration of Capsule J in male CD-1 mice.

TABLE 49

Capsule J: Tabular Summary of Plasma Concentration (μM)

Plasma Concentration of Compound 1 (μM)

| Time (hr) | Mouse 1/9 | Mouse 2/10 | Mouse 3/11 | Mouse 4* | Mean | SD |
|---|---|---|---|---|---|---|
| 0 | 0 | 0 | 0 | 0 | 0 | 0 |
| 0.5 | 0.845 | 1.46 | 1.94 | 3.54 | 1.42 | 0.55 |
| 1.5 | 0.275 | 0.702 | 0.578 | 0.962 | 0.519 | 0.220 |
| 3 | 0.285 | 0.301 | 0.192 | 1.85 | 0.259 | 0.059 |
| 5 | 0.0500 | 0.0653 | 0.0702 | 0.292 | 0.0618 | 0.0105 |
| 8 | 0.0259 | 0.0621 | 0.0341 | 0.0372 | 0.0407 | 0.0190 |

*Mouse 4 is an outlier based on Grubb's test, and therefore excluded for data analysis.

Figure 55:
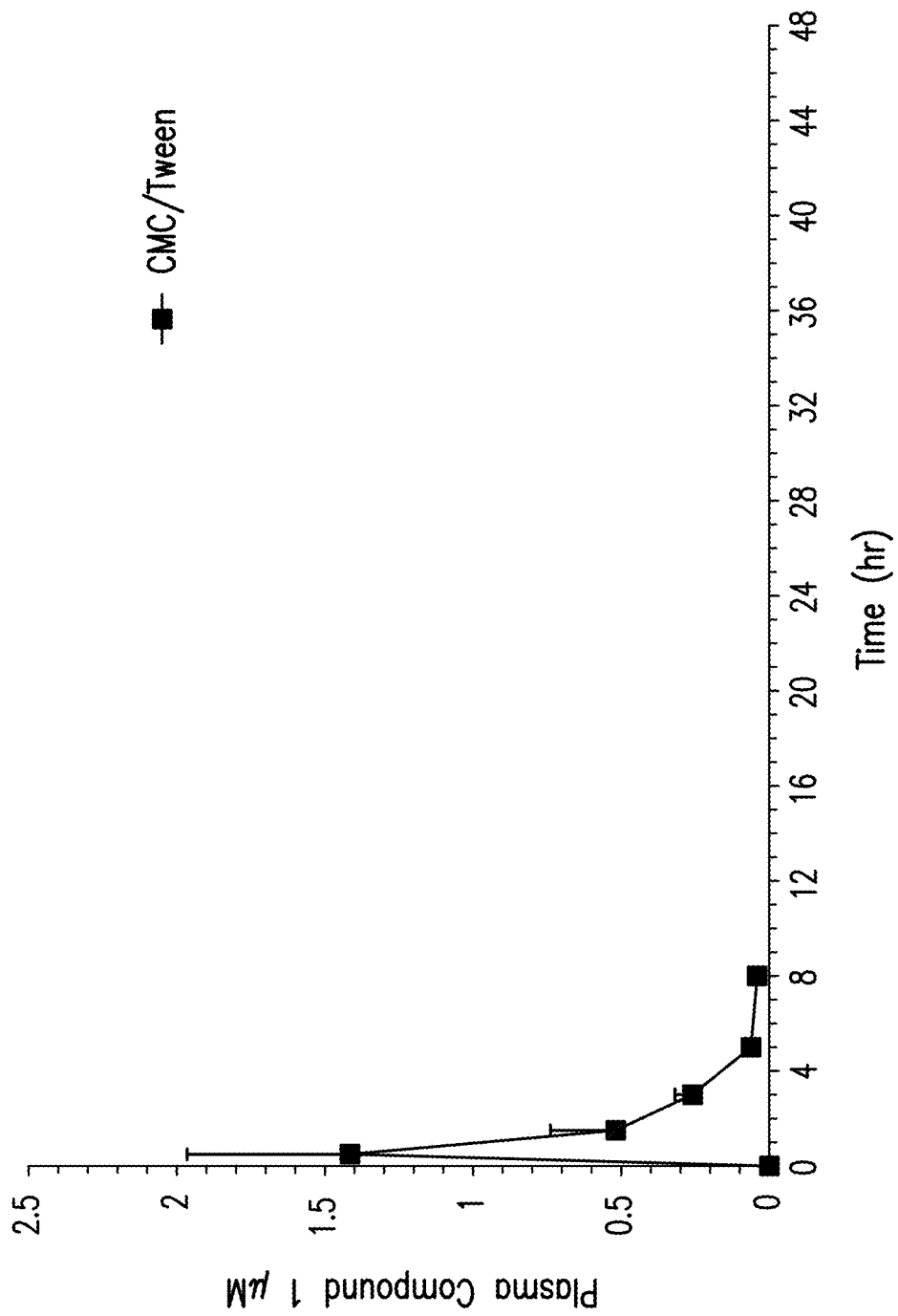
FIG. 55 shows the plasma concentration profile results following a single oral administration of Capsule J in male CD-1 mice.

FIG. 55 shows the plasma concentration profile results following a single oral administration of Capsule J in male CD-1 mice.

Figure 56:
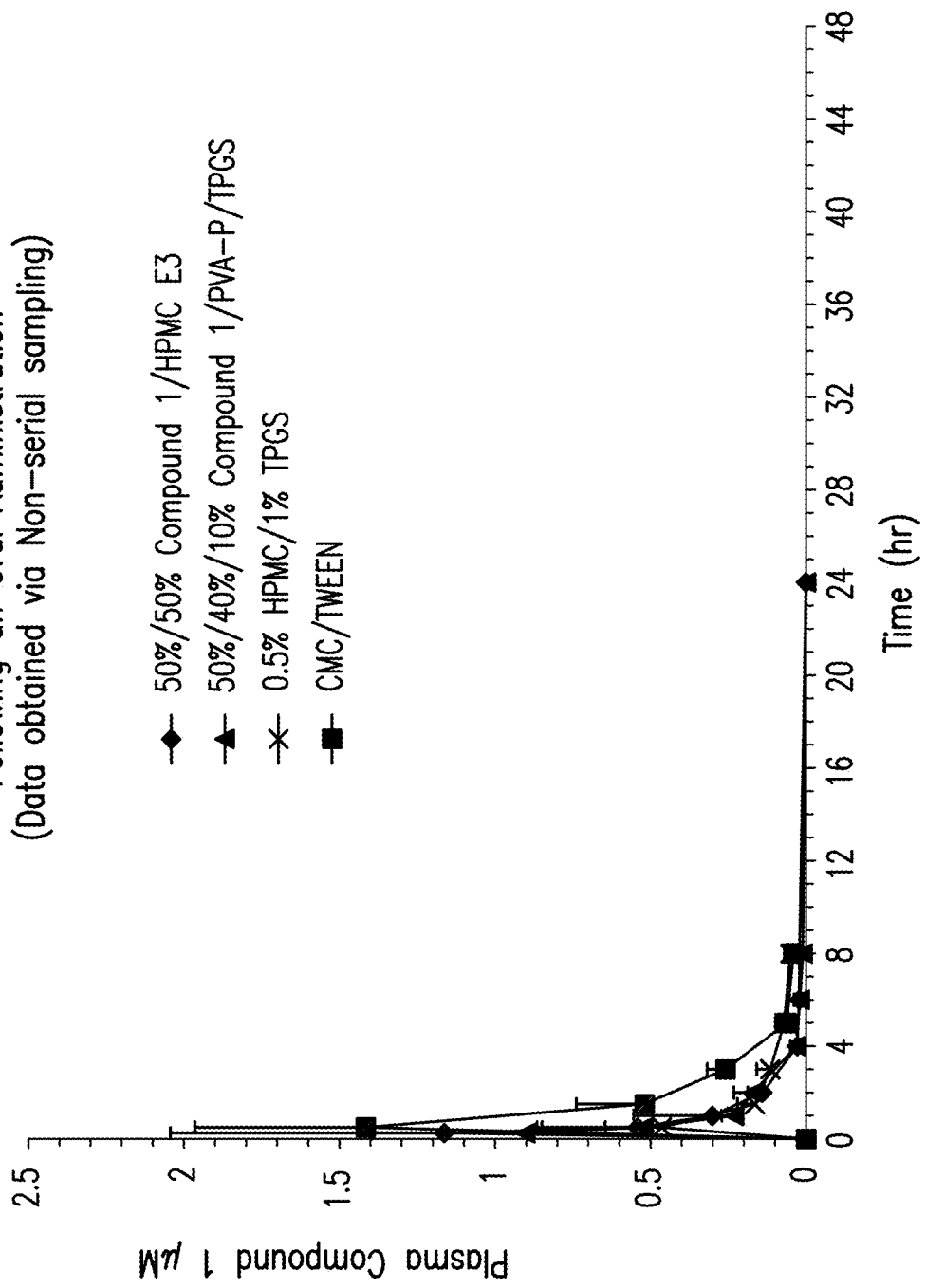
FIG. 56 shows a comparison of the concentration profile results following a single oral administration of Capsule G, Capsule E, Capsule I, and Capsule J.

FIG. 56 shows a comparison of the concentration profile results following a single oral administration of Capsule G, Capsule E, Capsule I, and Capsule J.

6.32 Tablets

Tablets A-C were produced and examined in the below studies.

Table 50 shows the composition of Tablet A.

TABLE 50

Composition of Tablet A

| Ingredient | Composition (% w/w) | Amount (mg per tablet) |
| --- | --- | --- |
| Compound 1 | 20 | 50 |
| Microcrystalline cellulose (Avicel PH102) | 37.25 | 93.125 |
| EMPROVE ® Parteck ® | 37.25 | 93.125 |
| Ac-Di-Sol ® | 4 | 10 |
| AEROSIL ® 200 | 0.5 | 1.25 |
| Magnesium stearate | 1 | 2.5 |
| Total | 100 | 250 |

Table 51 shows the composition of Tablet B.

TABLE 51

Composition of Tablet B

| Ingredient | Composition (% w/w) | Amount (mg per tablet) |
| --- | --- | --- |
| HCl Salt of Compound 1 | 20 | 50 |
| Microcrystalline cellulose (Avicel PH102) | 37.25 | 93.125 |
| EMPROVE ® Parteck ® | 37.25 | 93.125 |
| Ac-Di-Sol ® | 4 | 10 |
| AEROSIL ® 200 | 0.5 | 1.25 |
| Magnesium stearate | 1 | 2.5 |
| Total | 100 | 250 |

Table 52 shows the composition of Tablet C.

TABLE 52

Composition of Tablet C

| Ingredient | Composition (% w/w) | Amount (mg per tablet) |
| --- | --- | --- |
| Citrate Salt of Compound 1 | 20 | 50 |
| Microcrystalline cellulose (Avicel PH102) | 37.25 | 93.125 |
| EMPROVE ® Parteck ® | 37.25 | 93.125 |
| Ac-Di-Sol ® | 4 | 10 |
| AEROSIL ® 200 | 0.5 | 1.25 |
| Magnesium stearate | 1 | 2.5 |
| Total | 100 | 250 |

Figure 57:
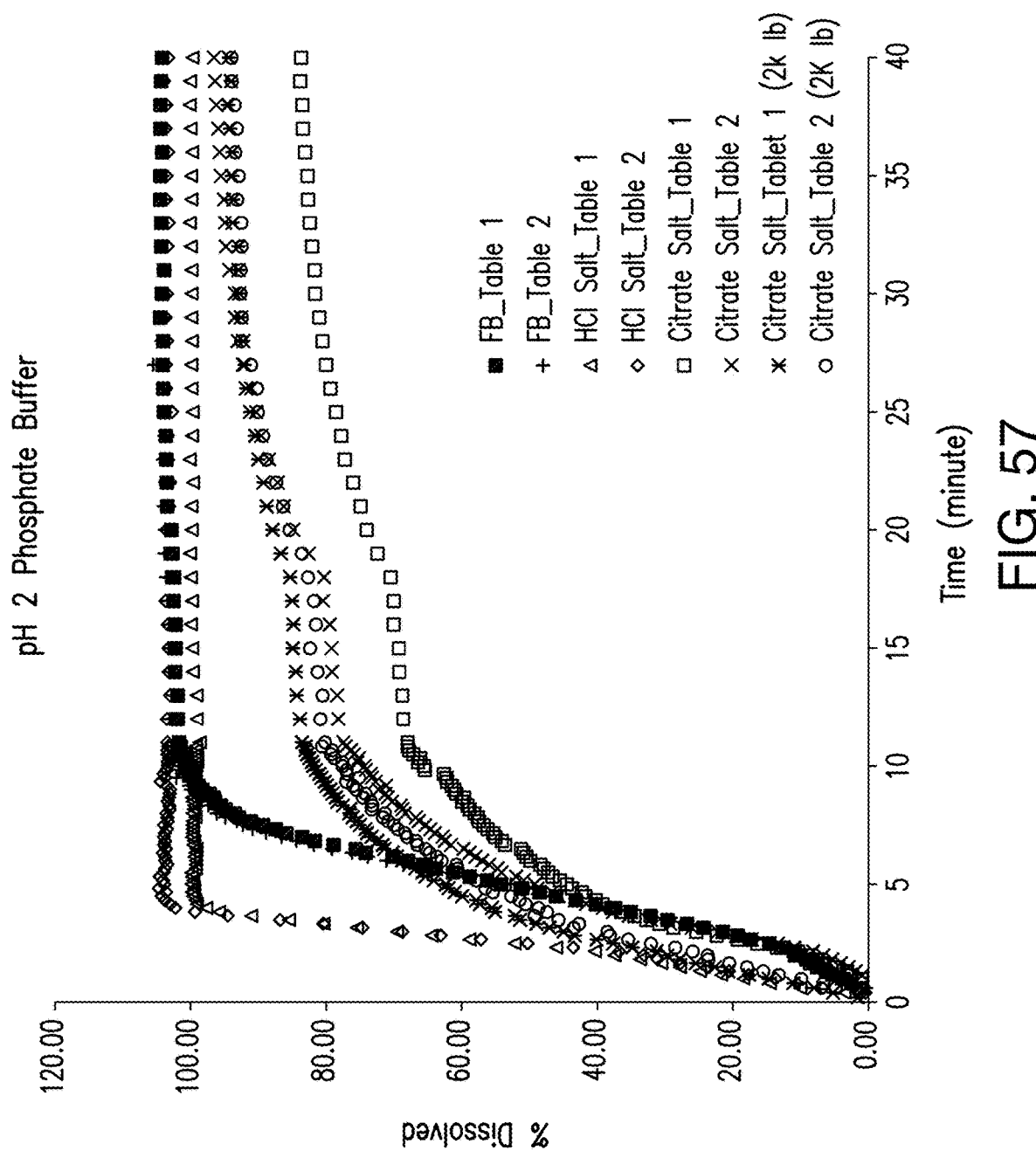
FIG. 57 shows the dissolution of Tablet A, Tablet B, and Tablet C in pH 2 phosphate buffer.

FIG. 57 shows the dissolution of Tablet A, Tablet B, and Tablet C in pH 2 phosphate buffer.

Figure 58:
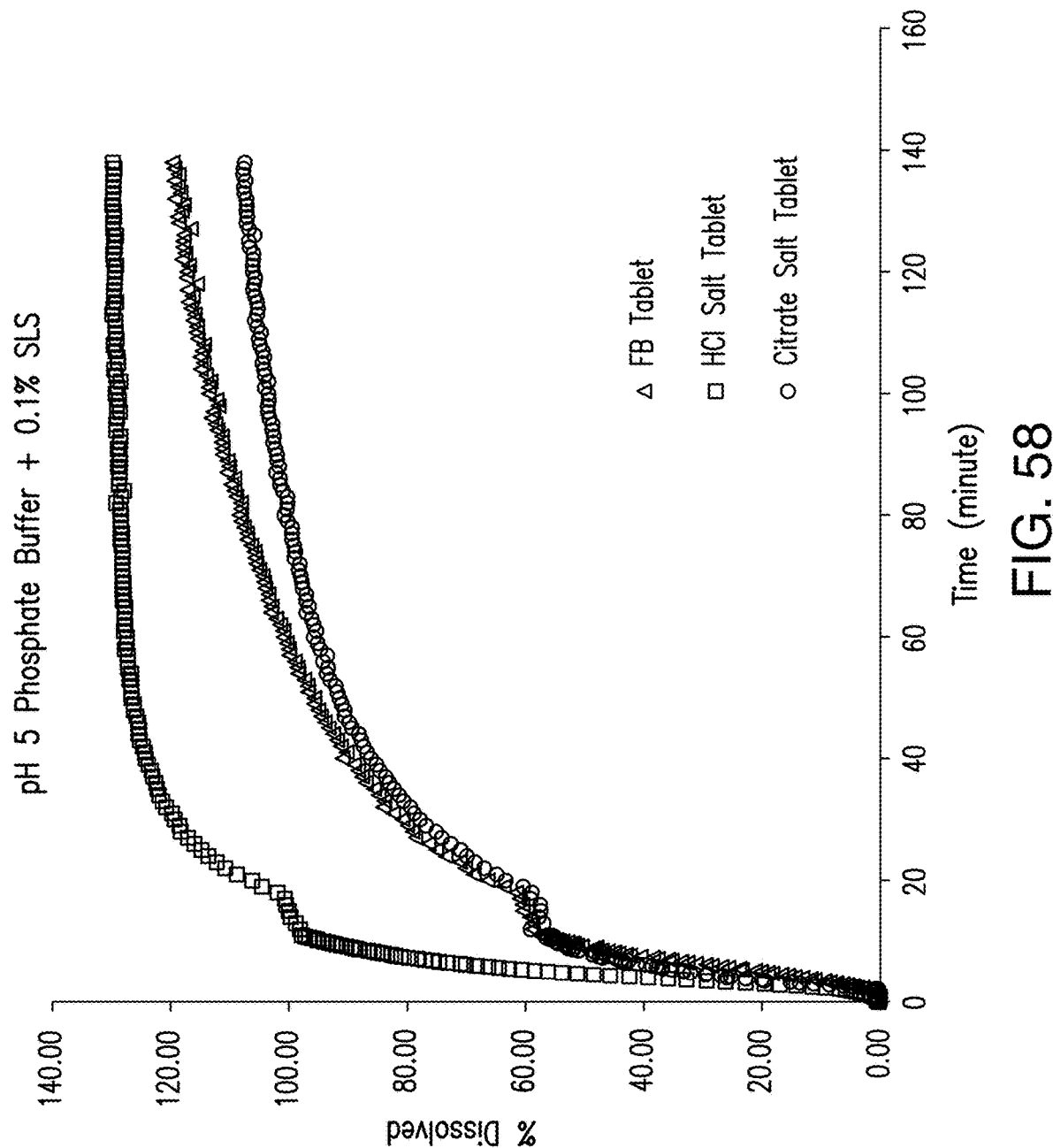
FIG. 58 shows the dissolution of Tablet A (middle curve), Tablet B (top curve), and Tablet C (bottom curve) in pH 5 phosphate buffer and 0.1% sodium laureth sulfate.

FIG. 58 shows the dissolution of Tablet A (middle curve), Tablet B (top curve), and Tablet C (bottom curve) in pH 5 phosphate buffer and 0.1% sodium laureth sulfate. The HCl salt of Compound 1 had a higher dissolution than the free base of Compound 1 and the citrate salt of Compound 1.

6.33 Example 4: Formulation and Stability Study

Solubility Study: Compound 1 free base pKa was determined to be 5.14. Therefore, solubility of Compound 1 is pH dependent: 0.003 mg/ml in water (pH 8.1), 3.5 mg/ml in simulated gastric fluids (SGF) (pH 1.9), 0.002 mg/ml in the simulated intestinal fluids (SIF) (pH 7.3). Solubility in the preclinical formulation, 0.5% CMC/0.25% Tween 80, was determined to be 0.18 mg/ml at pH 8.1. Solubilities of Compound 1 in SGF and SIF under the fasted and fed conditions are listed in Table 53.

TABLE 53

Solubility of Compound 1 Freebase Monohydrate in Bio-relevant Media at 24 Hours

| Vehicles | Concentration (mg/mL) | pH @ 24 hr |
| --- | --- | --- |
| FaSSIF | 0.26 | 6.48 |
| FeSSIF | 2.07 | 4.94 |
| FaSSGF | 2.81 | 1.84 |
| FeSSGF | 0.004 | 6.31 |

Chemical Stability Study: Solid state stability of Compound 1 free base monohydrate was evaluated at 80° C. for 2 weeks and 40° C./75% RH, 50° C./75% RH and 60° C. for up to 5 weeks. The results indicated that Compound 1 free base monohydrate is chemically relatively stable under all storage conditions and durations.

Physical Stability Study: The free base monohydrate lost water and converted to a dehydrate form after being heated at 60 and 80° C. This dehydrate form converted back to monohydrate immediately when samples were exposed to room temperature and RH>30%. If RH is in the range of 5-30%, the dehydrate form may take 1-3 days to convert back to monohydrate.

6.34 Solution Stability Study:

The solution stability of Compound 1 free base in water, SGF (pH 1.3), SIF (pH 7.5), and 0.1N NaOH with and without light protection at 37° C. was tested. The results showed that Compound 1 free base is relatively stable (>95% remaining) in all vehicles for 4 days except for the sample in 0.1N NaOH without light protection. Significant degradation was observed for this sample, only 88% remaining at day 1 and 61% remaining at day 4.

No significant degradation was observed for a 6 mg/mL suspension formulation in 0.5% CMC and 0.25% Tween 80, stored at ambient temperature and 2-8° C. for 7 days.

6.35 Formulation Development

Free Base Monohydrate

To assess the feasibility of using Compound 1 in a capsule to support FIH study, a dissolution study with a capsule containing 125 mg Compound 1 free base monohydrate was performed in the media of 0.01N HCl and 0.001N HCl at 37° C. Capsule shell shrinkage was observed. About 80% Compound 1 was released in 0.01N HCl and only 10% in 0.001N HCl at 60 minutes, suggesting that dissolution of Compound 1 free base monohydrate was highly pH dependent and developing a AIC formulation for freebase monohydrate to support FIH study may be challenging. Blend in capsule or other formulation approaches may be necessary.

Citrate Salt

Figure 59:
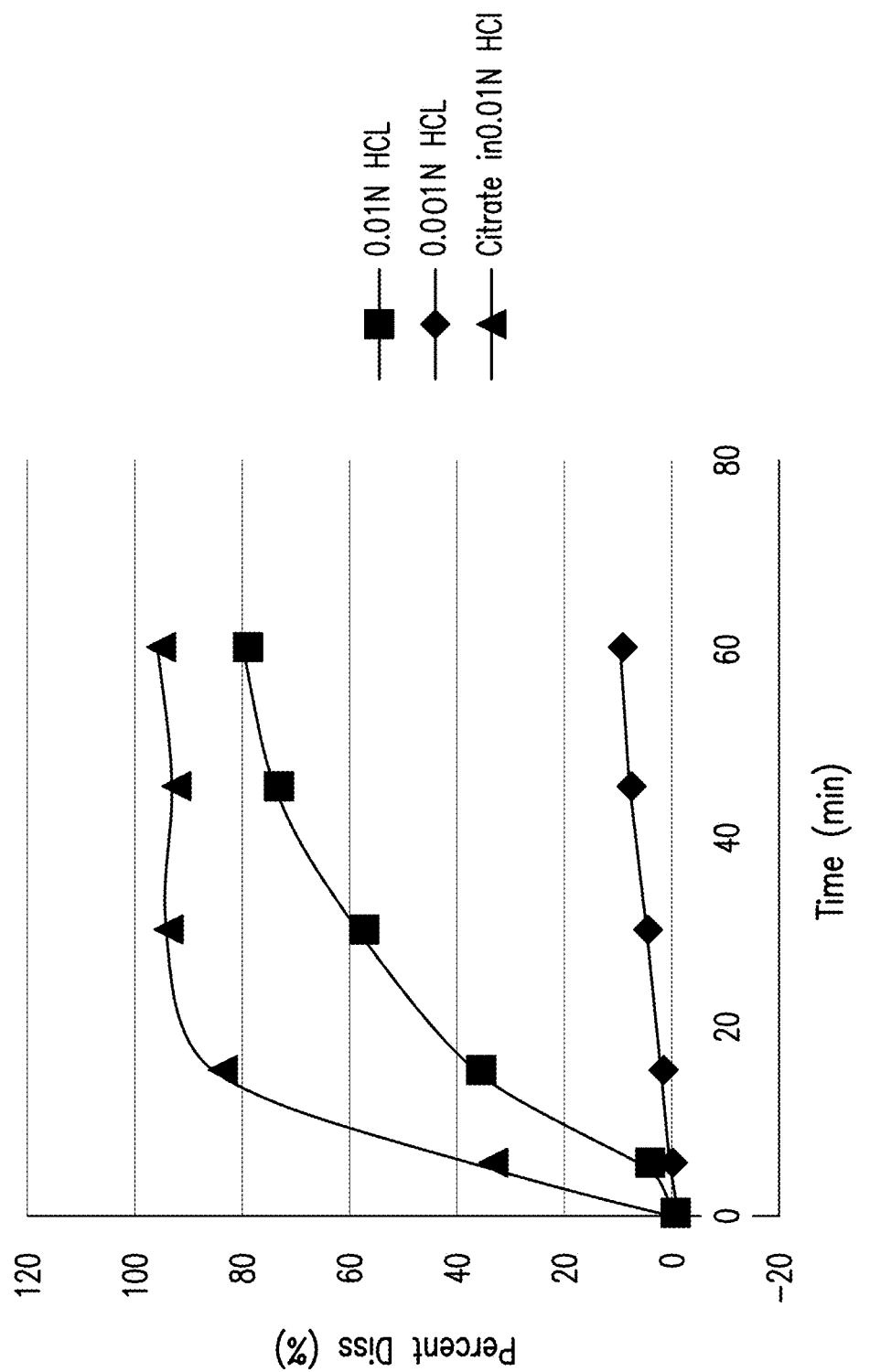
FIG. 59 shows that a citrate salt had a better dissolution profile compared to a freebase monohydrate.

A dissolution study for citrate salt in a capsule in 0.01N HCl was also carried out. The results as provided in FIG. 59 showed that citrate salt had a better dissolution profile compared to freebase monohydrate suggesting AIC formulation approach to support FIH may be feasible for citrate salt.

What is claimed is:

1. A method for achieving a Response Evaluation Criteria in Solid Tumors (RECIST 1.1) of complete response, partial response or stable disease in a patient having a solid tumor, comprising administering to the patient an effective amount of a formulation, wherein the formulation is a capsule comprising cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof in an amount that is 30-40% of the capsule by weight, an excipient in an amount that is 50-60% of the capsule by weight, and tocophersolan in an amount that is 5-15% of the capsule by weight, a capsule comprising 60-70% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 20-30% of an excipient by weight, and 5-15% of tocophersolan by weight, a capsule comprising 45-55% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 35-45% of an excipient by weight, and 5-15% of tocophersolan by weight, a capsule comprising a citrate salt of cis-4-[2-{[(3S,4R)-3-fluorooxan-4-yl]amino}-8-(2,4,6-trichloroanilino)-9H-purin-9-yl]-1-methylcyclohexane-1-carboxamide in an amount that is 0.5-20% of the capsule weight, and sodium lauryl sulfate, or a tablet comprising 15-25% of cis-4-[2-{[(3S,4R)-3-fluorooxan-4-yl]amino}-8-(2,4,6-trichloroanilino)-9H-purin-9-yl]-1-methylcyclohexane-1-carboxamide or an isotopologue, pharmaceutically acceptable salt, tautomer, solvate, hydrate, co crystal, clathrate, or polymorph thereof by weight, 32-43% of microcrystalline cellulose by weight, 32-43% of mannitol by weight, 2-6% of croscarmellose sodium by weight, 0.3-0.7% of fumed silica by weight, and 0.5-1.5% magnesium stearate by weight.

2. The method of claim 1, wherein the solid tumor is melanoma, colorectal cancer, stomach cancer, head and neck cancer, thyroid cancer, bladder cancer, CNS cancer, lung cancer, pancreatic cancer, or soft tissue cancer.

3. The method of claim 1, wherein the solid tumor is bladder cancer, breast cancer, CNS cancer, colon cancer, gastrointestinal cancer, endocrine cancer, female genitoureal cancer, head and neck cancer, hematopoietic cancer, kidney cancer, liver cancer, lung cancer, melanoma, pancreas cancer, prostate cancer, or soft tissue cancer.

4. The method of claim 1, wherein the solid tumor is glioma, neuroblastoma, stomach cancer, thyroid cancer, adrenal gland cancer, cancer of the uterus, cervix, ovary clear cell, or vulva, leukemia, myeloma, non-small cell lung cancer (NSCLC), small cell lung cancer (SCLC), sarcoma or osteosarcoma.

5. The method of claim 1, wherein the solid tumor is hepatocellular carcinoma (HCC).

6. The method of claim 1, wherein the solid tumor is colorectal cancer (CRC), melanoma, gastric cancer, hepatocellular carcinoma, lung cancer, pancreatic cancer, leukemia, multiple myeloma, stomach cancer or sarcoma.

7. A method for achieving complete remission, partial remission or stable disease, as determined by the International Workshop Criteria (IWC) for NHL in a patient having a cancer, comprising administering to the patient an effective amount of a formulation, wherein the formulation is a capsule comprising cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof in an amount that is 30-40% of the capsule by weight, an excipient in an amount that is 50-60% of the capsule by weight, and tocophersolan in an amount that is 5-15% of the capsule by weight, a capsule comprising 60-70% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 20-30% of an excipient by weight, and 5-15% of tocophersolan by weight, a capsule comprising 45-55% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 35-45% of an excipient by weight, and 5-15% of tocophersolan by weight, a capsule comprising a citrate salt of cis-4-[2-{[(3S,4R)-3-fluorooxan-4-yl]amino}-8-(2,4,6-trichloroanilino)-9H-purin-9-yl]-1-methylcyclohexane-1-carboxamide in an amount that is 0.5-20% of the capsule weight, and sodium lauryl sulfate, or a tablet comprising 15-25% of cis-4-[2-{[(3S,4R)-3-fluorooxan-4-yl]amino}-8-(2,4,6-trichloroanilino)-9H-purin-9-yl]-1-methylcyclohexane-1-carboxamide or an isotopologue, pharmaceutically acceptable salt, tautomer, solvate, hydrate, co crystal, clathrate, or polymorph thereof by weight, 32-43% of microcrystalline cellulose by weight, 32-43% of mannitol by weight, 2-6% of croscarmellose sodium by weight, 0.3-0.7% of fumed silica by weight, and 0.5-1.5% magnesium stearate by weight.

8. The method of claim 7, wherein the cancer is melanoma, colorectal cancer, stomach cancer, head and neck cancer, thyroid cancer, bladder cancer, CNS cancer, lung cancer, pancreatic cancer, or soft tissue cancer.

9. The method of claim 7, wherein the cancer is bladder cancer, breast cancer, CNS cancer, colon cancer, gastrointestinal cancer, endocrine cancer, female genitoureal cancer, head and neck cancer, hematopoietic cancer, kidney cancer, liver cancer, lung cancer, melanoma, pancreas cancer, prostate cancer, or soft tissue cancer.

10. The method of claim 7, wherein the cancer is glioma, neuroblastoma, stomach cancer, thyroid cancer, adrenal gland cancer, cancer of the uterus, cervix, ovary clear cell, or vulva, leukemia, myeloma, non-small cell lung cancer (NSCLC), small cell lung cancer (SCLC), sarcoma or osteosarcoma.

11. The method of claim 7, wherein the cancer is hepatocellular carcinoma (HCC).

12. The method of claim 7, wherein the cancer is colorectal cancer (CRC), melanoma, gastric cancer, hepatocellular carcinoma, lung cancer, pancreatic cancer, leukemia, multiple myeloma, stomach cancer or sarcoma.

13. A method for achieving a stringent complete response, complete response, very good partial response, or partial response, as determined by the International Uniform Response Criteria for Multiple Myeloma (IURC) in a patient having multiple myeloma,
comprising administering to the patient an effective amount of a formulation, wherein the formulation is
a capsule comprising cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof in an amount that is 30-40% of the capsule by weight, an excipient in an amount that is 50-60% of the capsule by weight, and tocophersolan in an amount that is 5-15% of the capsule by weight,
a capsule comprising 60-70% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 20-30% of an excipient by weight, and 5-15% of tocophersolan by weight,
a capsule comprising 45-55% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 35-45% of an excipient by weight, and 5-15% of tocophersolan by weight,
a capsule comprising a citrate salt of cis-4-[2-{[(3S,4R)-3-fluorooxan-4-yl]amino}-8-(2,4,6-trichloroanilino)-9H-purin-9-yl]-1-methylcyclohexane-1-carboxamide in an amount that is 0.5-20% of the capsule weight, and sodium lauryl sulfate, or
a tablet comprising 15-25% of cis-4-[2-{[(3S,4R)-3-fluorooxan-4-yl]amino}-8-(2,4,6-trichloroanilino)-9H-purin-9-yl]-1-methylcyclohexane-1-carboxamide or an isotopologue, pharmaceutically acceptable salt, tautomer, solvate, hydrate, co crystal, clathrate, or polymorph thereof by weight, 32-43% of microcrystalline cellulose by weight, 32-43% of mannitol by weight, 2-6% of croscarmellose sodium by weight, 0.3-0.7% of fumed silica by weight, and 0.5-1.5% magnesium stearate by weight.

14. A method for inducing a therapeutic response assessed with the Response Assessment for Neuro-Oncology (RANO) Working Group for glioblastoma multiforme (GBM) in a patient having GBM, comprising administering to the patient an effective amount of a formulation,
wherein the formulation is
a capsule comprising cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof in an amount that is 30-40% of the capsule by weight, an excipient in an amount that is 50-60% of the capsule by weight, and tocophersolan in an amount that is 5-15% of the capsule by weight,
a capsule comprising 60-70% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 20-30% of an excipient by weight, and 5-15% of tocophersolan by weight,
a capsule comprising 45-55% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 35-45% of an excipient by weight, and 5-15% of tocophersolan by weight,
a capsule comprising a citrate salt of cis-4-[2-{[(3S,4R)-3-fluorooxan-4-yl]amino}-8-(2,4,6-trichloroanilino)-9H-purin-9-yl]-1-methylcyclohexane-1-carboxamide in an amount that is 0.5-20% of the capsule weight, and sodium lauryl sulfate, or
a tablet comprising 15-25% of cis-4-[2-{[(3S,4R)-3-fluorooxan-4-yl]amino}-8-(2,4,6-trichloroanilino)-9H-purin-9-yl]-1-methylcyclohexane-1-carboxamide or an isotopologue, pharmaceutically acceptable salt, tautomer, solvate, hydrate, co crystal, clathrate, or polymorph thereof by weight, 32-43% of microcrystalline cellulose by weight, 32-43% of mannitol by weight, 2-6% of croscarmellose sodium by weight, 0.3-0.7% of fumed silica by weight, and 0.5-1.5% magnesium stearate by weight.

15. The method of claim 14, wherein the cancer is melanoma, colorectal cancer, stomach cancer, head and neck cancer, thyroid cancer, bladder cancer, CNS cancer, lung cancer, pancreatic cancer, or soft tissue cancer.

16. The method of claim 14, wherein the cancer is bladder cancer, breast cancer, CNS cancer, colon cancer, gastrointestinal cancer, endocrine cancer, female genitoureal cancer, head and neck cancer, hematopoietic cancer, kidney cancer, liver cancer, lung cancer, melanoma, pancreas cancer, prostate cancer, or soft tissue cancer.

17. The method of claim 14, wherein the cancer is glioma, neuroblastoma, stomach cancer, thyroid cancer, adrenal gland cancer, cancer of the uterus, cervix, ovary clear cell, or vulva, leukemia, myeloma, non-small cell lung cancer (NSCLC), small cell lung cancer (SCLC), sarcoma or osteosarcoma.

18. The method of claim 14, wherein the cancer is hepatocellular carcinoma (HCC).

19. The method of claim 14, wherein the cancer is colorectal cancer (CRC), melanoma, gastric cancer, hepatocellular carcinoma, lung cancer, pancreatic cancer, leukemia, multiple myeloma, stomach cancer or sarcoma.

20. A method for improving the Eastern Cooperative Oncology Group Performance Status (ECOG) of a patient having a cancer, comprising administering to the patient an effective amount of a formulation, wherein the formulation is
- a capsule comprising cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof in an amount that is 30-40% of the capsule by weight, an excipient in an amount that is 50-60% of the capsule by weight, and tocophersolan in an amount that is 5-15% of the capsule by weight,
- a capsule comprising 60-70% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 20-30% of an excipient by weight, and 5-15% of tocophersolan by weight,
- a capsule comprising 45-55% cis-4-[2-{[(3S,4R)-3-fluorooxan-4-yl]amino}-8-(2,4,6-trichloroanilino)-9H-purin-9-yl]-1-methylcyclohexane-1-carboxamide, or a pharmaceutically acceptable salt, tautomer, solvate, hydrate, co-crystal, clathrate, or polymorph thereof by weight, 35-45% of an excipient by weight, and 5-15% of tocophersolan by weight,
- a capsule comprising a citrate salt of cis-4-[2-{[(3S,4R)-3-fluorooxan-4-yl]amino}-8-(2,4,6-trichloroanilino)-9H-purin-9-yl]-1-methylcyclohexane-1-carboxamide in an amount that is 0.5-20% of the capsule weight, and sodium lauryl sulfate, or
- a tablet comprising 15-25% of cis-4-[2-{[(3S,4R)-3-fluorooxan-4-yl]amino}-8-(2,4,6-trichloroanilino)-9H-purin-9-yl]-1-methylcyclohexane-1-carboxamide or an isotopologue, pharmaceutically acceptable salt, tautomer, solvate, hydrate, co crystal, clathrate, or polymorph thereof by weight, 32-43% of microcrystalline cellulose by weight, 32-43% of mannitol by weight, 2-6% of croscarmellose sodium by weight, 0.3-0.7% of fumed silica by weight, and 0.5-1.5% magnesium stearate by weight.

21. The method of claim 20, wherein the cancer is melanoma, colorectal cancer, stomach cancer, head and neck cancer, thyroid cancer, bladder cancer, CNS cancer, lung cancer, pancreatic cancer, or soft tissue cancer.

22. The method of claim 20, wherein the cancer is bladder cancer, breast cancer, CNS cancer, colon cancer, gastrointestinal cancer, endocrine cancer, female genitoureal cancer, head and neck cancer, hematopoietic cancer, kidney cancer, liver cancer, lung cancer, melanoma, pancreas cancer, prostate cancer, or soft tissue cancer.

23. The method of claim 20, wherein the cancer is glioma, neuroblastoma, stomach cancer, thyroid cancer, adrenal gland cancer, cancer of the uterus, cervix, ovary clear cell, or vulva, leukemia, myeloma, non-small cell lung cancer (NSCLC), small cell lung cancer (SCLC), sarcoma or osteosarcoma.

24. The method of claim 20, wherein the cancer is hepatocellular carcinoma (HCC).

25. The method of claim 20, wherein the cancer is colorectal cancer (CRC), melanoma, gastric cancer, hepatocellular carcinoma, lung cancer, pancreatic cancer, leukemia, multiple myeloma, stomach cancer or sarcoma.

\* \* \* \* \*